(12) United States Patent
Kearney et al.

(10) Patent No.: US 11,276,151 B2
(45) Date of Patent: Mar. 15, 2022

(54) INPAINTING DENTAL IMAGES WITH MISSING ANATOMY

(71) Applicant: Retrace Labs, San Francisco, CA (US)

(72) Inventors: Vasant Kearney, San Francisco, CA (US); Hamid Hekmatian, San Francisco, CA (US); Ali Sadat, San Francisco, CA (US)

(73) Assignee: Retrace Labs, San Francisco, CA (US)

( * ) Notice: Subject to any disclaimer, the term of this patent is extended or adjusted under 35 U.S.C. 154(b) by 0 days.

(21) Appl. No.: 16/900,726

(22) Filed: Jun. 12, 2020

(65) Prior Publication Data
US 2020/0410649 A1    Dec. 31, 2020

Related U.S. Application Data

(63) Continuation-in-part of application No. 16/875,922, filed on May 15, 2020.
(Continued)

(51) Int. Cl.
*G06K 9/00* (2006.01)
*G06T 5/00* (2006.01)
(Continued)

(52) U.S. Cl.
CPC ............ *G06T 5/005* (2013.01); *A61B 5/0088* (2013.01); *A61B 5/7267* (2013.01); *A61B 6/032* (2013.01);
(Continued)

(58) Field of Classification Search
CPC ................... G06T 5/005; G06T 7/0014; G06T 2207/20084; G06T 2207/30036;
(Continued)

(56) References Cited

U.S. PATENT DOCUMENTS 8,416,984 B2    4/2013    Liang et al.
9,026,242 B2    5/2015    Rivers et al.
(Continued)

FOREIGN PATENT DOCUMENTS

WO    2021046241 A1    3/2021

OTHER PUBLICATIONS

Lee, Fully Automatic Alveolar Bone Level and Teeth Segmentation in Dental Panoramic Images for Diagnosis of Periodontitis, Proceedings of Machine Learning Research, 2019.
(Continued)

*Primary Examiner* — Van D Huynh
(74) *Attorney, Agent, or Firm* — David R. Stevens; Stevens Law Group

(57) ABSTRACT

Dental images are processed according to a first machine learning model to determine teeth labels. The teeth labels and image are processed using a second machine learning model to label anatomy. The anatomy labels, teeth labels, and image are processed using a third machine learning model to obtain feature measurements, such as pocket depth and clinical attachment level. The feature measurements, labels, and image may be input to a fourth machine learning model to obtain a diagnosis for a periodontal condition. Machine learning models may further be used to reorient, decontaminate, and restore the image prior to processing. A machine learning model may be trained with images and randomly generated masks in order to perform inpainting of dental images with missing information.

20 Claims, 34 Drawing Sheets

Related U.S. Application Data

(60) Provisional application No. 62/867,817, filed on Jun. 27, 2019, provisional application No. 62/868,864, filed on Jun. 29, 2019, provisional application No. 62/868,870, filed on Jun. 29, 2019, provisional application No. 62/916,966, filed on Oct. 18, 2019.

(51) Int. Cl.
| | |
|---|---|
| *G06T 7/00* | (2017.01) |
| *G06N 3/08* | (2006.01) |
| *G06N 3/04* | (2006.01) |
| *A61B 6/12* | (2006.01) |
| *A61B 5/00* | (2006.01) |
| *A61B 6/00* | (2006.01) |
| *A61B 6/03* | (2006.01) |

(52) U.S. Cl.
CPC .............. *A61B 6/12* (2013.01); *A61B 6/5217* (2013.01); *G06N 3/0454* (2013.01); *G06N 3/08* (2013.01); *G06T 7/0014* (2013.01); *G06T 2207/20081* (2013.01); *G06T 2207/20084* (2013.01); *G06T 2207/30036* (2013.01)

(58) Field of Classification Search
CPC ......... G06T 2207/20081; G06T 7/0012; G06T 2207/10088; G06T 2207/10028; G06T 2207/10116; G06T 2207/10081; A61B 6/12; A61B 5/7267; A61B 6/5217; A61B 6/032; A61B 5/0088; A61B 6/14; G06N 3/08; G06N 3/0454; G06N 3/0445; G06N 3/0481; G06N 3/088; G06N 20/20
USPC ....................................................... 382/128
See application file for complete search history.

(56) References Cited

U.S. PATENT DOCUMENTS

| | | | |
|---|---|---|---|
| 9,760,978 B1* | 9/2017 | Lu | G06N 3/08 |
| 10,932,890 B1 | 3/2021 | Sant et al. | |
| 10,937,108 B1 | 3/2021 | Tabak et al. | |
| 11,158,046 B2 | 10/2021 | Jelicich et al. | |
| 2009/0074278 A1 | 3/2009 | Beaulieu | |
| 2010/0121658 A1* | 5/2010 | Kaminski | G16H 50/20 705/3 |
| 2012/0189182 A1* | 7/2012 | Liang | G16H 10/60 382/131 |
| 2015/0057675 A1 | 2/2015 | Akeel et al. | |
| 2016/0135925 A1 | 5/2016 | Mason | |
| 2016/0220200 A1 | 8/2016 | Sandholm | |
| 2017/0168812 A1 | 6/2017 | Golay et al. | |
| 2018/0039733 A1* | 2/2018 | Golay | A61B 6/14 |
| 2018/0357766 A1* | 12/2018 | Van Der Poel | G06T 7/12 |
| 2019/0180443 A1 | 6/2019 | Xue | |
| 2019/0197670 A1* | 6/2019 | Ferrer | G06K 9/00268 |
| 2019/0231490 A1 | 8/2019 | Sabina | |
| 2019/0313963 A1* | 10/2019 | Hillen | G06N 3/0454 |
| 2020/0134815 A1* | 4/2020 | Ezhov | G06T 3/4007 |
| 2020/0146646 A1* | 5/2020 | Tuzoff | G06T 7/0012 |
| 2020/0281697 A1 | 9/2020 | Brandt | |
| 2020/0320685 A1 | 10/2020 | Anssari | |
| 2021/0073977 A1 | 3/2021 | Carter et al. | |
| 2021/0074425 A1 | 3/2021 | Carter et al. | |
| 2021/0082184 A1 | 3/2021 | Claessen | |
| 2021/0104048 A1 | 4/2021 | Nishimura | |
| 2021/0134440 A1 | 5/2021 | Menavsky | |
| 2021/0183022 A1* | 6/2021 | Wang | G06T 3/4053 |
| 2021/0224919 A1 | 7/2021 | Tabak et al. | |
| 2021/0338387 A1 | 11/2021 | Inam et al. | |
| 2021/0343400 A1 | 11/2021 | Inam et al. | |

OTHER PUBLICATIONS

Balaei, Automatic detection of periodontitis using intra-oral images, 2017.

Arabi, Automatic Diagnosis of Dental Diseases, in International Conference on Next Generation Computing Technologies, 2017.

Atieh, M.A., et al., Predicting peri-implant disease: Chi-square automatic interaction detection (CHAID) decision tree analysis of risk indicators. Journal of periodontology, 2019.

Lin, P., Automatic methods for alveolar bone loss degree measurement in periodontitis periapical radiographs. Computer methods and programs in biomedicine, 2017. 148: p. 1-11.

Kearney, V., et al., Automated landmark-guided deformable image registration. Physics in Medicine & Biology, 2014. 60(1): p. 101.

Chan, J.W., et al., A Convolutional Neural Network Algorithm for Automatic Segmentation of Head and Neck Organs-at-Risk Using Deep Lifelong Learning. Medical Physics, 2019.

Nie, D., et al. Medical image synthesis with context-aware generative adversarial networks, in International Conference on Medical Image Computing and Computer-Assisted Intervention. 2017. Springer.

Goodfellow, I., et al. Generative adversarial nets, in Advances in neural information processing systems. 2014.

Kearney et al., An unsupervised convolutional neural network-based algorithm for deformable image registration, 2018.

Kearney et al., Canny edge-based deformable image registration, 2017.

Kearney et al., DoseNet: a volumetric dose prediction algorithm using 3D fully-convolutional neural networks, 2018.

Li et al., Volumetric Medical Image Segmentation: A 3D Deep Coarse-to-Fine Framework and Its Adversarial Examples, 2019.

Kearney et al., The application of artificial intelligence in the IMRT planning process for head and neck cancer, 2018.

Zantedeschi et al., Efficient defenses against adversarial attacks. In Proceedings of the 10th ACM Workshop on Artificial Intelligence and Security (pp. 39-49), 2017.

Xie et al., Mitigating adversarial effects through randomization, 2017.

Tramèr et al., Ensemble adversarial training: Attacks and defenses. 2017.

Raghunathan et al., Certified defenses against adversarial examples. 2018.

Xu et al., Feature squeezing: Detecting adversarial examples in deep neural networks. 2017.

Prakash et al., Deflecting adversarial attacks with pixel deflection. In *Proceedings of the IEEE conference on computer vision and pattern recognition* (pp. 8571-8580). 2018.

Chen et al., Shapeshifter: Robust physical adversarial attack on faster r-cnn object detector. In *Joint European Conference on Machine Learning and Knowledge Discovery in Databases* (pp. 52-68). Springer, Cham. 2018.

Hosseini et al., Semantic adversarial examples. in *Proceedings of the IEEE Conference on Computer Vision and Pattern Recognition Workshops* (pp. 1614-1619). 2018.

Vatian et al., Impact of Adversarial Examples on the Efficiency of Interpretation and Use of Information from High-Tech Medical Images. In *2019 24th Conference of Open Innovations Association (FRUCT)* (pp. 472-478). IEEE. 2019.

Zhang et al.. You only propagate once: Painless adversarial training using maximal principle, 2019.

Ren et al., Brain MR Image Segmentation in Small Dataset with Adversarial Defense and Task Reorganization. In *International Workshop on Machine Learning in Medical Imaging* (pp. 1-8). Springer, Cham. 2019.

Xue et al., Improving Robustness of Medical Image Diagnosis with Denoising Convolutional Neural Networks. In *International Conference on Medical Image Computing and Computer-Assisted Intervention* (pp. 846-854). Springer, Cham. 2019.

Liu et al., No Surprises: Training Robust Lung Nodule Detection for Low-Dose CT Scans by Augmenting with Adversarial Attacks. 2020.

Ma et al., Understanding adversarial attacks on deep learning based medical image analysis systems. *Pattern Recognition*, 107332. 2020.

(56) References Cited

OTHER PUBLICATIONS

Kearney et al. "DoseGAN: a generative adversarial network for synthetic dose prediction using attention-gated discrimination and generation." Scientific reports 10, No. 1 (2020): 1-8.
Kearney et al. "Attention-Aware Discrimination for MR-to-CT Image Translation Using Cycle-Consistent Generative Adversarial Networks." Radiology: Artificial Intelligence 2, No. 2 (2020): e190027.
Kearney et al. "Attention-enabled 3D boosted convolutional neural networks for semantic CT segmentation using deep supervision." Physics in Medicine & Biology 64, No. 13 (2019): 135001.
Kearney et al. "A multi-task CNN model for autosegmentation of prostate patients." International Journal of Radiation Oncology• Biology• Physics 102, No. 3 (2018): S214.
Sang-Jeong Lee, Fully Automatic Alveolar Bone Level and Teeth Segmentation in Dental Panoramic Images for Diagnosis of Periodontitis, Proceedings of Machine Learning Research, 2019.

\* cited by examiner

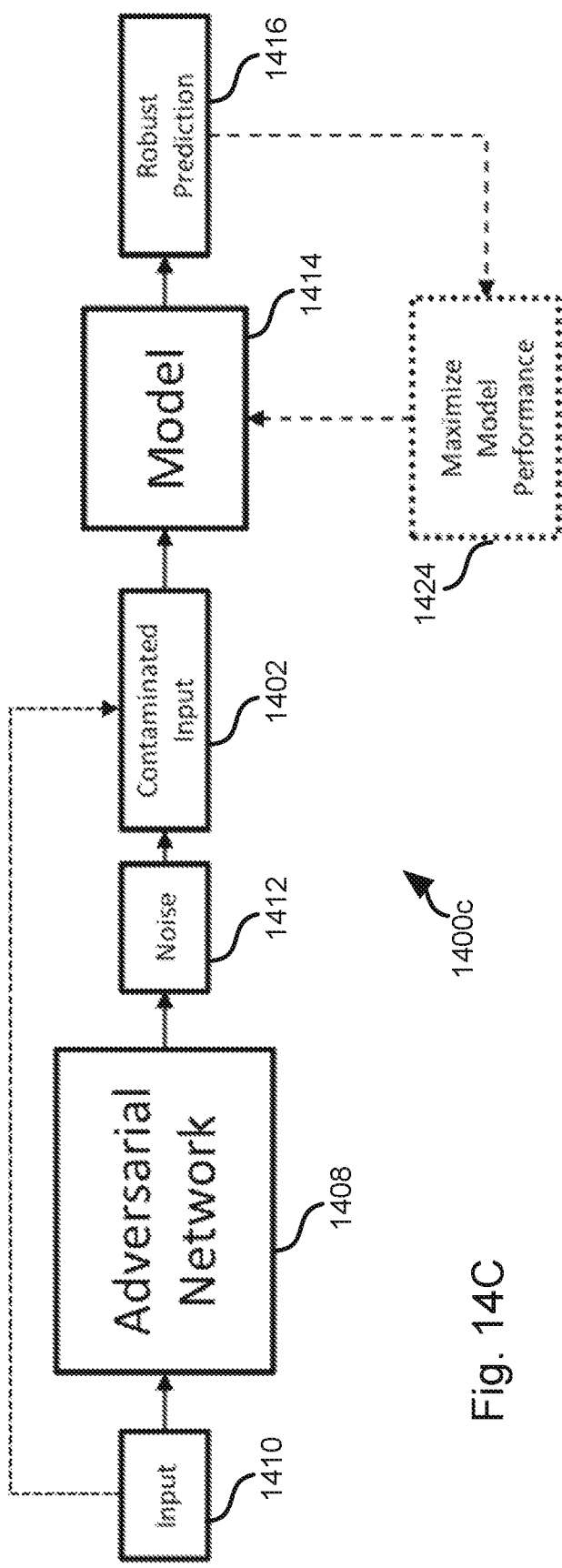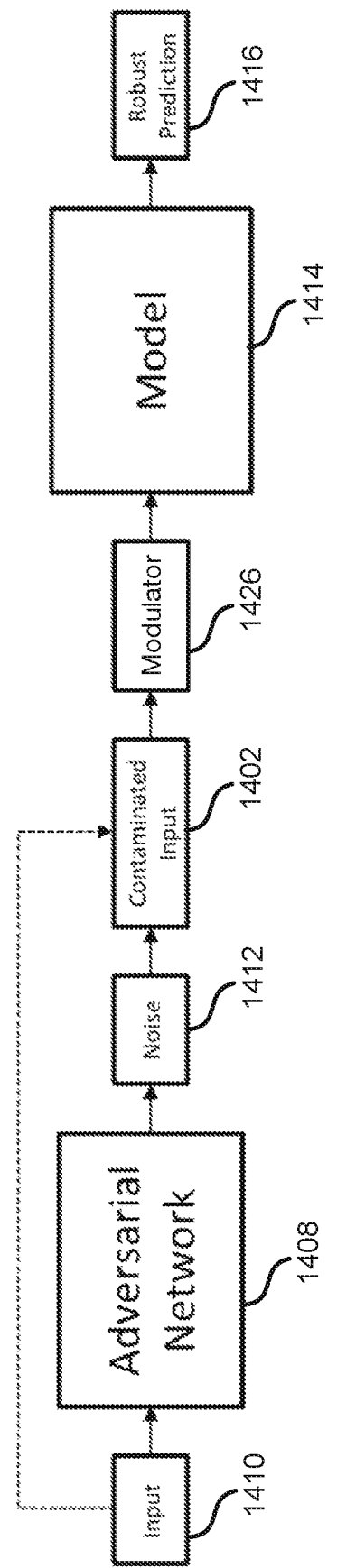
Fig. 14C
Fig. 14D

INPAINTING DENTAL IMAGES WITH MISSING ANATOMY

RELATED APPLICATIONS

This application is a continuation in part of U.S. application Ser. No. 16/875,922 filed May 15, 2020 and entitled ARTIFICIAL INTELLIGENCE ARCHITECTURE FOR IDENTIFICATION OF PERIODONTAL FEATURES.

This application claims the benefit of the following applications, all of which are hereby incorporated herein by reference in their entirety:

U.S. Provisional Application Ser. No. 62/867,817 filed Jun. 27, 2019, and entitled SYSTEM AND METHODS FOR AUTOMATED CARIES CLASSIFICATION, SCORING, QUANTIFICATION, AND INSURANCE CLAIMS ADJUDICATION.

U.S. Provisional Application Ser. No. 62/868,864 filed Jun. 29, 2019, and entitled SYSTEMS AND METHODS FOR ARTIFICIAL INTELLIGENCE-BASED DENTAL IMAGE TO TEXT GENERATION.

U.S. Provisional Application Ser. No. 62/868,870 filed Jun. 29, 2019, and entitled AN AUTOMATED DENTAL PATIENT IDENTIFICATION PLATFORM.

U.S. Provisional Application Ser. No. 62/916,966 filed Oct. 18, 2019, and entitled SYSTEMS AND METHODS FOR AUTOMATED ORTHODONTIC RISK ASSESSMENT, MEDICAL NECESSITY DETERMINATION, AND TREATMENT COURSE PREDICTION.

FIELD OF THE INVENTION

This invention relates to automating the analysis of dental images.

BACKGROUND

The field of dentistry relates to a broad range of oral healthcare, which are often discretized into several sub-fields such as disease of the bone (periodontitis), disease of the tooth (caries), or bone and tooth alignment (orthodontics). Although these sub-fields are unique and clinicians undergo special training to specialize in these sub-fields, they share some commonalities. Although different image modalities are favored in sub-fields more than others, all sub-fields utilize similar imaging strategies such as full mouth series (FMX), cone-beam computed tomography (CBCT), cephalometric, panoramic, and intra-oral images. All sub-fields of dentistry use images for assessment of patient orientation, anatomy, comorbidities, past medical treatment, age, patient identification, treatment appropriateness, and time series information.

Diagnosis of disease in the dental field is performed by visual inspection of dental anatomy and features and by analysis of images obtained by X-ray or other imaging modality. There have been some attempts made to automate this process.

BRIEF DESCRIPTION OF THE FIGURES

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which:

FIG. 14C is a schematic block diagram of a system for protecting a machine learning model from adversarial images in accordance with an embodiment of the present invention;

FIG. 14D is a schematic block diagram of a system for modifying adversarial images to protect a machine learning model from corrupted images in accordance with an embodiment of the present invention;

DETAILED DESCRIPTION

Figure 1:
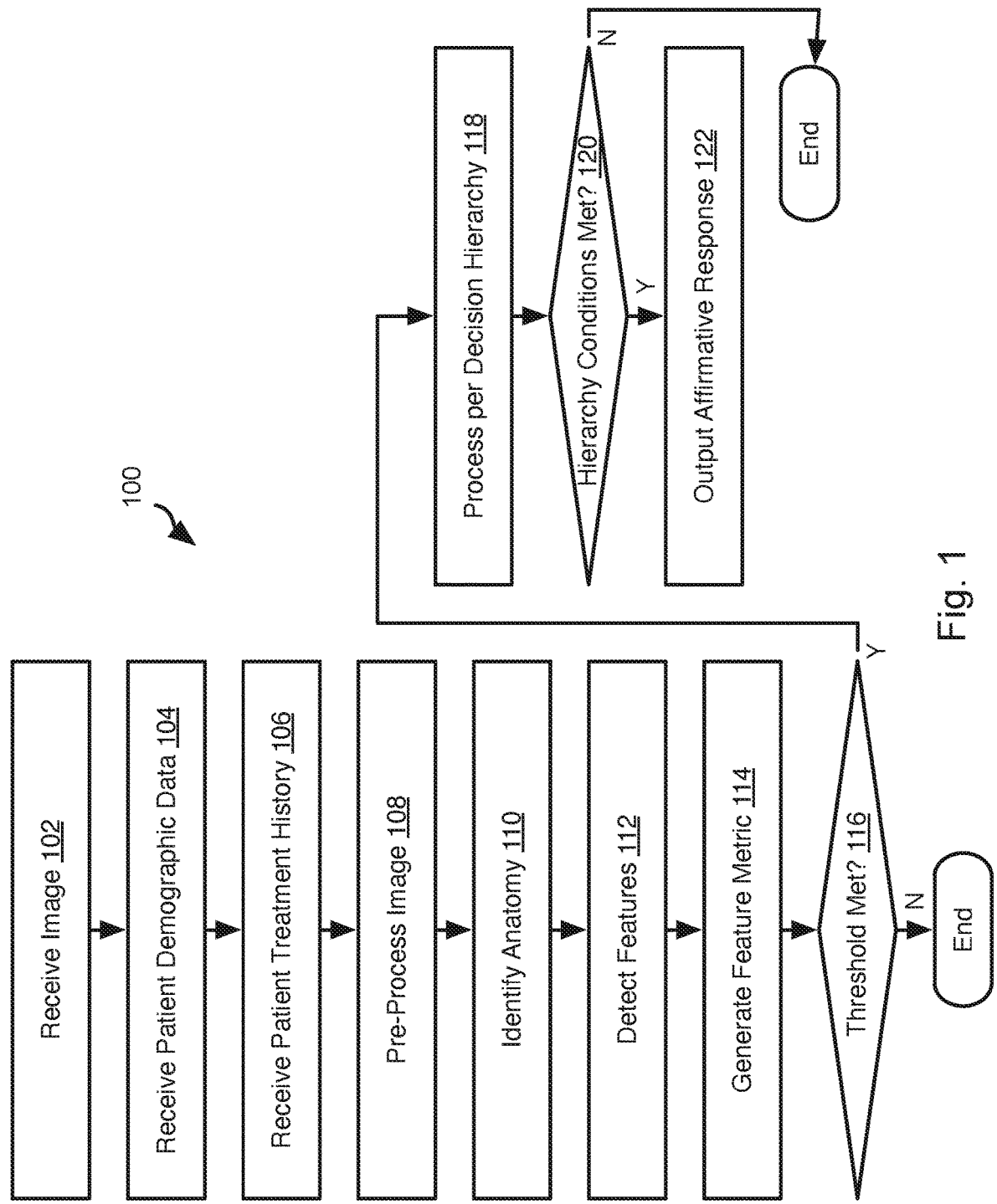
FIG. 1 is a process flow diagram of a method for classifying treatment in accordance with an embodiment of the present invention.

It will be readily understood that the components of the invention, as generally described and illustrated in the Figures herein, could be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

Embodiments in accordance with the invention may be embodied as an apparatus, method, or computer program product. Accordingly, the invention may take the form of an entirely hardware embodiment, an entirely software embodiment (including firmware, resident software, micro-code, etc.), or an embodiment combining software and hardware aspects that may all generally be referred to herein as a "module" or "system." Furthermore, the invention may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. In selected embodiments, a computer-readable medium may comprise any non-transitory medium that can contain, store, communicate, propagate, or transport the program for use by or in connection with the instruction execution system, apparatus, or device.

Computer program code for carrying out operations of the invention may be written in any combination of one or more programming languages, including an object-oriented programming language such as Java, Smalltalk, C++, or the like and conventional procedural programming languages, such as the "C" programming language or similar programming languages, and may also use descriptive or markup languages such as HTML, XML, JSON, and the like. The program code may execute entirely on a computer system as a stand-alone software package, on a stand-alone hardware unit, partly on a remote computer spaced some distance from the computer, or entirely on a remote computer or server. In the latter scenario, the remote computer may be connected to the computer through any type of network, including a local area network (LAN) or a wide area network (WAN), or the connection may be made to an external computer (for example, through the Internet using an Internet Service Provider).

The invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions or code. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a non-transitory computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

Referring to FIG. 1, a method 100 may be performed by a computer system in order to select an outcome for a set of input data. The outcome may be a determination whether a particular course of treatment is correct or incorrect. The method 100 may include receiving 102 an image. The image may be an image of patient anatomy indicating the periodontal condition of the patient. Accordingly, the image may be of a of a patient's mouth obtained by means of an X-ray (intra-oral or extra-oral, full mouth series (FMX), panoramic, cephalometric), computed tomography (CT) scan, cone-beam computed tomography (CBCT) scan, intra-oral image capture using an optical camera, magnetic resonance imaging (MRI), or other imaging modality.

The method 100 may further include receiving 104 patient demographic data, such as age, gender, underlying health conditions (diabetes, heart disease, cancer, etc.). The method 100 may further include receiving 106 a patient treatment history. This may include a digital representation of periodontal treatments the patient has received, such as cleanings, periodontal scaling, root planing, fillings, root canals, orthodontia, oral surgery, or other treatments or procedures performed on the teeth, gums, mouth, or jaw of the patient.

The method 100 may include pre-processing 108 the image received at step 102. Note that in some embodiments, the image received is correctly oriented, obtained using a desired imaging modality, and free of contamination or defects such that pre-processing is not performed. In other embodiments, some or all of re-orienting, removing contamination (e.g., noise), transforming to a different imaging modality, and correcting for other defects may be performed at step 108. In some embodiments, step 108 may correct for distortion due to foreshortening, elongation, metal artifacts, and image noise due to poor image acquisition from hardware, software, or patient setup.

Step 108 may further include classifying the image, such as classifying which portion of the patient's teeth and jaw is in the field of view of the image. For example, a full-mouth series (FMX) typically includes images classified as Premolar2, Molar3, Anterior1, Anterior2, Anterior3 and their respective corresponding locations such as Jaw Region, Maxilla, and Mandible. For each of these, the view may be classified as being the left side or right side of the patients face.

In the following description reference to an "image" shall be understood to interchangeably reference either the original image from step 102 or an image resulting from the pre-processing of step 108.

The method 100 may further include processing 110 the image to identify patient anatomy. Anatomy identified may be represented as a pixel mask identifying pixels of the image that correspond to the identified anatomy and labeled as corresponding to the identified anatomy. This may include identifying individual teeth. As known in the field of dentistry, each tooth is assigned a number. Accordingly, step 110 may include identifying teeth in the image and determining the number of each identified teeth. Step 110 may further include identifying other anatomical features for each identified tooth, such as its cementum-enamel junction (CEJ), boney points corresponding to periodontal disease around the tooth, gingival margin (GM), junctional epithelium (JE), or other features of the tooth that may be helpful in characterizing the health of the tooth and the gums and jaw around the tooth.

The method 100 may further include detecting 112 features present in the anatomy identified at step 110. This may include identifying caries, measuring clinical attachment level (CAL), measuring pocket depth (PD), or identifying other clinical conditions that may indicate the need for treatment. The identifying step may include generating a pixel mask defining pixels in the image corresponding to the detected feature. The method 100 may further include generating 114 a feature metric, i.e. a characterization of the feature. This may include performing a measurement based on the pixel mask from step 112. Step 114 may further take as inputs the image and anatomy identified from the image at step 110. For example, CAL or PD of teeth in an image may be measured, such as using the machine-learning approaches described below (see discussion of FIGS. 9 and 10)

The result of steps 108, 110, 112, and 114 is an image that may have been corrected, labels, e.g. pixel masks, indicating the location of anatomy and detected features and a measurement for each detected feature. This intermediate data may then be evaluated 116 with respect to a threshold. In particular, this may include an automated analysis of the detected and measured features with respect to thresholds. For example, CAL or PD measured using the machine-learning approaches described below may be compared to thresholds to see if treatment may be needed. Step 116 may also include evaluating some or all of the images, labels, detected features, and measurements for detected features a machine learning model to determine whether a diagnosis is appropriate (see FIG. 11).

If the result of step 116 is affirmative, then the method 100 may include processing 118 the feature metric from step 114 according to a decision hierarchy. The decision hierarchy may further operate with respect to patient demographic data from step 104 and the patient treatment history from step 106. The result of the processing according to the decision hierarchy may be evaluated at step 120. If the result is affirmative, than an affirmative response may be output 122. An affirmative response may indicate that the a course of treatment corresponding to the decision hierarchy is determined to be appropriate. If the result of processing 118 the decision hierarchy is negative, then the course of treatment corresponding to the decision hierarchy is determined not to be appropriate. The evaluation according to the method 100 may be performed before the fact, i.e. to determine whether to perform the course of treatment. The method 100 may also be performed after the fact, i.e. to determine whether a course of treatment that was already performed was appropriate and therefore should be paid for by insurance.

Figure 2:
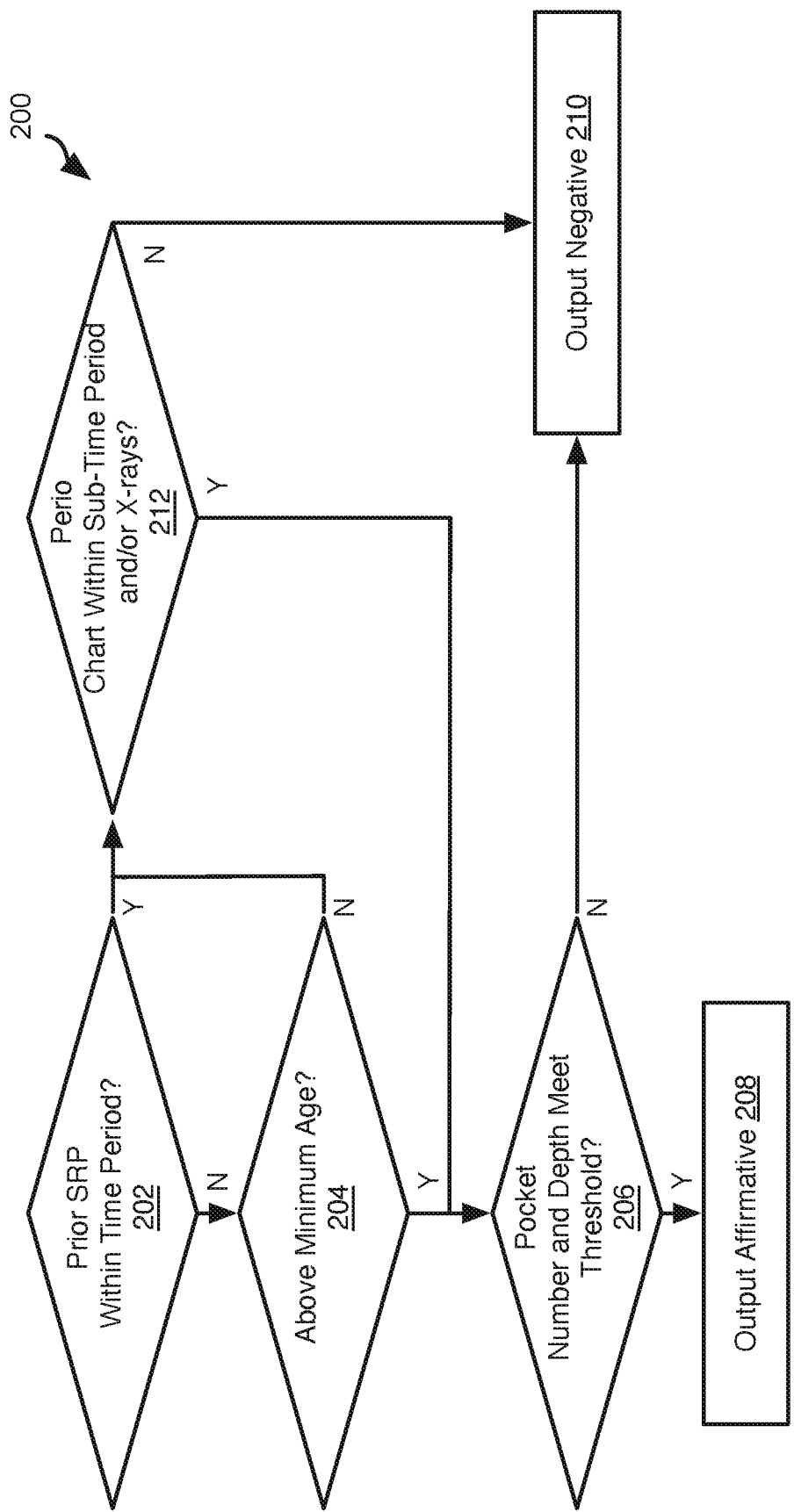
FIG. 2 is a process flow diagram of a hierarchy for classifying a treatment.

FIG. 2 illustrates a method 200 for evaluating a decision hierarchy, such as may be performed at step 118. The method 200 may be a decision hierarchy for determining whether scaling and root planing (SRP) should be performed for a patient. SRP is performed in response to the detection of pockets. Accordingly, the method 200 may be performed in response to detecting pockets at step 112 (e.g., pockets having a minimum depth, such as at least pocket having a depth of at least 5 mm) and determining that the size of these pockets as determined at step 114 meets a threshold condition at step 116, e.g. there being at least one pocket (or some other minimum number of pockets) having a depth above a minimum depth, e.g. 5 mm.

The method 200 may include evaluating 202 whether the treatment, SRP, has previously been administered within a threshold time period prior to a reference time that is either (a) the time of performance of the method 200 and (b) the time that the treatment was actually performed, i.e. the treatment for which the appropriateness is to be determined according to the method 100 and the method 200. For example, this may include whether SRP was performed within 24 months of the reference time.

If not, the method 200 may include evaluating 204 whether the patient is above a minimum age, such as 25 years old. If the patient is above the minimum age, the method 200 may include evaluating 206 whether the number of pockets having a depth exceeding a minimum pocket depth exceeds a minimum pocket number. For example, where the method 200 is performed to determine whether SRP is/was appropriate for a quadrant (upper left, upper right, lower left, lower right) of the patient's jaw, step 206 may include evaluating whether there are at least four teeth in that quadrant that collectively include at least 8 sites, each site including a pocket of at least 5 mm. Where the method 200 is performed to determine whether SRP is/was appropriate for an area that is less than an entire quadrant, step 206 may include evaluating whether there are one to three teeth that include at least 8 sites, each site including a pocket of at least 5 mm.

If the result of step 206 is positive, then an affirmative result is output, i.e. the course of treatment is deemed appropriate. If the result of step 206 is positive, then an affirmative result is output 208, i.e. the course of treatment is deemed appropriate. If the result of step 206 is negative, then a negative result is output 210, i.e. the course of treatment is deemed not to be appropriate.

If either of (a) SRP was found 202 to have been performed less than the time window from the reference time or (b) the patient is found 204 to be below the minimum age, the method 200 may include evaluating 212 whether a periodontal chart has been completed for the patient within a second time window from the reference time, e.g. six months. If the result of step 212 is positive, then processing may continue at step 206. If the result of step 212 is negative, then processing may continue at step 210.

The decision hierarchy of the method 200 is just one example. Decision hierarchies for other treatments may be evaluated according to the method 100, such as gingivectomy; osseous mucogingival surgery; free tissue grafts; flap reflection or resection and debridement (with or without osseous recontouring); keratinized/attached gingiva preservation; alveolar bone reshaping; bone grafting (with or without use of regenerative substrates); guided tissue regeneration; alveolar bone reshaping following any of the previously-mentioned procedures; and tissue wedge removal for performing debridement, flap adaptation, and/or pocket depth reduction. Examples of decision hierarchies for these treatments are illustrated in the U.S. Provisional Application Ser. No. 62/848,905.

Figure 3:
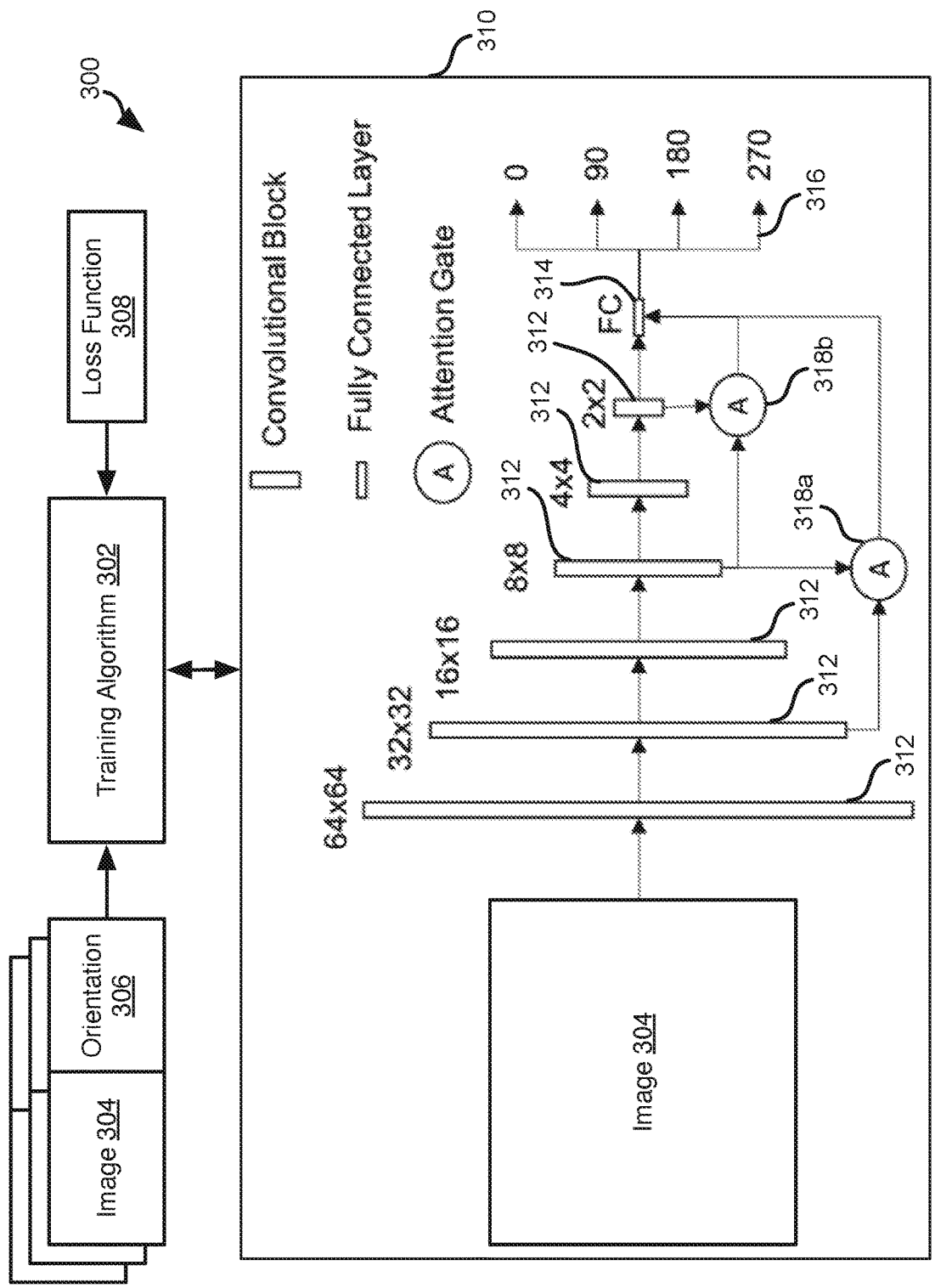
FIG. 3 is a schematic block diagram of a system for identifying image orientation in accordance with an embodiment of the present invention.

FIG. 3 is a schematic block diagram of a system 300 for identifying image orientation in accordance with an embodiment of the present invention. The illustrated system may be used to train a machine to determine image orientation as part of the pre-processing of step 108 of the method 100. In particular, once an image orientation is known, it may be rotated to a standard orientation for processing according to subsequent steps of the method 100.

As described below, machine learning models, such as a CNN, may be used to perform various tasks described above with respect to the method 100. Training of the CNN may be simplified by ensuring that the images used are in a standard orientation with respect to the anatomy represented in the images. When images are obtained in a clinical setting they are often mounted incorrectly by a human before being stored in a database. The illustrated system 300 may be used to determine the orientation of anatomy in an image such that they may be rotated to the standard orientation, if needed, prior to subsequent processing with another CNN or other machine learning model.

A training algorithm 302 takes as inputs training data entries that each include an image 304 according to any of the imaging modalities described herein and an orientation label 306 indicating the orientation of the image, e.g. 0 degrees, 90 degrees, 180 degrees, and 270 degrees. The orientation label 306 for an image may be assigned by a human observing the image and determining its orientation. For example, a licensed dentist may determine the label 306 for each image 304.

The training algorithm 302 may operate with respect to a loss function 308 and modify a machine learning model 310 in order to reduce the loss function 308 of the model 310. In this case, the loss function 308 may be a function that increases with a difference between the angle estimated by the model 310 for the orientation of an image 304 and the orientation label 306 of the image.

In the illustrated embodiment, the machine learning model 310 is a convolution neural network. For example, the machine learning model 310 may be an encoder-based densely-connected CNN with attention-gated skip connections and deep-supervision. In the illustrated embodiment, the CNN includes six multi-scale stages 312 followed by a fully connected layer 314, the output 316 of the fully connected layer 314 being an orientation prediction (e.g. 0 degrees, 90 degrees, 180 degrees, or 270 degrees).

In some embodiment, each multi-scale stage 312 may contain three 3×3 convolutional layers, which may be paired with batch-normalization and leaky rectified linear units (LeakyReLU). The first and last convolutional layers of each stage 312 may be concatenated via dense connections which help reduce redundancy within the CNN by propagating shallow information to deeper parts of the CNN.

Each multi-scale network stage 312 may be downscaled by a factor of two at the end of each multi-scale stage 312 by convolutional downsampling. The second and fourth multi-scale stages 312 may be passed through attention gates 318a, 318b before being concatenated with the last layer. For example, the gating signal of attention gate 318a that is applied to the second stage 312 may be derived from the output of the fourth stage 312. The gating signal of attention gate 318b that is applied to the fourth stage 312 may be derived from the output of the sixth stage 312. Not all regions of the image 304 are relevant for determining orientation, so the attention gates 318a, 318b may be used to selectively propagate semantically meaningful information to deeper parts of the CNN.

In some embodiments, the input image 304 to the CNN is a raw 64×64 pixel image and the output 316 of the network is a likelihood score for each possible orientation. The loss function 308 may be trained with categorical cross entropy which considers each orientation to be an orthogonal category. Adam optimization may be used during training which automatically estimates the lower order moments and helps estimate the step size which desensitizes the training routine to the initial learning rate.

In at least one possible embodiment, the images 304 are 3D images, such as a CT scan. Accordingly, the 3×3 convolutional kernels of the multi-scale networks with 3×3×3 convolutional kernels. The output 316 of the CNN may therefore map to four rotational configurations 0, 90, 180, and 270 along the superior-inferior axis as well as one orthogonal orientation in the superior-inferior direction.

Because machine learning models may be sensitive to training parameters and architecture, for all machine learning models described herein, including the machine learning model 310, a first set of training data entries may be used for hyperparameter testing and a second set of training data entries not included in the first set may be used to assess model performance prior to utilization.

The training algorithm 302 for this CNN and other CNNs and machine learning models described herein may be implemented using PYTORCH. Training of this CNN and other CNNs and machine learning models described herein may be performed using a GPU, such as NVIDIA's TESLA GPUs coupled with INTEL XEON CPUs. Other machine learning tools and computational platforms may also be used.

Generating inferences using this machine learning model 310 and other machine learning models described herein may be performed using the same type of GPU used for training or some other type of GPU or other type of computational platform. In other embodiment, inferences using this machine learning model 310 or other machine learning models described herein may be generated by placing the machine learning model on an AMAZON web services (AWS) GPU instance. During deployment, a server may instantiate the machine learning model and preload the model architecture and associated weights into GPU memory. A FLASK server may then load an image buffer from a database, convert the image into a matrix, such as a 32-bit matrix, and load it onto the GPU. The GPU matrix may then be passed through the machine learning model in the GPU instance to obtain an inference, which may then be stored in a database. Where the machine learning model transforms an image or pixel mask, the transformed image or pixel mask may be stored in an image array buffer after processing of the image using the machine learning model. This transformed image or pixel mask may then be stored in the database as well.

In the case of the machine learning model 310 of FIG. 3, the transformed image may be an image rotated from the orientation determined according to the machine learning model 310 to the standard orientation. The machine learning model 310 may perform the transformation or this may be performed by a different machine learning model or process.

Figure 4:
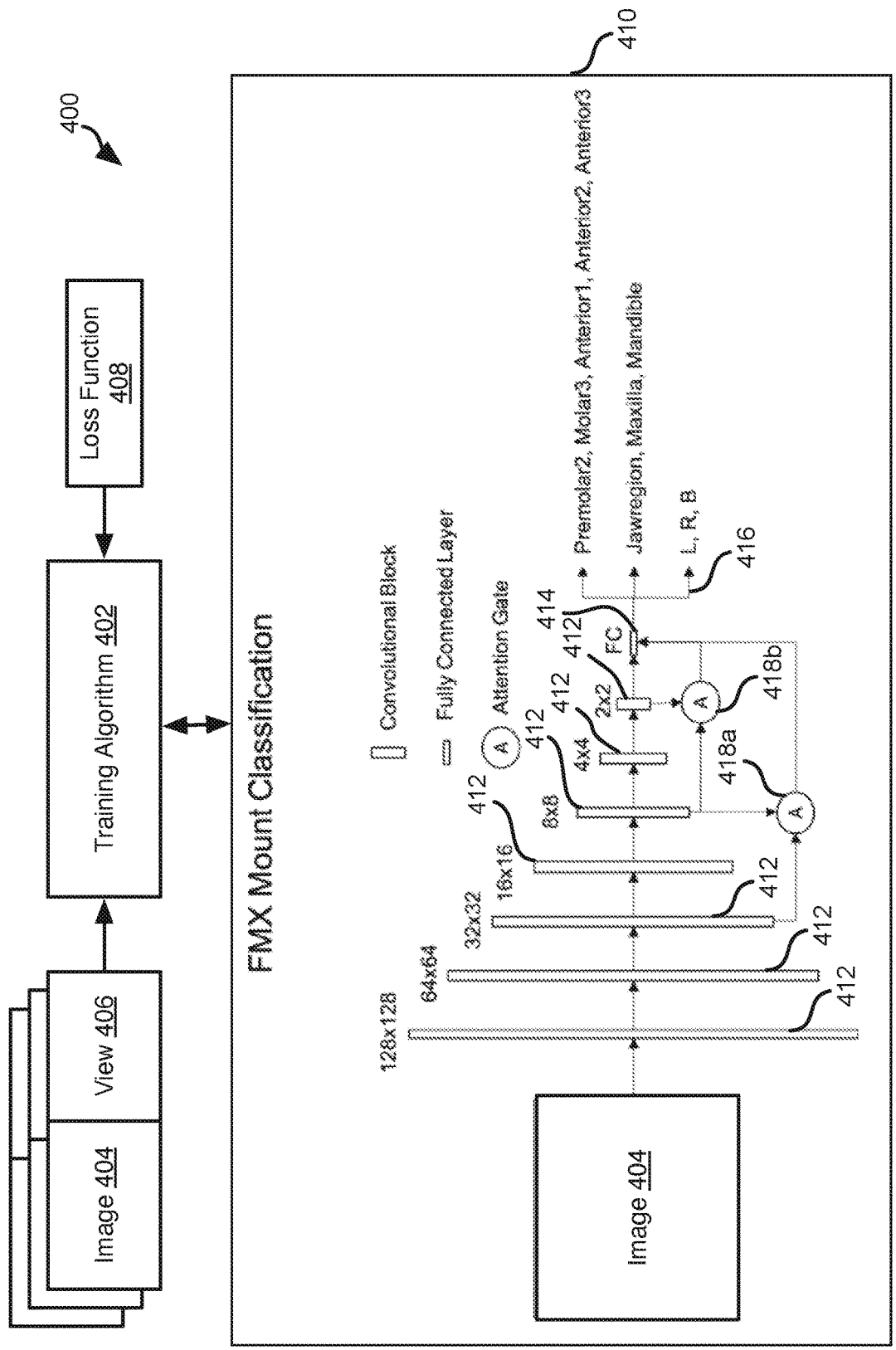
FIG. 4 is a schematic block diagram of a system for classifying images of a full mouth series in accordance with an embodiment of the present invention.

FIG. 4 is a schematic block diagram of a system 400 for determining the view of a full mouth series (FMX) that an image represents in accordance with an embodiment of the present invention. The illustrated architecture may be used to train a machine learning model to determine which view of the FMX an image corresponds to. The system 400 may be used to train a machine learning model to classify the view an image represents for use in pre-processing an image at step 108 of the method 100.

In dentistry, an FMX is often taken to gain comprehensive imagery of oral anatomy. Standard views are categorized by the anatomic region sequence indicating the anatomic region being viewed such as jaw region, maxilla, or mandible and an anatomic region modifier sequence indicating a particular sub-region being viewed such as premolar 2, molar 3, anterior 1, anterior 2, and anterior 3. In addition, each anatomic region sequence and anatomic region sequence modifier has a laterality indicting which side of the patient is being visualized, such as left (L), right (R), or ambiguous (A). Correct identification, diagnosis, and treatment of oral anatomy and pathology rely on accurate pairing of FMX mounting information of each image.

In some embodiment, the system 400 may be used to train a machine learning model to estimate the view of an image. Accordingly, the output of the machine learning model for a given input image will be a view label indicating an anatomic region sequence, anatomic region sequence modifier, and laterality visualized by the image. In some embodiments, the CNN architecture may include an encoder-based residually connected CNN with attention-gated skip connections and deep-supervision as described below.

In the system 400, A training algorithm 402 takes as inputs training data entries that each include an image 404 according to any of the imaging modalities described herein and a view label 406 indicating which of the view the image corresponds to (anatomic region sequence, anatomic region sequence modifier, and laterality). The view label 406 for an image may be assigned by a human observing the image and determining which of the image views it is. For example, a licensed dentist may determine the label 406 for each image 404.

The training algorithm 402 may operate with respect to a loss function 408 and modify a machine learning model 410 in order to reduce the loss function 408 of the model 410. In this case, the loss function 408 may be a function that is zero when a view label output by the model 410 for an image 406 matches the view label 406 for that image 404 and is non-zero, e.g. 1, when the view label output does not match the view label 406. Inasmuch as there are three parts to each label (anatomic region sequence, anatomic region modifier sequence, and laterality) there may be three loss functions 408, one for each part that is zero when the estimate for that part is correct and non-zero, e.g. 1, when the estimate for that part is incorrect. Alternatively, the loss function 408 may output a single value decreases with the number of parts of the label that are correct and increase with the number of parts of the label that are incorrect The training algorithm 402 may train a machine learning model 410 embodied as a CNN. In the illustrated embodiment, the CNN includes seven multi-scale stages 312 followed by a fully connected layer 414 that outputs an estimate for the anatomic region sequence, anatomic region modifier sequence, and laterality of an input image 404. Each multi-scale stage 412 may contain three 3×3 convolutional layers that may be paired with batchnormalization and leaky rectified linear units (LeakyReLU). The first and last convolutional layers of a stage 412 may be concatenated via residual connections which help reduce redundancy within the network by propagating shallow information to deeper parts of the network.

Each multi-scale stage 412 may be downscaled by a factor of two at the end of each multi-scale stage 412, such as by max pooling. The third and fifth multi-scale stages 412 may be passed through attention gates 418a, 418b, respectively, before being concatenated with the last stage 412. For example, the gating signal of attention gate 418a that is applied to the output of the third stage 412 may be derived from the fifth stage 412 and the gating signal applied by attention gate 418b to the output of the fifth stage 412 may be derived from the seventh stage 412. Not all regions of the image are relevant for classification, so attention gates 418a, 418b may be used to selectively propagate semantically meaningful information to deeper parts of the network.

The input images 404 may be raw 128×128 images, which may be rotated to a standard orientation according to the approach of FIG. 3. The output 416 of the machine learning model 410 may be a likelihood score for each of the anatomic region sequence, anatomic region modifier sequence, and laterality of the input image 404. The loss function 408 may be trained with categorical cross entropy, which considers each part of a label (anatomic region sequence, anatomic region modifier sequence, and laterality) to be an orthogonal category. Adam optimization may be used during training, which automatically estimates the lower order moments and helps estimate the step size which desensitizes the training routine to the initial learning rate.

In at least one possible embodiment, the images 404 are 3D images, such as a CT scan. Accordingly, the 3×3 convolutional kernels of the multi-scale stages 412 may be replaced with 3×3×3 convolutional kernels. The output of the machine learning model 410 in such embodiments may be a mapping of the CT scan to one of a number of regions within the oral cavity, such as the upper right quadrant, upper left quadrant, lower left quadrant, and lower right quadrant.

The training algorithm 402 and utilization of the trained machine learning model 410 may be implemented using PYTORCH and AWS GPU instances in the same manner as described above with respect to FIG. 3.

Figure 5:
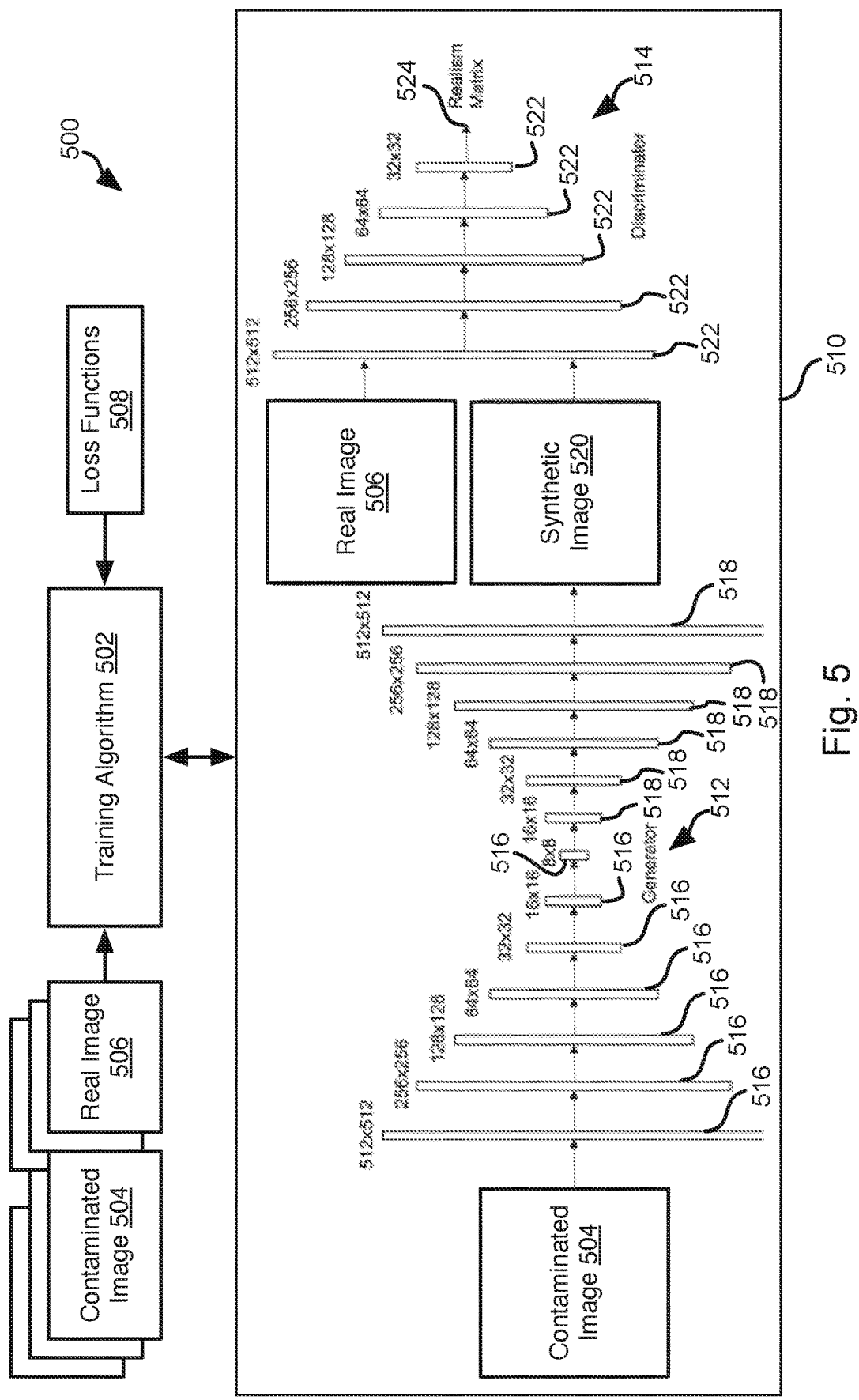
FIG. 5 is a schematic block diagram of a system for removing image contamination in accordance with an embodiment of the present invention.

FIG. 5 is a schematic block diagram of a system 500 for removing image contamination in accordance with an embodiment of the present invention. The system 500 may be used to train a machine learning model to remove contamination from images for use in pre-processing an image at step 108 of the method 100. In some embodiment, contamination may be removed from an image using the approach of FIG. 5 to obtain a corrected image and the corrected image may then be reoriented using the approach of FIG. 3 to obtain a reoriented image (though the image output from the approach of FIG. 3 may not always be rotated relative to the input image). The reoriented image may then be used to classifying the FMX view of the image using the approach of FIG. 4.

In some embodiment, the system 500 may be used to train a machine learning model to output an improved quality image for a given input image. In order to establish the correct diagnosis from dental images, it is often useful to have high resolution, high contrast, and artifact free images. It can be difficult to properly delineate dental anatomy if image degradation has occurred due to improper image acquisition, faulty hardware, patient setup error, or inadequate software. Poor image quality can take many forms such as noise contamination, poor contrast, or low resolution. The illustrated system 500 may be used to solve this problem.

In the system 500, A training algorithm 502 takes as inputs contaminated images 504 and real images 506. As for other embodiments, the images 504, 506 may be according to any of the imaging modalities described herein. The images 504 and 506 are unpaired in some embodiments, meaning the real images 506 are not uncontaminated versions of the contaminated images 504. Instead, the real images 506 may be selected from a repository of images and used to assess the realism of synthetic images generated using the system 500. The contaminated images 504 may be obtained by adding contamination to real images in the form of noise, distortion, or other defects. The training algorithm 502 may operate with respect to one or more loss functions 508 and modify a machine learning model 510 in order to reduce the loss functions 508 of the model 510.

In the illustrated embodiment, the machine learning model 510 may be embodied as a generative adversarial network (GAN) including a generator 512 and a discriminator 514. The generator 512 may be embodied as an encoder-decoder generator including seven multi-scale stages 516 in the encoder and seven multi-scale stages 518 in the decoder (the last stage 516 of the encoder being the first stage of the decoder). The discriminator 514 may include five multi-scale stages 522.

Each multi-scale stage 516, 518 within the generator 512 may use 4×4 convolutions paired with batchnormalization and rectified linear unit (ReLU) activations. Convolutional downsampling may be used to downsample each multi-scale stage 516 and transpose convolutions may be used between the multi-scale stages 518 to incrementally restore the original resolution of the input signal. The resulting high-resolution output channels of the generator 512 may be passed through a 1×1 convolutional layer and hyperbolic tangent activation function to produce a synthetic image 520. At each iteration, the synthetic image 520 and a real image 506 from a repository of images may be passed through the discriminator 514.

The discriminator 514 produces as an output 524 a realism matrix that is an attempt to differentiate between real and fake images. The realism matrix is a matrix of values, each value being an estimate as to which of the two input images is real. The loss function 508 may then operate on an aggregation of the values in the realism matrix, e.g. average of the values, a most frequently occurring value of the values, or some other function. The closer the aggregation is to the correct conclusion (determining that the synthetic image 520 is fake), the lower the output of the loss function 508. The realism matrix may be preferred over a conventional single output signal discriminator because it is better suited to capture local image style characteristics and it is easier to train.

In some embodiments, the loss functions 508 utilize level 1 (L1) loss to help maintain the spatial congruence of the synthetic image 520 and real image 506 and adversarial loss to encourage realism. The generator 512 and discriminator 514 may be trained simultaneously until the discriminator 514 can no longer differentiate between synthetic and real images or a Nash equilibrium has been reached.

In at least one possible embodiment, the system 500 may operate on three-dimensional images 504, 506, such as a CT scan. This may include replacing the 4×4 convolutional kernels with 4×4×4 convolutional kernels and replacing the 1×1 convolutional kernels with 1×1×1 convolutional kernels.

The training algorithm 502 and utilization of the trained machine learning model 510 may be implemented using PYTORCH and AWS GPU instances in the same manner as described above with respect to FIG. 3.

Figure 6A:
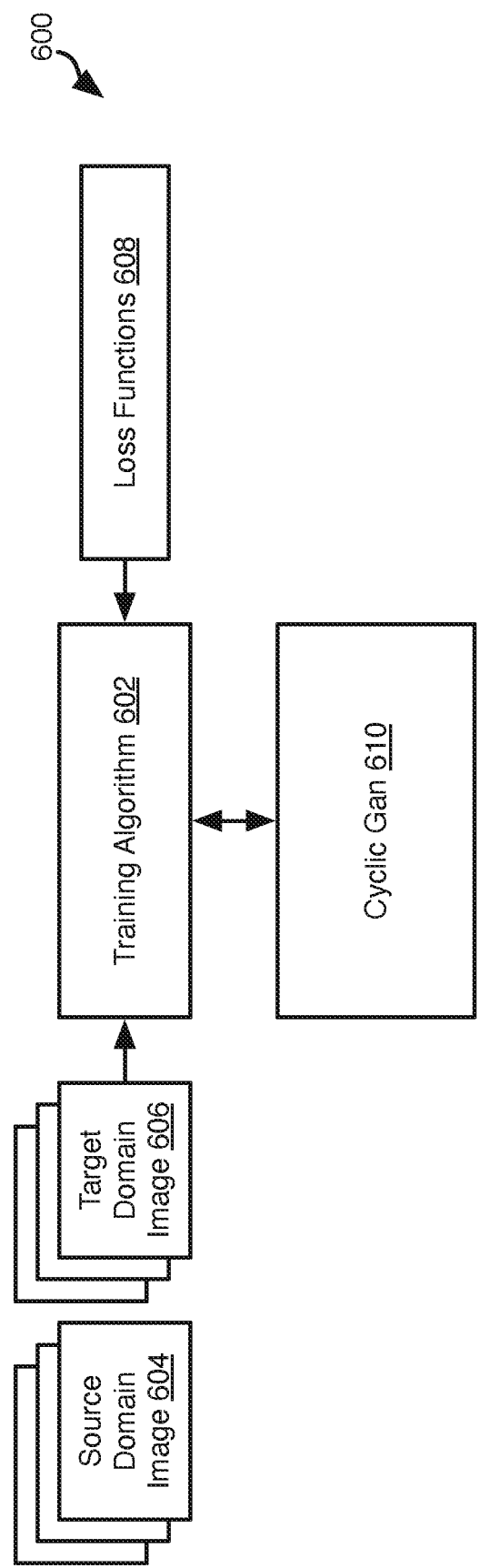
FIG. 6A is a schematic block diagram of system for performing image domain transfer in accordance with an embodiment of the present invention.
Figure 6B:
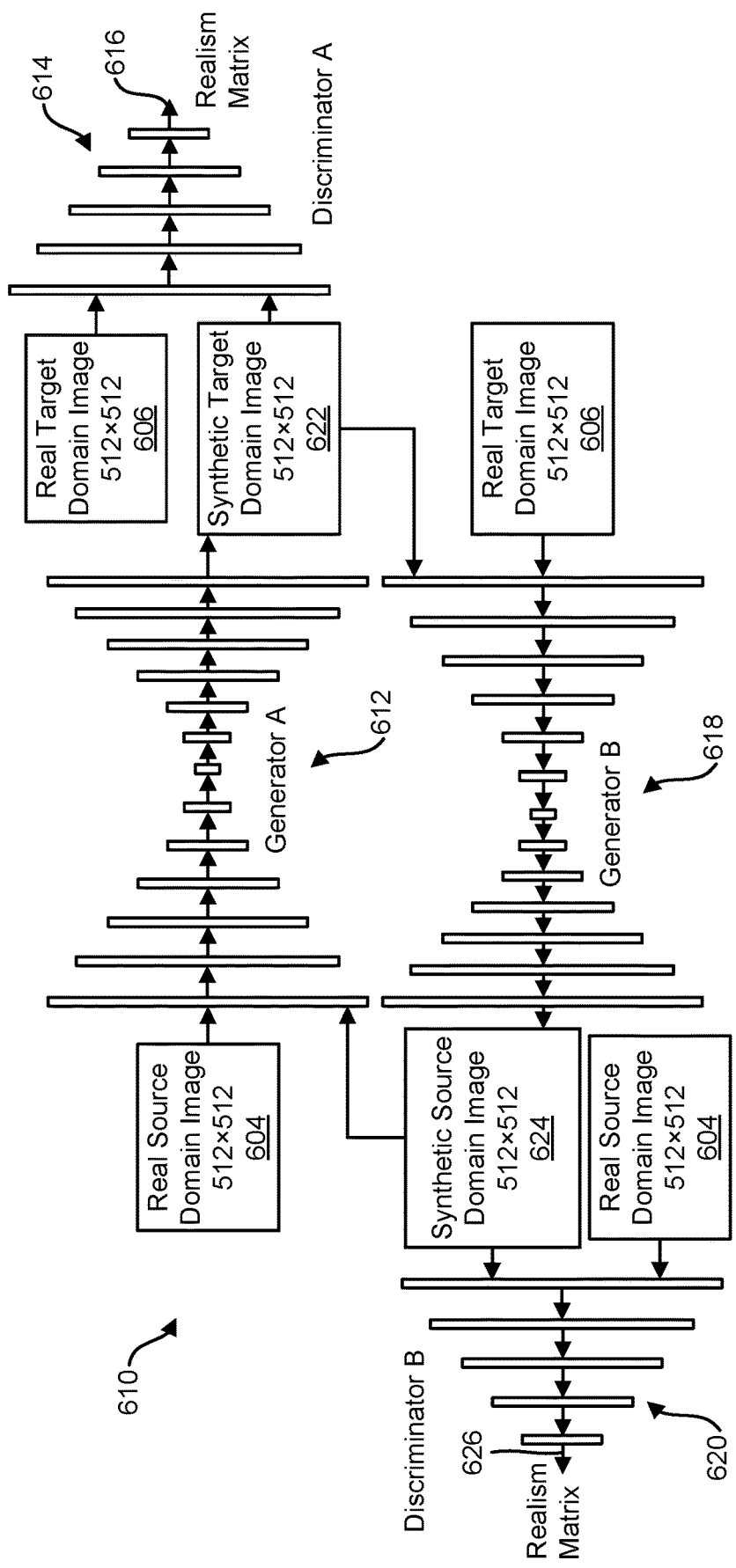
FIG. 6B is a schematic block diagram of a cyclic GAN for performing image domain transfer in accordance with an embodiment of the present invention.

FIG. 6A is a schematic block diagram of system 600 for performing image domain transfer in accordance with an embodiment of the present invention. FIG. 6B is a schematic block diagram of cyclic GAN for use with the system 600.

The system 600 may be used to train a machine learning model 610, e.g. a cyclic GAN, to transform an image obtained using one image modality to an image from another image modality. Examples of transforming between two-dimensional imaging modalities may include transforming between any two of the following: an X-ray, CBCT image, a slice of a CT scan, an intra-oral photograph, cephalometric, panoramic, or other two-dimensional imaging modality. In some embodiments, the machine learning model 610 may transform between any two of the following three-dimensional imaging modalities, such as a CT scan, magnetic resonance imaging (MM) image, a three-dimensional optical image, LIDAR (light detection and ranging) point cloud, or other three-dimensional imaging modality. In some embodiments, the machine learning model 610 may be trained to transform between any one of the two-dimensional imaging modalities and any one of the three-dimensional imaging modalities. In some embodiments, the machine learning model 610 may be trained to transform between any one of the three-dimensional imaging modalities and any one of the two-dimensional imaging modalities.

In some embodiments, the machine learning model 610 may be trained to translate between a first imaging modality that is subject to distortion (e.g., foreshortening or other type of optical distortion and a second imaging modality that is less subject to distortion. Deciphering dental pathologies on an image may be facilitated by establishing absolute measurements between anatomical landmarks (e.g., in a standard units of measurement, such as mm). Two-dimensional dental images interpret a three-dimensional space by estimating x-ray attenuation along a path from the target of an x-ray source to a photosensitive area of film or detector array. The relative size and corresponding lengths of any intercepting anatomy will be skewed as a function of their position relative to the x-ray source and imager. Furthermore, intra-oral optical dental images capture visual content by passively allowing scattered light to intercept a photosensitive detector array. Objects located further away from the detector array will appear smaller than closer objects, which makes estimating absolute distances difficult. Correcting for spatial distortion and image contamination can make deciphering dental pathologies and anatomy on x-ray, optical, or CBCT images more accurate. The machine learning model 610 may therefore be trained to translate between a distorted source domain and an undistorted target domain using unpaired dental images.

The transformation using the machine learning model 610 may be performed on an image that has been reoriented using the approach of FIG. 3 and/or had contamination removed using the approach of FIG. 5. Transformation using the machine learning model 610 may be performed to obtain a transformed image and the transformed image may then be used for subsequent processing according to some or all of steps 110, 112, and 114 of the method 100. Transformation using the machine learning model 610 may be performed as part of the preprocessing of step 108 of the method 100.

In the system 600, A training algorithm 602 takes as inputs images 604 from a source domain (first imaging modality, e.g., a distorted image domain) and images 606 from a target domain (second imaging modality, e.g., a non-distorted image domain or domain that is less distorted than the first domain). The images 604 and 606 are unpaired in some embodiments, meaning the images 606 are not transformed versions of the images 504 or paired such that an image 604 has a corresponding image 606 visualizing the same patient's anatomy. Instead, the images 506 may be selected from a repository of images and used to assess the transformation of the images 604 using the machine learning model 610. The training algorithm 502 may operate with respect to one or more loss functions 608 and modify a machine learning model 610 in order to reduce the loss functions 608 of the model 610.

FIG. 6B illustrates the machine learning model 610 embodied as a cyclic GAN, such as a densely-connected cycle consistent cyclic GAN (D-GAN). The cyclic GAN may include a generator 612 paired with a discriminator 614 and a second generator 618 paired with a second discriminator 620. The generators 612, 618 may be implemented using any of the approaches described above with respect to the generator 512. Likewise, the discriminators 614, 620 may be implemented using any of the approaches described above with respect to the discriminator 514.

Training of the machine learning model 610 may be performed by the training algorithm 602 as follows:

(Step 1) An image 604 in the source domain is input to generator 612 to obtain a synthetic image 622 in the target domain.

(Step 2) The synthetic image 622 and an unpaired image 606 from the target domain are input to the discriminator 614, which produces a realism matrix output 616 that is the discriminator's estimate as to which of the images 622, 606 is real.

(Step 3) Loss functions LF1 and LF2 are evaluated. Loss function LF1 is low when the output 616 indicates that the synthetic image 622 is real and that the target domain image 606 is fake. Since the output 616 is a matrix, the loss function LF1 may be a function of the multiple values (average, most frequently occurring value, etc.). Loss function LF2 is low when the output 616 indicates that the synthetic image 622 is fake and that the target domain image 606 is real. Thus, the generator 612 is trained to "fool" the discriminator 614 and the discriminator 614 is trained to detect fake images. The generator 612 and discriminator 614 may be trained concurrently.

(Step 4) The synthetic image 622 is input to the generator 618. The generator 618 transforms the synthetic image 622 into a synthetic source domain image 624.

(Step 5) A loss function LF3 is evaluated according to a comparison of the synthetic source domain image 624 and the source domain image 604 that was input to the generator 612 at Step 1. The loss function LF3 decreases with similarity of the images 604, 622.

(Step 6) A real target domain image 606 (which may be the same as or different from that input to the discriminator 614 at Step 2, is input to the generator 618 to obtain another synthetic source domain image 624. This synthetic source domain image 624 is input to the discriminator 620 along with a source domain image 604, which may be the same as or different from the source domain image 604 input to the generator 612 at Step 1.

(Step 7) The output 626 of the discriminator 620, which may be a realism matrix, is evaluated with respect to a loss function LF4 and a loss function LF5. Loss function LF4 is low when the output 626 indicates that the synthetic image 624 is real and that the source domain image 604 is fake. Since the output 626 is a matrix, the loss function LF4 may be a function of the multiple values (average, most frequently occurring value, etc.). Loss function LF5 is low when the output 626 indicates that the synthetic image 624 is fake and that the source domain image 604 is real.

(Step 8) The synthetic image 624 obtained at Step 6 is input to the generator 612 to obtain another synthetic target domain image 622.

(Step 9) A loss function LF6 is evaluated according to a comparison of the synthetic target domain image 622 from Step 8 and the target domain image 606 that was input to the generator 618 at Step 6. The loss function LF6 decreases with similarity of the images 606, 622.

(Step 10) Model parameters of the generators 612, 618 and the discriminators 614, 620 are tuned according to the outputs of the loss functions LF1, LF2, LF3, LF4, LF5, LF6, and LF7.

Steps 1 through 10 may be repeated until an ending condition is reached, such as when the discriminators 616, 620 can no longer distinguish between synthetic and real images (e.g., only correct 50 percent of the time), a Nash equilibrium is reached, or some other ending condition is reached.

Since the machine learning model 610 trains on un-paired images, a conventional L1 loss may be inadequate because the source and target domains are not spatially aligned. To promote spatial congruence between the source input image 604 and synthetic target image 622, the illustrated reverse GAN network (generator 618 and discriminator 620) may be used in combination with the illustrated forward GAN network (generator 612 and discriminator 614). Spatial congruence is therefore encouraged by evaluating L1 loss (loss function LF3) at Step 5 and evaluating L1 loss (loss function LF6) at Step 9.

Once training is ended, the generator 612 may be used to transform an input image in the source domain to obtain a transformed image in the target domain. The discriminators 616, 620 and the second generator 618 may be ignored or discarded during utilization.

The training algorithm 602 and utilization of the trained machine learning model 610 may be implemented using PYTORCH and AWS GPU instances in the same manner as described above with respect to FIG. 3.

In at least one possible embodiment, the system 600 operates on three-dimensional images, such as a CT, by replacing two-dimensional convolutional kernels (e.g., 4×4 and 1×1) with three-dimensional convolution kernels (e.g., 4×4×4 or 1×1×1).

Figure 7:
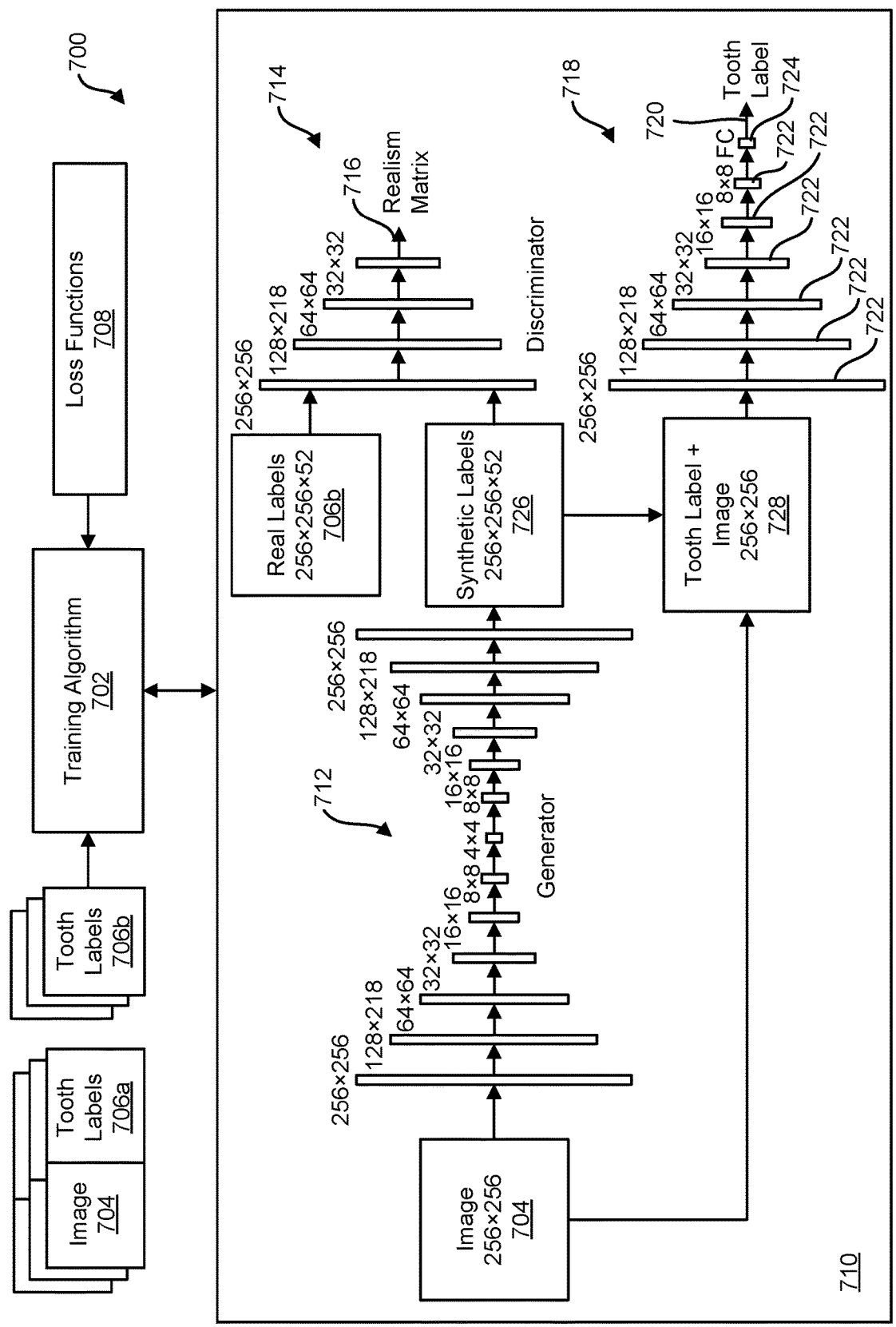
FIG. 7 is a schematic block diagram of a system for labeling teeth in an image in accordance with an embodiment of the present invention.

FIG. 7 is a schematic block diagram of system 700 for labeling teeth in accordance with an embodiment of the present invention. In order to establish the correct diagnosis and treatment protocol from dental images, it is often useful to first identify tooth labels. It can be challenging to correctly label teeth on abnormal anatomy because teeth might have caries, restorations, implants, or other characteristics that might hamper tooth identification. Furthermore, teeth might migrate and cause gaps between adjacent teeth or move to occupy gaps that resulted from extractions. The illustrated system 700 may utilizes adversarial loss and individual tooth level loss to label teeth in an image.

In the system 700, A training algorithm 702 takes as inputs training data entries that each include an image 704 and labels 706*a* for teeth represented in that image. For example, the labels 706*a* may be a tooth label mask in which pixel positions of the image 704 that correspond to a tooth are labeled as such, e.g. with the tooth number of a labeled tooth. The labels 706*a* for an image may be generated by a licensed dentist. The training algorithm 702 may further make use of unpaired labels 706*b*, i.e., pixels masks for images of real teeth, such as might be generated by a licensed dentist that do not correspond to the images 704 or labels 706*a*.

The training algorithm 702 may operate with respect to one or more loss functions 708 and modify a machine learning model 710 in order to train the machine learning model 710 to label teeth in a given input image. The labeling performed using the machine learning model 710 may be performed on an image that has been reoriented using the approach of FIG. 3 and had contamination removed using the approach of FIG. 5. In some embodiments, a machine learning model 710 may be trained for each view of the FMX such that the machine learning model 710 is used to label teeth in an image that has previously been classified using the approach of FIG. 4 as belonging to the FMX view for which the machine learning model 710 was trained.

In the illustrated embodiment, the machine learning model 710 includes a GAN including a generator 712 and a discriminator 714. The discriminator 714 may have an output 716 embodied as a realism matrix that may be implemented as for other realism matrices in other embodiments as described above. The output of the generator 712 may also be input to a classifier 718 trained to produce an output 720 embodied as a tooth label, e.g. pixel mask labeling a portion of an input image estimated to include a tooth.

As for other GAN disclosed herein, the generator 712 may include seven multi-scale stage deep encoder-decoder generator, such as using the approach described above with respect to the generator 512. For the machine learning model 710, the output channels of the generator 712 may be passed through a 1×1 convolutional layer as for the generator 512. However, the 1×1 convolution layer may further include a sigmoidal activation function to produce tooth labels. The generator 712 may likewise have stages of a different size than the generator 512, e.g., an input stage of 256×256 with downsampling by a factor of two between stages.

The discriminator 714 may be implemented using the approach described above for the discriminator 514. However, in the illustrated embodiment, the discriminator 514 includes four layers, though five layers as for the discriminator 514 may also be used.

The classifier 718 may be embodied as an encoder including six multi-scale stages 722 coupled to a fully connected layer 724, the output 720 of the fully connected layer 314 being a tooth label mask. In some embodiments, each multi-scale stage 722 may contain three 3×3 convolutional layers, which may be paired with batch-normalization and leaky rectified linear units (LeakyReLU). The first and last convolutional layers of each stage 722 may be concatenated via dense connections which help reduce redundancy within the CNN by propagating shallow information to deeper parts of the CNN. Each multi-scale network stage 722 may be downscaled by a factor of two at the end of each multi-scale stage 722 by convolutional downsampling.

Training of the machine learning model 710 may be performed by the training algorithm 702 according to the following method:

(Step 1) An image 704 is input to the generator 712, which outputs synthetic labels 726 for the teeth in the image 704. The synthetic labels 726 and unpaired tooth labels 706*b* from a repository are input to the discriminator 714. The discriminator 714 outputs a realism matrix with each value in the matrix being an estimate as to which of the input labels 726, 706*b* is real.

(Step 2) Input data 728 is input to the classifier 718, the input data 728 including layers including the original image 704 concatenated with the synthetic label 726 from Step 1. In response, the classifier 718 outputs its own synthetic label on its output 720.

(Step 3) The loss functions 708 are evaluated. This may include a loss function LF1 based on the realism matrix output at Step 1 such that the output of LF1 decreases with increase in the number of values of the realism matrix that indicate that the synthetic labels 726 are real. Step 3 may also include evaluating a loss function LF2 based on the realism matrix such that the output of LF2 decreases with increase in the number of values of the realism matrix that indicate that the synthetic labels 726 are fake. Step 3 may include evaluating a loss function LF3 based on a comparison of the synthetic label output by the classifier 718 and the tooth label 706*a* paired with the image 704 processed at Step 1. In particular, the output of the loss function LF3 may decrease with increasing similarity of the synthetic label output from the classifier 718 and the tooth label 706*a*.

(Step 4) The training algorithm 702 may use the output of loss function LF1 to tune parameters of the generator 712, the output of loss function LF2 to tune parameters of the discriminator 714, and the output of the loss function LF3 to tune parameters of the classifier 718. In some embodiments, the loss functions 708 are implemented as an objective function that utilizes a combination of softdice loss between the synthetic tooth label 726 and the paired truth tooth label 706a, adversarial loss from the discriminator 714, and categorical cross entropy loss from the classifier 718.

Steps 1 through 4 may be repeated such that the generator 712, discriminator 714, and classifier 718 are trained simultaneously. Steps 1 through 4 may continue to be repeated until an end condition is reached, such as until loss function LF3 meets a minimum value or other ending condition and LF2 is such that the discriminator 714 identifies the synthetic labels 726 as real 50 percent of the time or Nash equilibrium is reached.

During utilization, the discriminator 716 may be ignored or discarded. Images may then be processed by the generator 712 to obtain a synthetic label 726, which is then concatenated with the image to obtain data 728, which is then processed by the classifier 718 to obtain one or more tooth labels.

The training algorithm 702 and utilization of the trained machine learning model 710 may be implemented using PYTORCH and AWS GPU instances in the same manner as described above with respect to FIG. 3.

In at least one possible embodiment, the system 700 operates on three-dimensional images, such as a CT, by replacing two-dimensional convolutional kernels (e.g., 4×4 and 1×1) with three-dimensional convolution kernels (e.g., 4×4×4 or 1×1×1).

Figure 8:
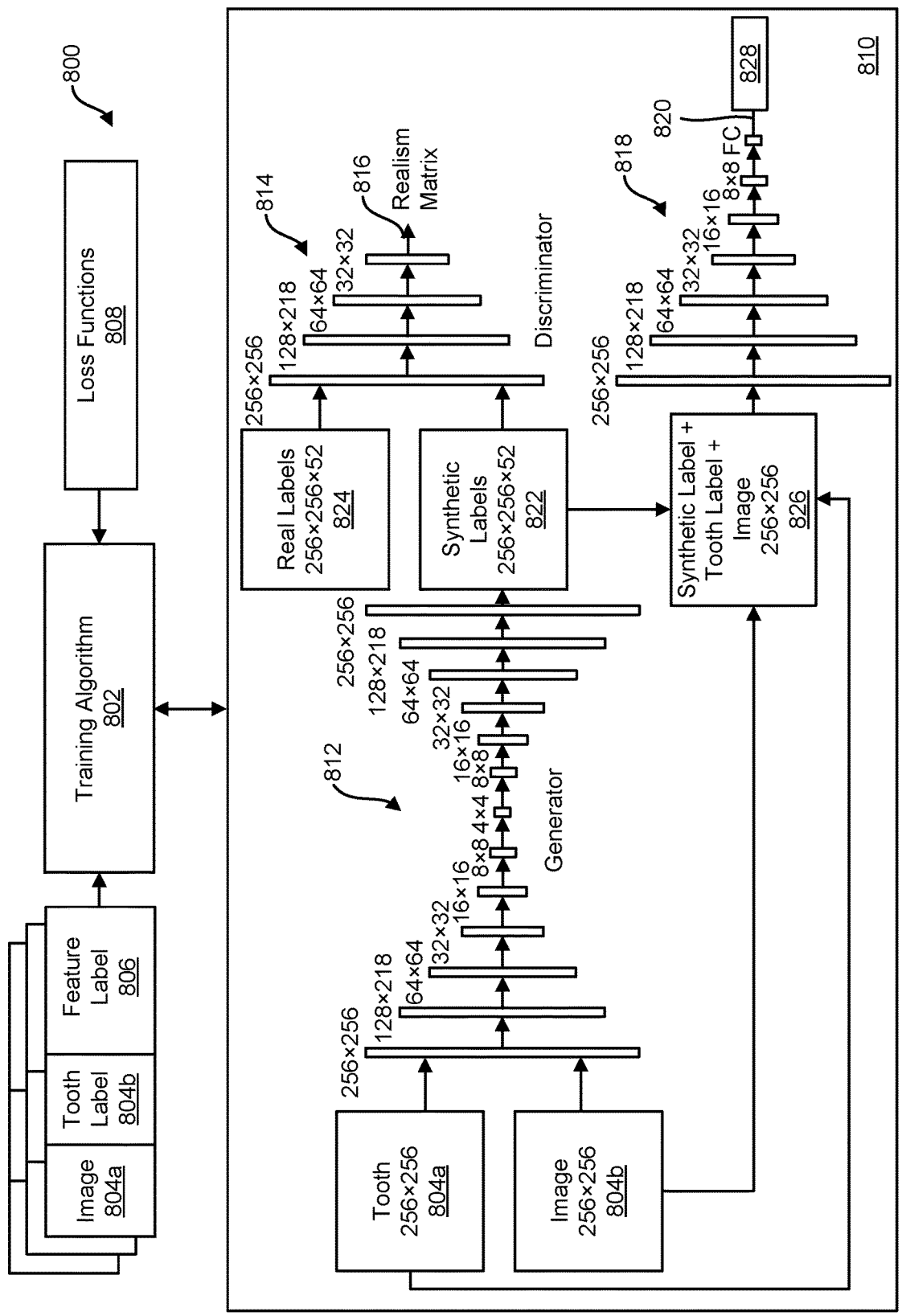
FIG. 8 is a schematic block diagram of a system for labeling periodontal features in an image in accordance with an embodiment of the present invention.

FIG. 8 is a schematic block diagram of system 800 for labeling features of teeth and surrounding areas in accordance with an embodiment of the present invention. For example, the system 800 may be used to label anatomical features such as the cementum enamel junction (CEJ), bony points on the maxilla or mandible that are relevant to the diagnosis of periodontal disease, gingival margin, junctional epithelium, or other anatomical feature.

In the system 800, A training algorithm 802 takes as inputs training data entries that each include an image 804a and labels 804b for teeth represented in that image, e.g., pixel masks indicating portions of the image 804a corresponding to teeth. The labels 804b for an image 804a may be generated by a licensed dentist or automatically generated using the tooth labeling system 700 of FIG. 7. Each training data entry may further include a feature label 806 that may be embodied as a pixel mask indicating pixels in the image 804a that correspond to an anatomical feature of interest. The image 804a may be an image that has been reoriented according to the approach of FIG. 3 and/or has had contamination removed using the approach of FIG. 4. In some embodiments, a machine learning model 810 may be trained for each view of the FMX such that the machine learning model 810 is used to label teeth in an image that has previously been classified using the approach of FIG. 4 as belonging to the FMX view for which the machine learning model 810 was trained.

As described below, two versions of the feature label 806 may be used. An non-dilated version is used in which only pixels identified as corresponding to the anatomical feature of interest are labeled. A dilated version is also used in which the pixels identified as corresponding to the anatomical feature of interest are dilated: a mask is generated that includes a probability distribution for each pixel rather than binary labels. Pixels that were labeled in the non-dilated version will have the highest probability values, but adjacent pixels will have probability values that decay with distance from the labeled pixels. The rate of decay may be according to a gaussian function or other distribution function. Dilation facilitates training of a machine learning model 810 since a loss function 808 will increase gradually with distance of inferred pixel locations from labeled pixel locations rather than being zero at the labeled pixel locations and the same non-zero value at every other pixel location.

The training algorithm 802 may operate with respect to one or more loss functions 808 and modify a machine learning model 810 in order to train the machine learning model 810 to label the anatomical feature of interest in a given input image. The labeling performed using the machine learning model 810 may be performed on an image that has been reoriented using the approach of FIG. 3 and had contamination removed using the approach of FIG. 5. In some embodiments, a machine learning model 810 may be trained for each view of the FMX such that the machine learning model 810 is used to label teeth in an image that has previously been classified using the approach of FIG. 4 as belonging to the FMX view for which the machine learning model 710 was trained. As noted above, the tooth labels 804b may be generated using the labeling approach of FIG. 8.

In the illustrated embodiment, the machine learning model 810 includes a GAN including a generator 812 and a discriminator 814. The discriminator 814 may have an output 816 embodied as a realism matrix that may be implemented as for other realism matrices in other embodiments as described above. The output of the generator 812 may also be input to a classifier 818 trained to produce an output 820 embodied as a label of the anatomical feature of interest, e.g. pixel mask labeling a portion of an input image estimated to correspond to the anatomical feature of interest. The generator 812 and discriminator 814 may be implemented according to the approach described above for the generator 712 and discriminator 714. The classifier 818 may be implemented according to the approach described above for the classifier 718.

Training of the machine learning model 810 may be performed by the training algorithm 802 as follows:

(Step 1). The image 804a and tooth label 804b are concatenated and input to the generator 812. Concatenation in this and other systems disclosed herein may include inputting two images (e.g., the image 804a and tooth label 804b) as different layers to the generator 812, such as in the same manner that different color values (red, green, blue) of a color image may be processed by a CNN according to any approach known in the art. The generator 812 may output synthetic labels 822 (e.g., pixel mask) of the anatomical feature of interest based on the image 804a and tooth label 804b.

(Step 2) The synthetic labels 822 and real labels 824 (e.g., an individual pixel mask from a repository including one or more labels) are then input to the discriminator 814. The real labels 824 are obtained by labeling the anatomical feature of interest in an image that is not paired with the image 804a from Step 1. The discriminator 814 produces a realism matrix at its output 816 with each value of the matrix indicating whether the synthetic label 822 is real or fake. In some embodiments, the real labels 824 may be real labels that have been dilated using the same approach used to dilate the feature labels 806 to obtain the dilated feature labels 806. In this manner, the generator 812 may be trained to generate dilated synthetic labels 822.

(Step 3) The image 804a, tooth label 804b, and synthetic labels 822 are concatenated to obtain a concatenated input 826, which is then input to the classifier 818. The classifier 818 processes the concatenated input 826 and produces output labels 828 (pixel mask) that is an estimate of the pixels in the image 804a that correspond to the anatomical feature of interest.

(Step 4) The loss functions 808 are evaluated with respect to the outputs of the generator 812, discriminator 814, and classifier 818. This may include evaluating a loss function LF1 based on the realism matrix output by the discriminator 814 at Step 2 such that the output of LF1 decreases with increase in the number of values of the realism matrix that indicate that the synthetic labels 822 are real. Step 4 may also include evaluating a loss function LF2 based on the realism matrix such that the output of LF2 decreases with increase in the number of values of the realism matrix that indicate that the synthetic labels 822 are fake. Step 4 may include evaluating a loss function LF3 based on a comparison of the synthetic label 822 output by the generator 812 and the dilated tooth feature label 806. In particular, the output of the loss function LF3 may decrease with increasing similarity of the synthetic label 822 and the dilated tooth label 804b. Step 4 may include evaluating a loss function LF4 based on a comparison of the synthetic labels 828 to the non-dilated tooth label 804b such that the output of the loss function LF4 decreases with increasing similarity of the synthetic labels 828 and the non-dilated tooth label 804b.

(Step 5) The training algorithm 802 may use the output of loss function LF1 and LF3 to tune parameters of the generator 812. In particular, the generator 812 may be tuned to both generate realistic labels according to LF1 and to generate a probability distribution of a dilated tooth label according to LF3. The training algorithm 802 may use the output of loss function LF2 to tune parameters of the discriminator 814 and the output of the loss function LF4 to tune parameters of the classifier 818.

Steps 1 through 5 may be repeated such that the generator 812, discriminator 814, and classifier 818 are trained simultaneously. Steps 1 through 5 may continue to be repeated until an end condition is reached, such as until loss functions LF1, LF3, and LF4 meet a minimum value or other ending condition, which may include the discriminator 714 identifying the synthetic label 822 as real 50 percent of the time or Nash equilibrium is reached.

The training algorithm 802 and utilization of the trained machine learning model 810 may be implemented using PYTORCH and AWS GPU instances in the same manner as described above with respect to FIG. 3.

In at least one possible embodiment, the system 800 operates on three-dimensional images, such as a CT, by replacing two-dimensional convolutional kernels (e.g., 4×4 and 1×1) with three-dimensional convolution kernels (e.g., 4×4×4 or 1×1×1).

During utilization to identify the anatomical feature of interest, the discriminator 814 may be ignored or discarded. Input images 804a with tooth labels 804b but without feature labels 806 are processed using the discriminator to obtain a synthetic labels 822.

The image 804a, tooth labels 804b, and synthetic labels 822 are concatenated and input to the classifier 818 that outputs a label 828 that is an estimate of the pixels corresponding to the anatomical feature of interest.

Below are example applications of the system 800 to label anatomical features:

In order to establish the correct diagnosis from dental images, it is often useful to identify the cementum enamel junction (CEJ). The CEJ can be difficult to identify in dental X-ray, CBCT, and intra-oral images because the enamel is not always clearly differentiated from dentin and the CEJ might be obfuscated by overlapping anatomy from adjacent teeth or improper patient setup and image acquisition geometry. To solve this problem, the system 800 may be used to identify the CEJ from images as the anatomical feature of interest.

In order to establish the correct diagnosis from dental images, it is often useful to identify the point on maxilla or mandible that correspond the periodontal disease. These boney points can be difficult to identify in dental x-ray, CBCT, and intra-oral images because the boney point is not always clearly differentiated from other parts of the bone and might be obfuscated by overlapping anatomy from adjacent teeth or improper patient setup and image acquisition geometry. To solve this problem, the system 800 may be used to identify the boney point as the anatomical feature of interest.

In order to establish the correct diagnosis from dental images, it is often useful to identify the gingival margin. This soft tissue point can be difficult to identify in dental X-ray, CBCT, and intra-oral images because the soft tissue point is not always clearly differentiated from other parts of the image and might be obfuscated by overlapping anatomy from adjacent teeth or improper patient setup and image acquisition geometry. To solve this problem, the system 800 may be used to identify the gingival margin as the anatomical feature of interest.

In order to establish the correct diagnosis from dental images, it is often useful to identify the junctional Epithelium (JM). This soft tissue point can be difficult to identify in dental X-ray, CBCT, and intra-oral images because the soft tissue point is not always clearly differentiated from other parts of the image and might be obfuscated by overlapping anatomy from adjacent teeth or improper patient setup and image acquisition geometry. To solve this problem, the system 800 may be used to identify the JE as the anatomical feature of interest.

Figure 9:
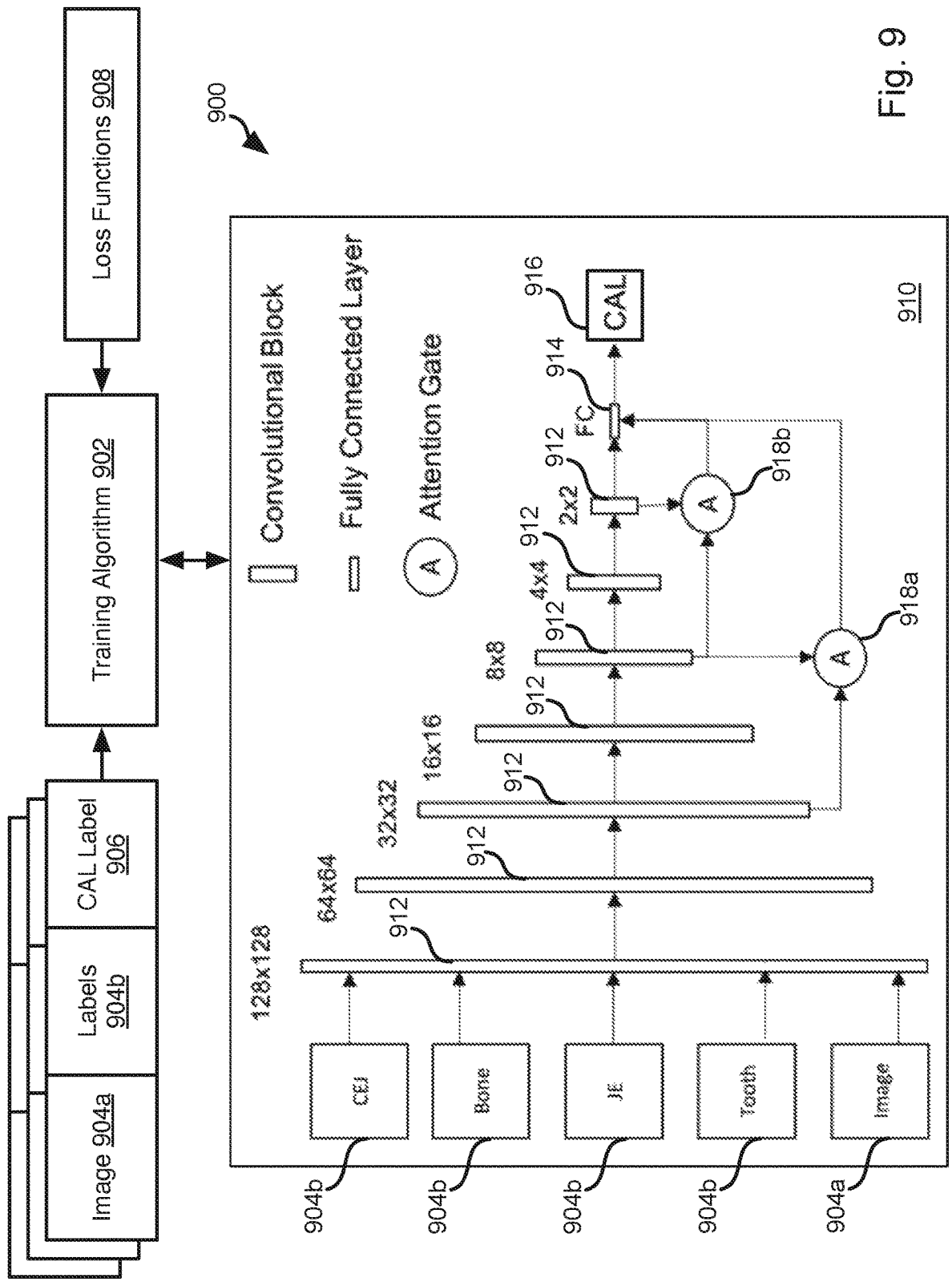
FIG. 9 is a schematic block diagram of a system for determining clinical attachment level (CAL) in accordance with an embodiment of the present invention.

FIG. 9 is a schematic block diagram of system 900 for determining clinical attachment level (CAL) in accordance with an embodiment of the present invention. In order to establish the correct periodontal diagnosis from dental images, it is often useful to identify the clinical attachment level (CAL). CAL can be difficult to identify in dental x-ray, CBCT, and intra-oral images because CAL relates to the cementum enamel junction (CEJ), probing depth, junctional epithelium (JE), and boney point (B) on the maxilla or mandible which might not always be visible. Furthermore, the contrast of soft tissue anatomy can be washed out from adjacent boney anatomy because bone attenuates more x-rays than soft tissue. Also, boney anatomy might not always be differentiated from other parts of the image or might be obfuscated by overlapping anatomy from adjacent teeth or improper patient setup and image acquisition geometry. The illustrated system 900 may therefore be used to determine CAL.

In the system 900, A training algorithm 802 takes as inputs training data entries that each include an image 904a and labels 904b, e.g., pixel masks indicating portions of the image 904a corresponding to teeth, CEJ, JE, B, or other anatomical features. The labels 904b for an image 904a may be generated by a licensed dentist or automatically generated using the tooth labeling system 700 of FIG. 7 and/or the labeling system 800 of FIG. 8. The image 904a may have been one or both of reoriented according to the approach of FIG. 3 decontaminated according to the approach of FIG. 5.

In some embodiments, a machine learning model 910 may be trained for each view of the FMX such that the machine learning model 910 is used to label teeth in an image that has previously been classified using the approach of FIG. 4 as belonging to the FMX view for which the machine learning model 910 was trained.

Each training data entry may further include a CAL label 906 that may be embodied as a numerical value indicating the CAL for a tooth, or each tooth of a plurality of teeth, represented in the image. The CAL label 906 may be assigned to the tooth or teeth of the image by a licensed dentist.

The training algorithm 902 may operate with respect to one or more loss functions 908 and modify a machine learning model 910 in order to train the machine learning model 910 to determine one or more CAL values for one or more teeth represented in an input image.

In the illustrated embodiment, the machine learning model 910 is a CNN including seven multi-scale stages 912 followed by a fully connected layer 914 that outputs a CAL estimate 916, such as a CAL estimate 916 for each tooth identified in the labels 904b. Each multi-scale stage 912 may contain three 3×3 convolutional layers, paired with batchnormalization and leaky rectified linear units (LeakyReLU). The first and last convolutional layers of each stage 912 may be concatenated via dense connections which help reduce redundancy within the network by propagating shallow information to deeper parts of the network. Each multi-scale stage 912 may be downscaled by a factor of two at the end of each multi-scale stage by convolutional downsampling with stride 2. The third and fifth multi-scale stages 912 may be passed through attention gates 918a, 918b before being concatenated with the last multi-scale stage 912. The attention gate 918a applied to the third stage 912 may be gated by a gating signal derived from the fifth stage 912. The attention gate 918b applied to the fifth stage 912 may be gated by a gating signal derived from the seventh stage 912. Not all regions of the image are relevant for estimating CAL, so attention gates 918a, 918b may be used to selectively propagate semantically meaningful information to deeper parts of the network. Adam optimization may be used during training which automatically estimates the lower order moments and helps estimate the step size which desensitizes the training routine to the initial learning rate.

A training cycle of the training algorithm 902 may include concatenating the image 904a with the labels 904b of a training data entry and processing the concatenated data with the machine learning model 910 to obtain a CAL estimate 916. The CAL estimate 916 is compared to the CAL label 906 using the loss function 908 to obtain an output, such that the output of the loss function decreases with increasing similarity between the CAL estimate 916 and the CAL label 906. The training algorithm 902 may then adjust the parameters of the machine learning model 910 according to the output of the loss function 908. Training cycles may be repeated until an ending condition is reached, such as the loss function 908 reaching a minimum value or other ending condition being achieved.

The training algorithm 902 and utilization of the trained machine learning model 810 may be implemented using PYTORCH and AWS GPU instances in the same manner as described above with respect to FIG. 3.

In at least one possible embodiment, the system 900 operates on three-dimensional images, such as a CT, by replacing two-dimensional convolutional kernels (e.g., 3×3 and 1×1) with three-dimensional convolution kernels (e.g., 3×3×3 or 1×1×1).

Figure 10:
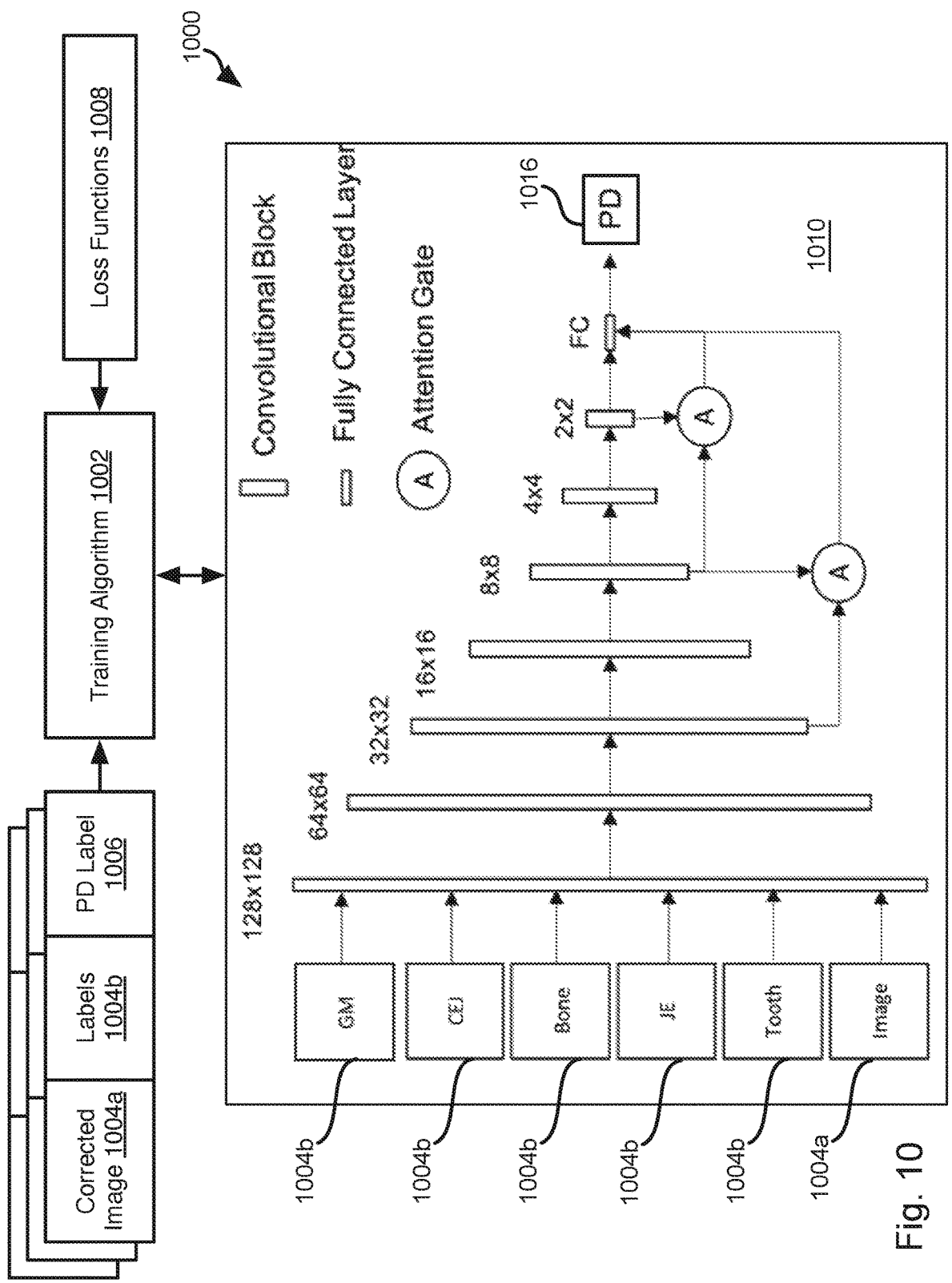
FIG. 10 is a schematic block diagram of a system for determining pocket depth (PD) in accordance with an embodiment of the present invention.

FIG. 10 is a system 1000 for determining pocket depth (PD) in accordance with an embodiment of the present invention. In order to establish the correct periodontal diagnosis from dental images, it is often useful to identify the pocket depth (PD). PD can be difficult to identify in dental X-ray, CBCT, and intra-oral images because PD relates to the cementum enamel junction (CEJ), junctional epithelium (JE), gingival margin (GM), and boney point (B) on the maxilla or mandible which might not always be visible. Furthermore, the contrast of soft tissue anatomy can be washed out from adjacent boney anatomy because bone attenuates more x-rays than soft tissue. Also, boney anatomy might not always be differentiated from other parts of the image or might be obfuscated by overlapping anatomy from adjacent teeth or improper patient setup and image acquisition geometry. The illustrated system 1000 may therefore be used to determine PD.

In the system 1000, a training algorithm 1002 takes as inputs training data entries that each include an image 1004a and labels 1004b, e.g., pixel masks indicating portions of the image 1004a corresponding to teeth, GM, CEJ, JE, B, or other anatomical features. The labels 1004b for an image 1004a may be generated by a licensed dentist or automatically generated using the tooth labeling system 700 of FIG. 7 and/or the labeling system 800 of FIG. 8. Each training data entry may further include a PD label 1006 that may be embodied as a numerical value indicating the pocket depth for a tooth, or each tooth of a plurality of teeth, represented in the image. The PD label 1006 may be assigned to the tooth or teeth of the image by a licensed dentist.

The image 1004a may have been one or both of reoriented according to the approach of FIG. 3 decontaminated according to the approach of FIG. 5. In some embodiments, a machine learning model 1010 may be trained for each view of the FMX such that the machine learning model 1010 is used to label teeth in an image that has previously been classified using the approach of FIG. 4 as belonging to the FMX view for which the machine learning model 1010 was trained.

The training algorithm 1002 may operate with respect to one or more loss functions 1008 and modify a machine learning model 1010 in order to train the machine learning model 1010 to determine one or more PD values for one or more teeth represented in an input image. In the illustrated embodiment, the machine learning model 1010 is a CNN that may be configured as described above with respect to the machine learning model 910.

A training cycle of the training algorithm 1002 may include concatenating the image 1004a with the labels 1004b of a training data entry and processing the concatenated data with the machine learning model 1010 to obtain a PD estimate 1016. The PD estimate 1016 is compared to the PD label 1006 using the loss function 1008 to obtain an output, such that the output of the loss function decreases with increasing similarity between the PD estimate 1016 and the PD label 1006. The training algorithm 1002 may then adjust the parameters of the machine learning model 1010 according to the output of the loss function 1008. Training cycles may be repeated until an ending condition is reached, such as the loss function 1008 reaching a minimum value or other ending condition being achieved.

The training algorithm 1002 and utilization of the trained machine learning model 1010 may be implemented using PYTORCH and AWS GPU instances in the same manner as described above with respect to FIG. 3.

In at least one possible embodiment, the system 1000 operates on three-dimensional images, such as a CT, by replacing two-dimensional convolutional kernels (e.g., 3×3 and 1×1) with three-dimensional convolution kernels (e.g., 3×3×3 or 1×1×1).

Figure 11:
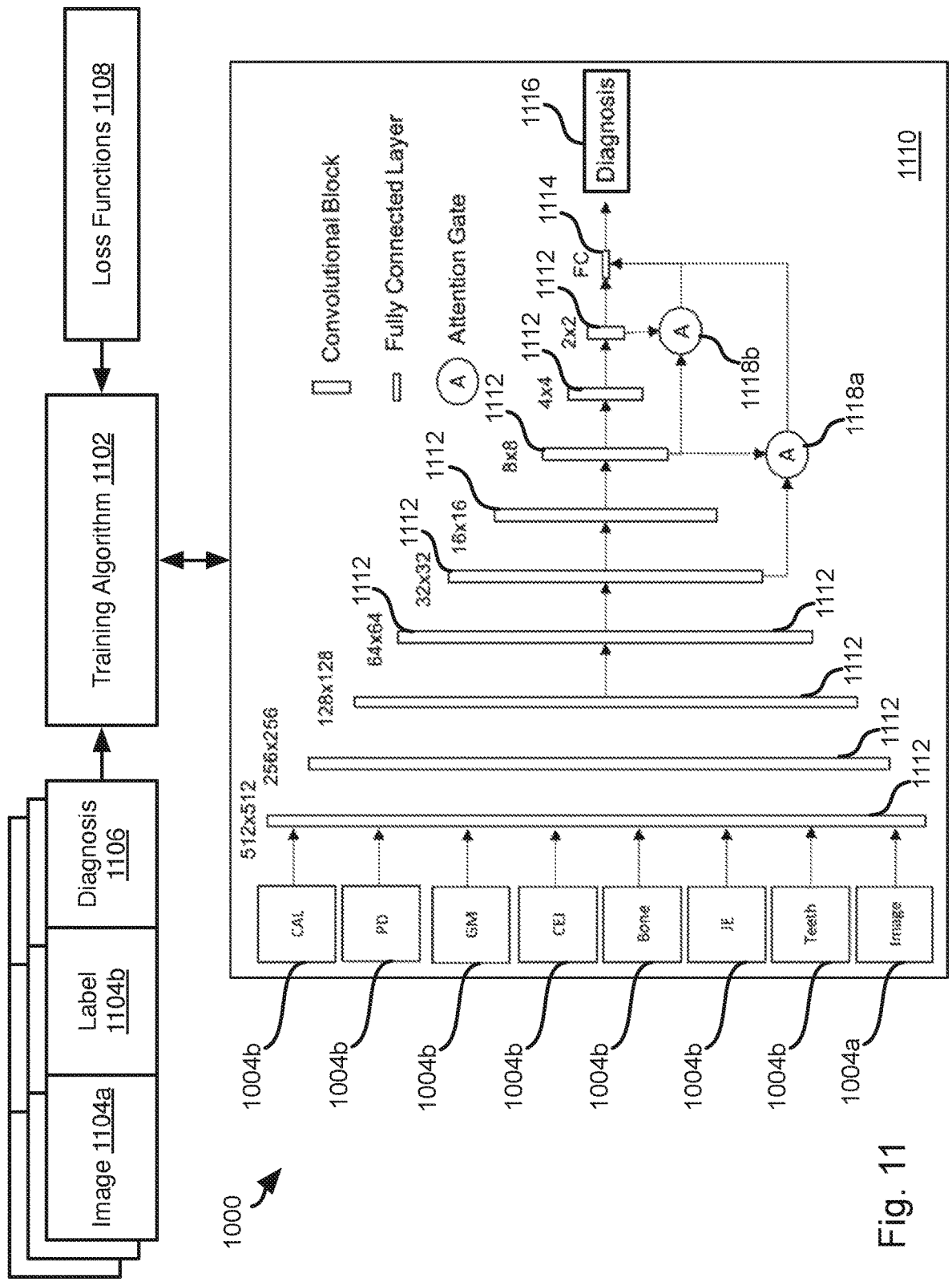
FIG. 11 is a schematic block diagram of a system for determining a periodontal diagnosis in accordance with an embodiment of the present invention.

FIG. 11 is a schematic block diagram of a system 1100 for determining a periodontal diagnosis in accordance with an embodiment of the present invention. The system 1100 may be used as part of step 114 of the method 100 in order to diagnose a condition that may trigger evaluation of a decision hierarchy. For example, if the machine learning model discussed below indicates that a diagnosis is appropriate, the condition of step 116 of the method 100 may be deemed to be satisfied.

In order to assess the extent of periodontal disease it is often useful to observe a multitude of dental images. Periodontal disease can be difficult to diagnosis on dental X-rays, CBCTs, and intra-oral images because periodontal disease relates to the cementum enamel junction (CEJ), junctional epithelium (JE), gingival margin (GM), boney point (B) on the maxilla or mandible, pocket depth (PD), gingival health, comorbidities, and clinical attachment level (CAL), which might not always be available. Furthermore, the contrast of soft tissue anatomy can be washed out from adjacent boney anatomy because bone attenuates more x-rays than soft tissue. Also, boney anatomy might not always be differentiated from other parts of the image or might be obfuscated by overlapping anatomy from adjacent teeth or improper patient setup and image acquisition geometry. To solve this problem, the illustrated system 1100 may be used in combination with the approaches of FIGS. 7 through 10 in order to derive a comprehensive periodontal diagnosis. The system 1100 may take advantage of an ensemble of unstructured imaging data and structured data elements derived from tooth masks, CEJ points, GM points, JE information, bone level points. All of this information may be input into the system 1000 and non-linearly combined via a machine learning model 1110.

For compatibility, all structured information (e.g. pixel mask labels, PD, and CAL values obtained using the approaches of FIGS. 7 through 10) may be converted to binary matrices and concatenated with the raw imaging data used to derive the structured information into a single n-dimensional array. Each image processed using the system 1100 may be normalized by the population mean and standard deviation of an image repository, such as a repository of images used for the unpaired images in the approach of FIGS. 5, 6A, 6B, 7, and 8 or some other repository of images.

In the system 1100, A training algorithm 1102 takes as inputs training data entries that each include an image 1104a and labels 1104b, e.g., pixel masks indicating portions of the image 1104a corresponding to teeth, GM, CEJ, JE, B or other anatomical features. Each training data entry may further include a diagnosis 1106, i.e. a periodontal diagnosis that was determined by a licensed dentist to be appropriate for one or more teeth represented in the image 1104a.

The image 1104a may be an image that has been oriented according to the approach of FIG. 3 and had decontaminated according to the approach of FIG. 4. In some embodiments, a machine learning model 1110 may be trained for each view of the FMX such that the machine learning model 1110 is used to label teeth in an image that has previously been classified using the approach of FIG. 4 as belonging to the FMX view for which the machine learning model 1110 was trained.

The labels 1104b for the image 1104a of a training data entry may be generated by a licensed dentist or automatically generated using the tooth labeling system 700 of FIG. 7 and/or the labeling system 800 of FIG. 8. The labels 1104b for a tooth represented in an image 1104a may further be labeled with a CAL value and/or a PD value, such as determined using the approaches of FIGS. 9 and 10 or by a licensed dentist. The CAL and/or PD labels may each be implemented as a pixel mask corresponding to the pixels representing a tooth and associated with the CAL value and PD value, respectively, determined for that tooth.

In some embodiments, other labels 1104b may be used. For example, a label 1104b may label a tooth in an image with a pixel mask indicating a past treatment with respect to that tooth. Other labels 1104b may indicate comorbidities of the patient represented in the image 1104a.

The training algorithm 1102 may operate with respect to one or more loss functions 1108 and modify a machine learning model 1110 in order to train the machine learning model 1110 to determine a predicted diagnosis for one or more teeth represented in an input image.

In the illustrated embodiment, the machine learning model 1110 includes nine multi-scale stages 1112 followed by a fully connected layer 1114 that outputs a predicted diagnosis 1116. Each multi-scale stage 1112 may contain three 3×3 convolutional layers, paired with batchnormalization and leaky rectified linear units (LeakyReLU). The first and last convolutional layers of each stage 1112 may be concatenated via dense connections which help reduce redundancy within the network by propagating shallow information to deeper parts of the network. Each multi-scale stage 1112 may be downscaled by a factor of two at the end of each multi-scale stage 1112, such as by convolutional downsampling with stride 2. The fifth and seventh multi-scale stages 1112 may be passed through attention gates 1118a, 1118b before being concatenated with the last stage 1112. The attention gate 1118a may be applied to the fifth stage 1112 according to a gating signal derived from the seventh stage 1112. The attention gate 1118b may be applied to the seventh stage 1112 according to a gating signal derived from the ninth stage 1112. Not all regions of the image are relevant for estimating periodontal diagnosis, so attention gates may be used to selectively propagate semantically meaningful information to deeper parts of the network. Adam optimization may be used during training which automatically estimates the lower order moments and helps estimate the step size which desensitizes the training routine to the initial learning rate.

A training cycle of the training algorithm 1102 may include concatenating the image 1104a with the labels 1104b of a training data entry and processing the concatenated data with the machine learning model 1110 to obtain a predicted diagnosis 1116. The predicted diagnosis is compared to the diagnosis 1106 using the loss function 1108 to obtain an output, such that the output of the loss function decreases with increasing similarity between the diagnosis 1116 and the diagnosis 1106, which may simply be a binary value (zero of correct, non-zero if not correct). The training algorithm 1102 may then adjust the parameters of the machine learning model 1110 according to the output of the loss function 1108. Training cycles may be repeated until an ending condition is reached, such as the loss function 1108 reaching a minimum value or other ending condition being achieved.

The training algorithm 1102 and utilization of the trained machine learning model 1110 may be implemented using PYTORCH and AWS GPU instances in the same manner as described above with respect to FIG. 3.

In at least one possible embodiment, the system 1100 operates on three-dimensional images, such as a CT, by replacing two-dimensional convolutional kernels (e.g., 3×3 and 1×1) with three-dimensional convolution kernels (e.g., 3×3×3 or 1×1×1).

In another variation, several outputs from multiple image modalities or multiple images from a single modality are combined in an ensemble of networks to form a comprehensive periodontal diagnosis or treatment protocol. For example, a system 1100 may be implemented for each imaging modality of a plurality of imaging modalities. A plurality of images of the same patient anatomy according to the plurality of imaging modalities may then be labeled and processed according to their corresponding systems 1100. The diagnosis output for each imaging modality may then be unified to obtain a combined diagnosis, such as by boosting, bagging, or other conventional machine learning methods such as random forests, gradient boosting, or support vector machines (SVMs).

Figure 12:
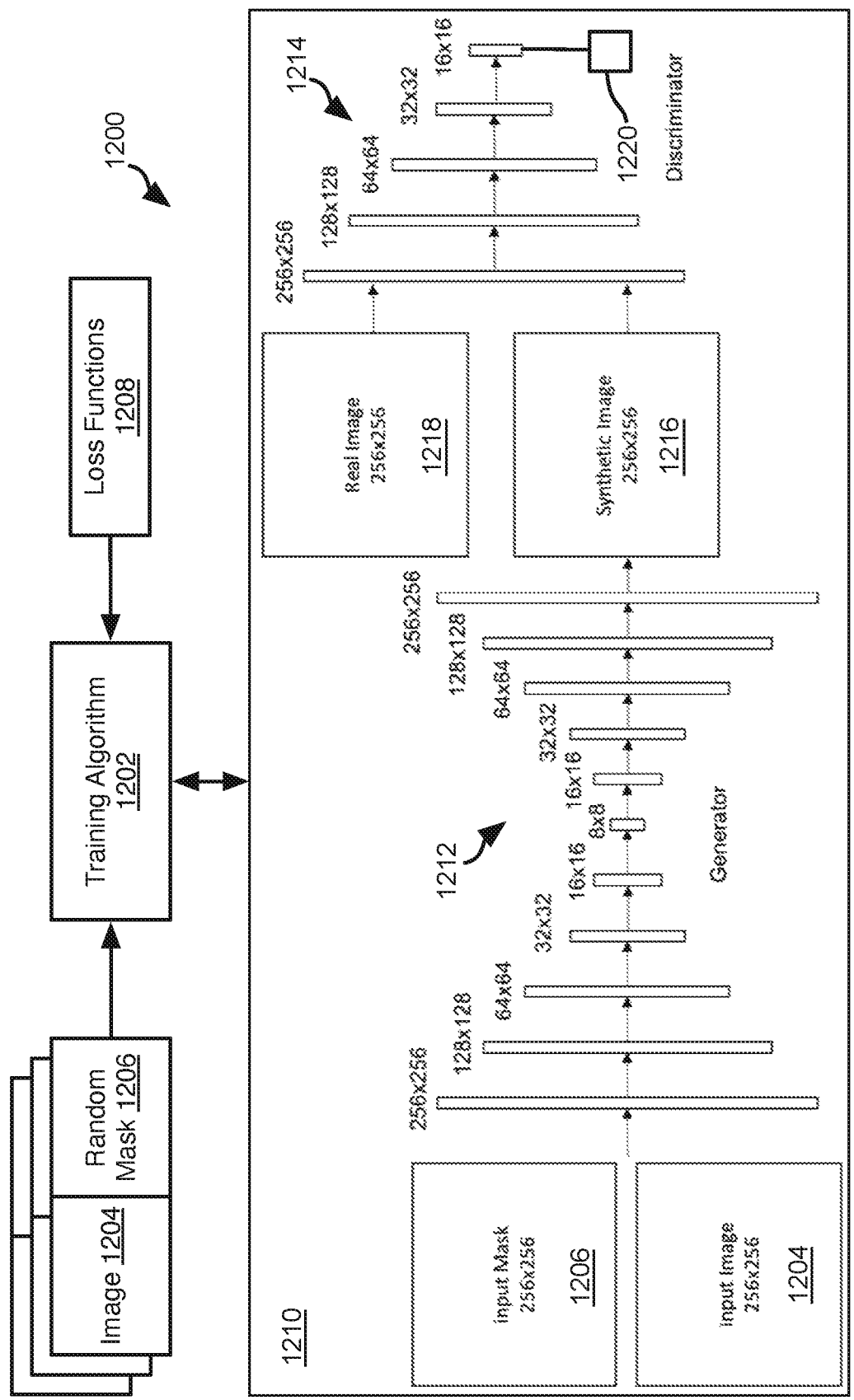
FIG. 12 is a schematic block diagram of a system for restoring missing data in images in accordance with an embodiment of the present invention.

FIG. 12 is a schematic block diagram of a system 1200 for restoring missing data to images in accordance with an embodiment of the present invention. It is often difficult to assess the extent of periodontal disease or determine orthodontic information from a dental image, such as intra-oral photos, X-rays, panoramic, or CBCT images. Sometimes the images do not capture the full extent of dental anatomy necessary to render diagnostic or treatment decisions. Furthermore, sometimes patient sensitive information needs to be removed from an image and filled in with missing synthetic information so that it is suitable for a downstream deep learning model. The system 1200 provides an inpainting system that utilizes partial convolutions, adversarial loss, and perceptual loss. The inpainting system 1200 is particularly useful for restoring missing portions of images to facilitate the identification of caries.

The system 1200 may be used to train a machine learning model to restore missing data to images for use in preprocessing an image at step 108 of the method 100. In some embodiment, missing data may be restored to an image using the approach of FIG. 12 to obtain a corrected image and the corrected image may then be reoriented using the approach of FIG. 3 to obtain a reoriented image (though the image output from the approach of FIG. 3 may not always be rotated relative to the input image). Decontamination according to the approach of FIG. 5 may be performed and may be performed on an image either before or after missing data is restored to it according to the approach of FIG. 12.

In the system 1200, A training algorithm 1202 is trained using training data entries including an image 1204 and a randomly generated mask 1206 that defines portions of the image 1204 that are to be removed and which a machine learning model 1210 is to attempt to restore. As for other embodiments, the image 1204 of each training data entry may be according to any of the imaging modalities described herein. The training algorithm 1202 may operate with respect to one or more loss functions 1208 and modify the machine learning model 1210 in order to reduce the loss functions 1208 of the model 1210.

In the illustrated embodiment, the machine learning model 1210 is GAN including a generator 1212 and a discriminator 1214. The generator 1212 and discriminator may be implemented according to any of the approaches described above with respect to the generators 512, 612, 618, 712, 812 and discriminators 514, 614, 620, 714, 814 described above.

Training cycles of the machine learning model 1210 may include inputting the image 1204 and the random mask 1206 of a training data entry into the generator 1212. The mask 1206 may be a binary mask, with one pixel for each pixel in the image. The value of a pixel in the binary mask may be zero where that pixel is to be omitted from the image 1204 and a one where the pixel of the image 1204 is to be retained. The image as input to the generator 1212 may be a combination of the image 1204 and mask 1206, e.g. the image 1204 with the pixels indicated by the mask 1206 removed, i.e. replaced with random values or filled with a default color value.

The generator 1212 may be trained to output a reconstructed synthetic image 1216 that attempts to fill in the missing information in regions indicated by the mask 1206 with synthetic imaging content. In some embodiments, the generator 1212 learns to predict the missing anatomical information based on the displayed sparse anatomy in the input image 1204. To accomplish this the generator 1212 may utilize partial convolutions that only propagate information through the network that is near the missing information indicated by the mask 1206. In some embodiments, the binary mask 1206 of the missing information may be expanded at each convolutional layer of the network by one in all directions along all spatial dimensions.

In some embodiments, the generator 1212 is a six multi-scale stage deep encoder-decoder generator and the discriminator 124 is a five multi-scale level deep discriminator. Each convolutional layer within the encoder and decoder stage of the generator 1212 may uses 4×4 partial convolutions paired with batchnormalization and rectified linear unit (ReLU) activations. Convolutional downsampling may be used to downsample each multi-scale stage and transpose convolutions may be used to incrementally restore the original resolution of the input signal. The resulting high-resolution output channels may be passed through a 1×1 convolutional layer and hyperbolic tangent activation function to produce the synthetic reconstructed image 1216.

At each iteration, the synthetic image 1216 and a real image 1218 from a repository may be passed through the discriminator 1214, which outputs a realism matrix 1220 in which each value of the realism matrix 1220 is a value indicating which of the images 1216, 1218 is real.

The loss functions 1208 may be implementing using weighted L1 loss between the synthetic image 1216 and input image 1204 without masking. In some embodiments, the loss functions 1208 may further evaluate perceptual loss from the last three stages of the discriminator 1214, style loss based on the Gram matrix of the extracted features from the last three stages of the discriminator, and total variation loss. The discriminator 1214 may be pretrained in some embodiments such that it is not updated during training and only the generator 1212 is trained. In other embodiments, the generator 1212 and discriminator 1214 may be trained simultaneously until the discriminator 1214 can no longer differentiate between synthetic and real images or a Nash equilibrium has been reached.

During utilization, the discriminator 1214 may be discarded or ignored. An image to be reconstructed may be processed using the generator 1212. In some embodiments, a mask of the image may also be input as for the training phase. This mask may be generated by a human or automatically and may identify those portions of the image that are to be reconstructed. The output of the generator 1214 after this processing will be a synthetic image in which the missing portions have been filled in.

In some embodiments, multiple images from multiple image modalities or multiple images from a single modality may combined in an ensemble of networks to form a comprehensive synthetic reconstructed image. For example, each image may be processed using a generator 1214 (which may be trained using images of the imaging modality of the each image in the case of multiple imaging modalities) and the output of the generators 1214 may then be combined. The outputs may be combined by boosting, bagging, or other conventional machine learning methods such as random forests, gradient boosting, or state vector machines (SVMs).

In at least one possible embodiment, the system 1200 may operate on three-dimensional images 1204, such as a CT scan. This may include replacing the 4×4 convolutional kernels with 4×4×4 convolutional kernels and replacing the 1×1 convolutional kernels with 1×1×1 convolutional kernels.

The training algorithm 1202 and utilization of the trained machine learning model 1210 may be implemented using PYTORCH and AWS GPU instances in the same manner as described above with respect to FIG. 3.

In at least one possible embodiment, the system 1200 operates on three-dimensional images, such as a CT, by replacing two-dimensional convolutional kernels (e.g., 4×4 and 1×1) with three-dimensional convolution kernels (e.g., 4×4×4 or 1×1×1).

Referring generally to FIGS. 3 through 12, the machine learning models that are illustrated and discussed above are represented as CNNs. Additionally, specific CNN configurations are shown and discussed. It shall be understood that, although both a CNN generally and the specific configuration of a CNN shown and described may be useful and well suited to the tasks ascribed to them, other configurations of a CNN and other types of machine learning models may also be trained to perform the automation of tasks described above. In particular a neural network or deep neural network (DNN) according to any approach known in the art may also be used to perform the automation of tasks described above.

Referring to FIGS. 13 through 18, deep learning-based computer vision is being rapidly adopted to solve many problems in healthcare. However, an adversarial attack may probe a model and find a minimum perturbation to the input image that causes maximum degradation of the deep learning model, while simultaneously maintaining the perceived image integrity of the input image.

In dentistry, adversarial attacks can be used to create malicious examples that compromise the diagnostic integrity of automated dental image classification, landmark detection, distortion correction, image transformation, text extraction, object detection, image denoising, or segmentation models. Additionally, images might be manually tampered with in photoshop or other image manipulation software to fool a clinician into incorrectly diagnosing disease Adversarial attacks have highlighted cyber security threats to current deep learning models. Similarly, adversarial attacks on medical automation systems could have disastrous consequences to patient care. Because many industries are increasingly reliant on deep learning automation solutions, adversarial defense and detection systems have become a critical domain in the machine learning community.

There are two main types of adversarial defense approaches. One approach uses a screening algorithm to detect if an image is authentic and the other approach builds models that are robust against adversarial images. The quality of the defense system is dependent on the ability to create high quality adversarial examples.

To produce adversarial examples, attackers need to gain access to the system. Black box attacks assume no knowledge of model parameters or architecture. Grey box attacks have architectural information but have no knowledge of model parameters. White box attacks have a priori knowledge of model parameters and architecture. White box adversarial examples may be used to evaluate the defense of each model, since white box attacks are the most powerful.

For white box attacks, an adversarial attacking system may be implemented by building attacks directly on each victim model. In some embodiments, the attack system uses a novel variation of the projected gradient decent (PGD) method (Madry Kurakin), which is an iterative extension of the canonical fast gradient sign method (Goodfellow). PGD finds the optimal perturbation by performing a projected stochastic gradient descent on the negative loss function.

For grey box attacks, an adversarial attacking system may be implemented by building attacks on the output of each victim model. Since grey box attacks do not have access to the gradients of the model, the output of each victim model may be used to update the gradients of the attacking model. The attacking model therefore becomes progressively better at fooling the victim model through stochastic gradient decent.

For black box attacks, an adversarial attacking system may be implemented by building attacks on the output of many victim models. Since black box attacks do not have access to the gradients of any model, the output of many victim models are used to update the gradients of the attacking model. The attacking model therefore becomes progressively better at fooling the victim model through stochastic gradient decent.

The systems disclosed herein may use adaptation of a coevolving attack and defense mechanism. After each epoch in the training routine, new adversarial examples may be generated and inserted into the training set. The defense mechanism is therefore trained to be progressively better at accurate inference in the presence of adversarial perturbations and the attack system adapts to the improved defense of the updated model.

Figure 13:
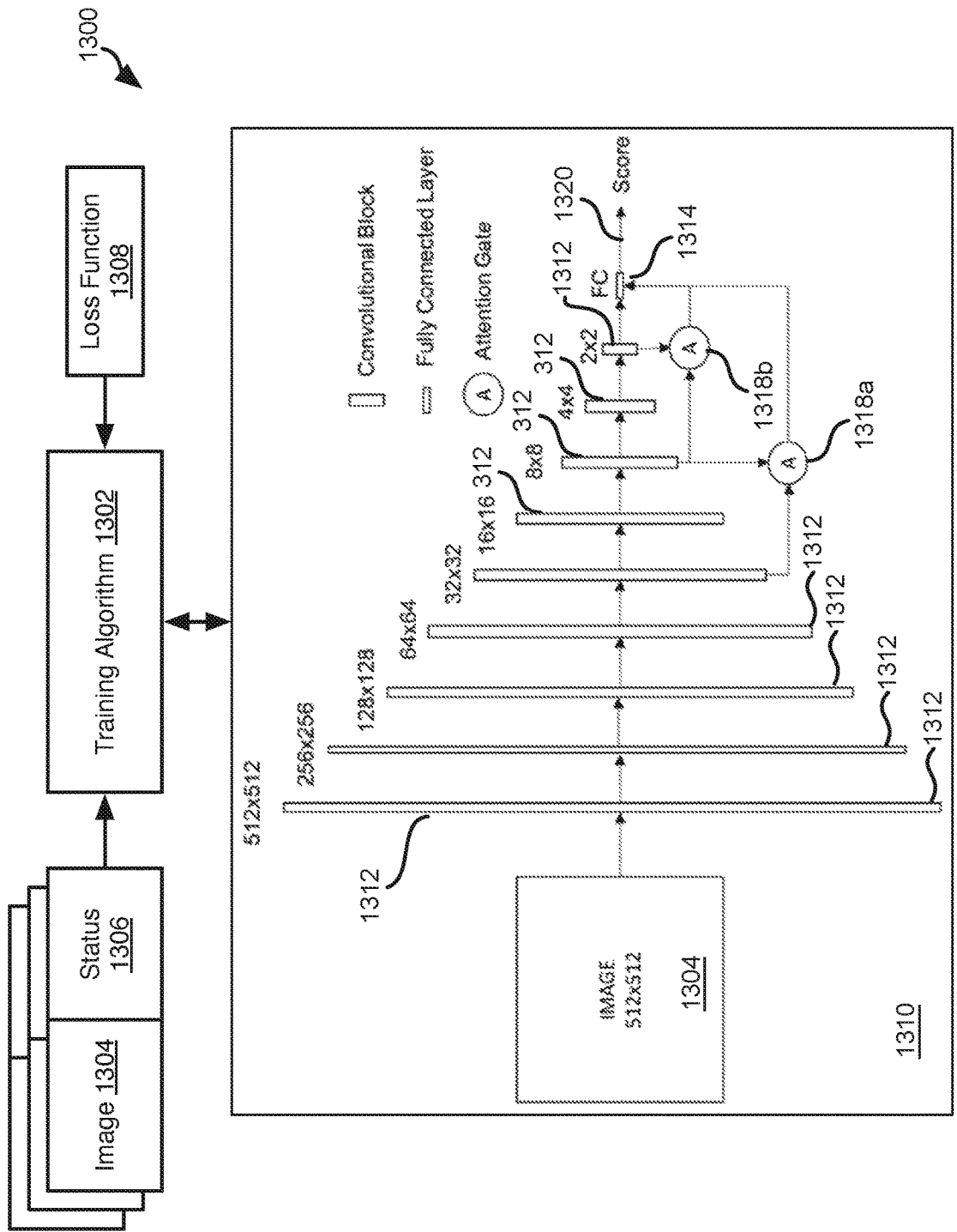
FIG. 13 is a schematic block diagram of a system for detecting adversarial images in accordance with an embodiment of the present invention.

Referring specifically to FIG. 13, the illustrated system 1300 may be used to train a machine learning model to identify authentic and corrupted images. In the system 1300, A training algorithm 1302 takes as inputs training data entries that each include an image 1304 and a status 1306 of the image 1304, the status indicating whether the image 1306 is contaminated or non-contaminated. The training algorithm 1302 also evaluates a loss function 1308 with respect to a machine learning model 1310. In particular, the training algorithm 1302 adjusts the machine learning model 1310 according to whether the machine learning model correctly determines the status 1306 of a given input image 1304.

In the illustrated embodiment, the machine learning model 1310 is an adversarial detection CNN. The CNN may include attention-gated skip connections and deep-supervision. In the illustrated embodiment, the CNN includes nine multi-scale stages 1312 followed by a fully connected layer 1314 that outputs an authenticity score 1320. Each multi-scale stage 1312 may contain three 3×3 convolutional layers, paired with batchnormalization and leaky rectified linear units (LeakyReLU). The first and last convolutional layers of each stage 1312 may be concatenated via dense connections which help reduce redundancy within the network by propagating shallow information to deeper parts of the network. Each multi-scale stage 1312 may be downscaled by a factor of two at the end of each multi-scale stage 1312, such as by max pooling. The fifth and seventh multi-scale stages 1312 may be passed through attention gates 1318*a*, 1318*b* before being concatenated with the last (ninth) stage 1312. The attention gate 1318*a* may be applied to the fifth stage 1312 according to a gating signal derived from the seventh stage 1312. The attention gate 1318b may be applied to the seventh stage 1312 according to a gating signal derived from the ninth stage 1312. Not all regions of the image are relevant for estimating periodontal diagnosis, so attention gates may be used to selectively propagate semantically meaningful information to deeper parts of the network. Adam optimization may be used during training which automatically estimates the lower order moments and helps estimate the step size which desensitizes the training routine to the initial learning rate.

In some embodiments, the images 1304 input to the network may be embodied as a raw 512×512 image 1304 and the output of the network may be a likelihood score 1320 indicating a likelihood that the input image 1304 is an adversarial example. The loss function 1308 may therefore decrease with accuracy of the score. For example, where a high score indicates an adversarial input image, the loss function 1308 decreases with increase in the likelihood score 1320 when the input image 1304 is an adversarial image. The loss function 1308 would then increase with increase in the likelihood score 1320 when the input image 1304 is not an adversarial image. The loss function 1308 may be implemented with categorical cross entropy and Adam optimization may be used during training which automatically estimates the lower order moments and helps estimate the step size which desensitizes the training routine to the initial learning rate.

The adversarial images 1304 in the training data set may be generated with any of projected gradient decent image contamination, synthetically generated images, and manually manipulated images by licensed dentists. Because the adversarial detection machine learning model 1310 may be sensitive to training parameters and architecture, a validation set may be used for hyperparameter testing and a final hold out test set may be used to assess final model performance prior to deployment.

The training algorithm 1302 and utilization of the trained machine learning model 1310 may be implemented using PYTORCH and AWS GPU instances in the same manner as described above with respect to FIG. 3.

In at least one possible embodiment, the system 1300 operates on three-dimensional images, such as a CT, by replacing two-dimensional convolutional kernels (e.g., 4×4 and 1×1) with three-dimensional convolution kernels (e.g., 4×4×4 or 1×1×1).

Figure 14A:
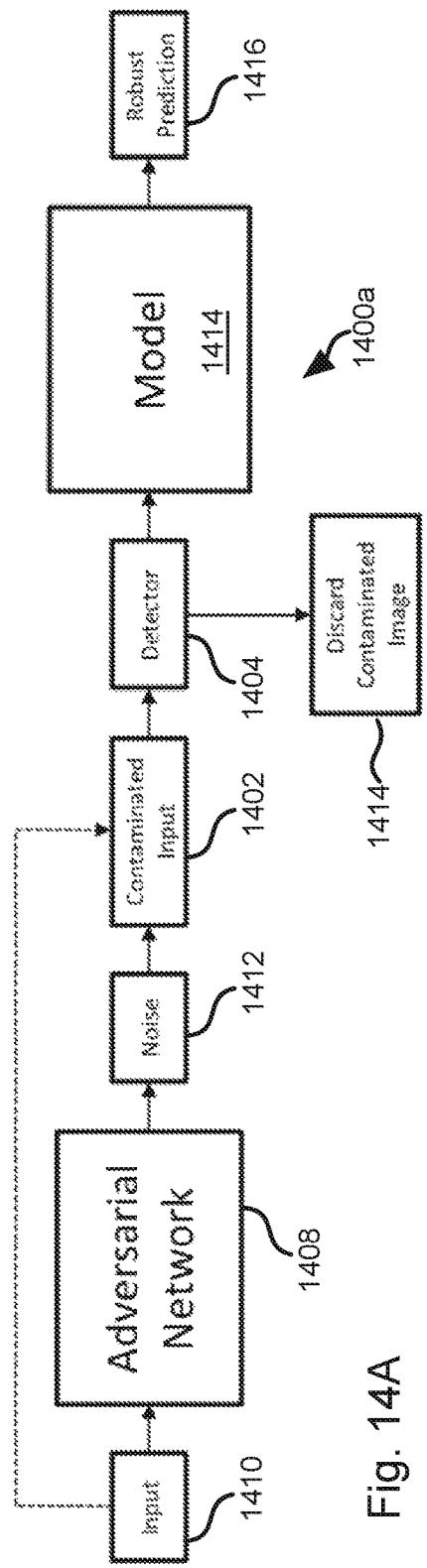
FIG. 14A is a schematic block diagram of a system for protecting a machine learning model from adversarial images in accordance with an embodiment of the present invention.

FIG. 14A is a schematic block diagram of a system 1400a for protecting a machine learning model from adversarial input images 1402 in accordance with an embodiment of the present invention. In particular, the system 1400a includes a detector 1404 that evaluates the authenticity of the input image 1402 and estimates whether the input image 1402 is adversarial. The detector 1404 may be implemented as the machine learning model 1310. If the image 1402 is found to be adversarial, the image is discarded as a contaminated image 1402

An adversarial network 1408 may receive an uncontaminated image 1410 and process the image 1410 to generate additive noise 1412 to contaminate the input image in order to deceive a victim machine learning model 1414. The victim model 1414 may be any machine learning model described herein or any machine learning model trained to transform images or generate inferences based on images. Each image 1410 may have an accurate prediction associated with an input image 1410 may be a prediction obtained by processing the input image 1410 using the victim model 1414 without added noise 1412 or according to labeling by some other means, such as by a human with expertise.

The noise 1412 is combined with the image 1410 to obtain the contaminated input image 1402 that is input to the detector 1404. The detector 1404 attempts to detect these adversarial images 1402 and discard them. Input images 1402 that are not found to be adversarial are then input to the machine learning model 1414 that outputs a prediction 1416. The prediction 1416 is more robust due to the presence of the detector 1404 inasmuch as there is more assurance that the image 1402 is not adversarial.

Figure 14B:
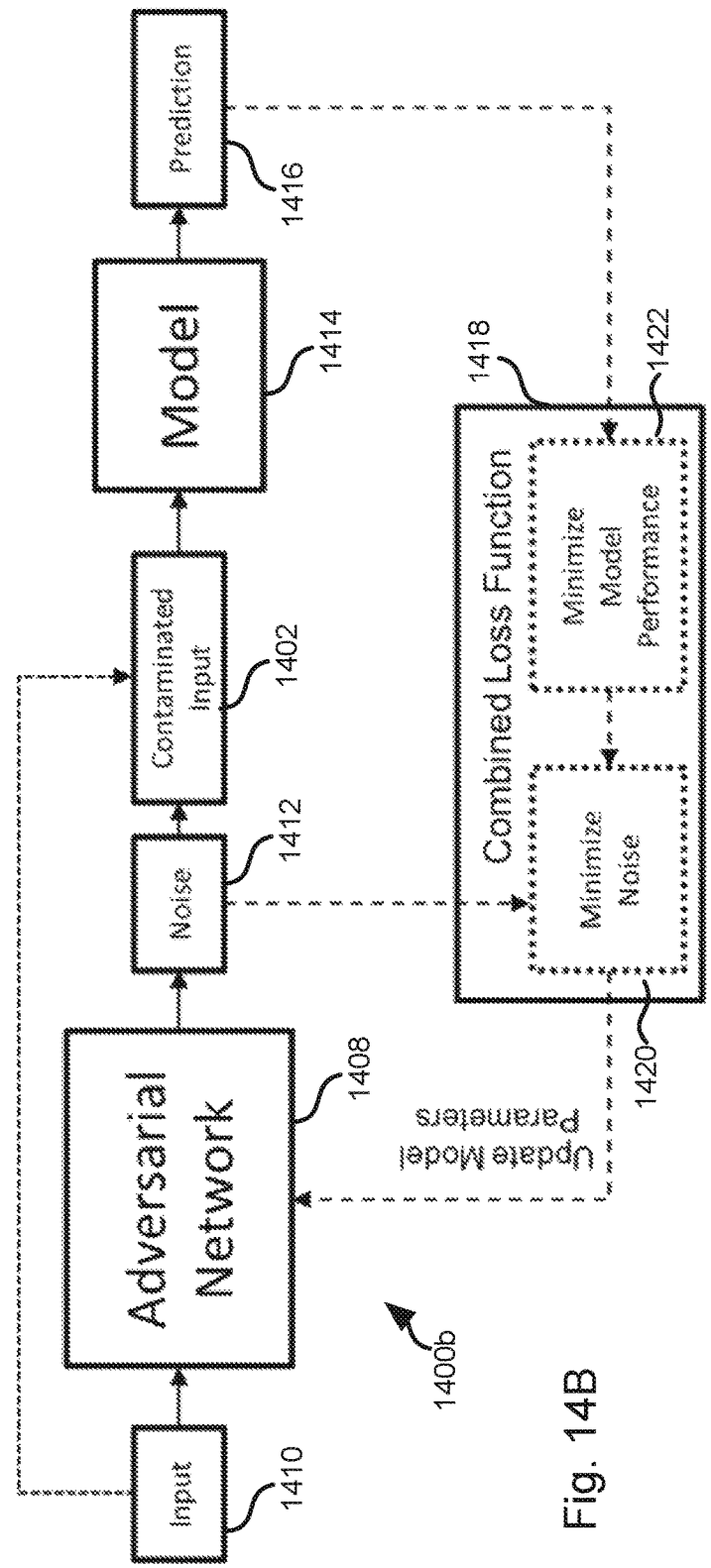
FIG. 14B is a schematic block diagram of a system for training a machine learning model to be robust against attacks using adversarial images in accordance with an embodiment of the present invention.

Referring to FIG. 14B, in some embodiments the illustrated system 1400b may be used to train an adversarial network 1408 to generate noise 1412 for contaminating input images 1410. This may be with the intent of generating adversarial images for training purposes, such as for training the machine learning model 1310. In other applications, adversarial images may be generated from patient images in order to protect patient privacy, e.g., prevent automated analysis of the patient's images. Accordingly, the detector 1404 may be omitted in the embodiment of FIG. 14b in order to expose the victim model 1414 to the adversarial images and assess its response.

The loss function of the adversarial network 1408 may be based on the prediction 1414, i.e. if the loss function decreases with increasing inaccuracy of the prediction. For example, the input image 1408 may be part of a training data entry including an accurate prediction. The difference between the prediction 1414 and the accurate prediction may therefore be evaluated to determine the output of the loss function that is used to update the adversarial network.

In some embodiments, the loss function is a loss function 1418 that has two goal criteria minimizing 1420 noise and minimizing 1422 model performance, i.e. maximizing inaccuracy of the prediction 1416. Accordingly, the loss function 1418 may be a function of inaccuracy of the prediction 1416 relative to an accurate prediction associated with the input image 1408 and is also be a function of the magnitude of the adversarial noise 1412. The loss function 1418 therefore penalizes the adversarial network 1408 according to the magnitude of the noise and rewards the adversarial network 1408 according to degradation of accuracy of the victim model 1414.

The adversarial network 1408 and its training algorithm may be implemented according to any of the machine learning models described herein. In particular, the adversarial network 1408 may be implemented as a generator according to any of the embodiments described herein. In some embodiments, the adversarial network 1408 utilizes a six multi-scale level deep encoder-decoder architecture. Each convolutional layer within the encoder and decoder stage of the networks may use three 3×3 convolutions paired with batchnormalization and rectified linear unit (ReLU) activations. Convolutional downsampling may be used to downsample each multi-scale level and transpose convolutions may be used to incrementally restore the original resolution of the input signal. The resulting high-resolution output channels may be passed through a 1×1 convolutional layer and hyperbolic tangent activation function to produce adversarial noise 1412, which may be in the form of an image, where each pixel is the noise to be added to the pixel at that position in the input image 1410. At each iteration, the adversarial noise 1412 may be added to an image 1410 from a repository of training data entries to obtain the contaminated input image 1402. The contaminated input image 1402 may then be processed using the victim model 1414. The training algorithm may update model parameters of the adversarial network 1408 according to the loss function 1418. In some embodiments, the loss function 1418 is a function of mean squared error (MSE) of the adversarial noise 1412 and inverse cross entropy loss of the victim prediction 1416 relative to an accurate prediction associated with the input image 1408. In some embodiments, the victim model 1414 (e.g., machine learning model 1310) and the adversarial network 1408 may be trained concurrently.

FIG. 14C is a schematic block diagram of a system 1400c for training a machine learning model to be robust against attacks using adversarial images in accordance with an embodiment of the present invention. In the illustrated embodiment, a contaminated image 1402, such as may be generated using an adversarial network, is processed using the victim model 1414, which outputs a prediction 1416. A training algorithm evaluates a loss function 1424 that decreases with accuracy of the prediction, e.g., similarity to a prediction assigned to the input image 1410 on which the contaminated image 1402 is based. The training algorithm then adjusts parameters of the model 1414 according to the loss function 1424. In the illustrated embodiment, the model 1414 may first be trained on uncontaminated images 1410 until a predefined accuracy threshold is met. The model 1414 may then be further trained using the approach of FIG. 14C in order to make the model 1414 robust against adversarial attacks.

FIG. 14D is a schematic block diagram of a system 1400d for modifying adversarial images to protect a machine learning model from corrupted images in accordance with an embodiment of the present invention. In the illustrated embodiment, input images 1402, which may be contaminated images are processed using a modulator 1426. The modulator adds small amounts of noise to the input image to obtain a modulated image. The modulated image is then processed using the machine learning model 1414 to obtain a prediction 1416. The prediction is made more robust inasmuch as subtle adversarial noise 1412 that is deliberately chosen to deceive the model 1414 is combined with randomized noise that is not selected in this manner. The parameters defining the randomized noise such as maximum magnitude, probability distribution, and spatial wavelength (e.g., permitted rate of change between adjacent pixels) of the random noise may be selected according to a tuning algorithm. For example, images 1402 based on images 1410 with corresponding accurate predictions may be obtained using an adversarial network 1408, such as using the approach described above with respect to FIG. 14B. The images 1410 may be modulated by modulator 1426 and processed using the model 1414 to obtain predictions. The accuracy of this prediction 1416 may be evaluated, noise parameters modified, and the images 410 processed again iteratively until noise parameters providing desired accuracy of the prediction 1416 is achieved.

For example, a low amount of randomized noise may not be sufficient to interfere with the adversarial noise 1412, resulting in greater errors relative to an intermediate amount of noise that is greater than the low amount. Likewise, where a larger amount of noise greater than the intermediate amount is used, accuracy of the machine learning model 1414 may be degraded due to low image quality. Accordingly, the tuning algorithm may identify intermediate values for the noise parameters that balance adversarial noise disruption with image quality degradation.

In some embodiments, the modulator 1426 is a machine learning model. The machine learning model may be a generator, such as according to any of the embodiments for a generator described herein. The modulator 1426 may therefore be trained using a machine learning algorithm to generate noise suitable to disrupt the adversarial noise 1412. For example, training cycles may include generating a contaminated input image 1402 as described above, processing the contaminated input image 1402 using the modulator 1426 to obtain a modulated input. The modulated input is then processed using the model 1414 to obtain a prediction 1416. A loss function that decreases with increase in the accuracy of the prediction 1416 relative to the accurate prediction for the image 1410 used to generate the contaminated input image 1402 may then be used to tune the parameters of the modulator 1426.

Figure 14E:
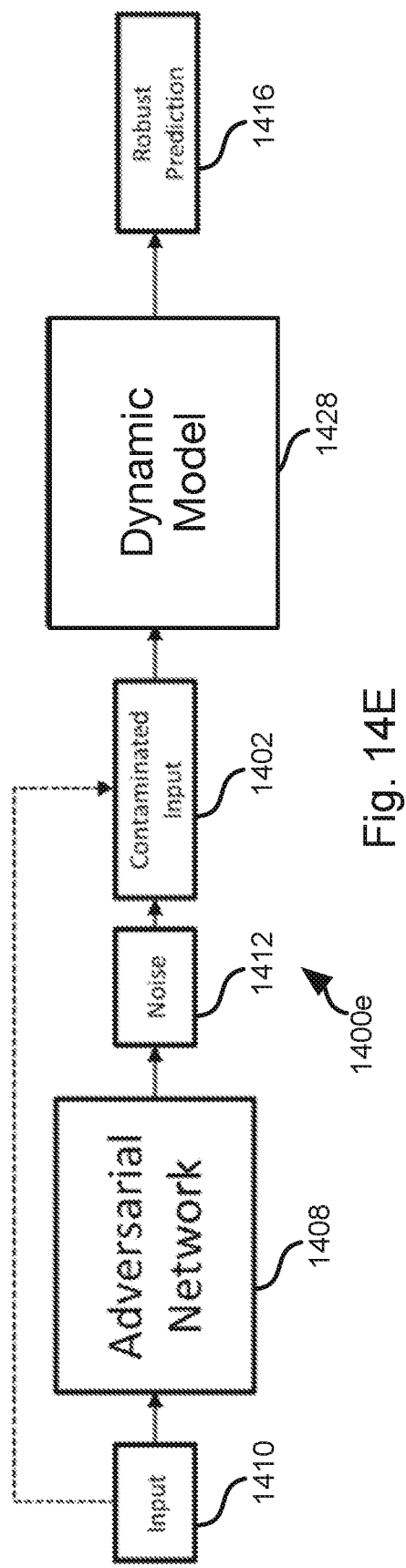
FIG. 14E is a schematic block diagram of a system for dynamically modifying a machine learning model to protect it from adversarial images in accordance with an embodiment of the present invention.

FIG. 14E is a schematic block diagram of a system 1400e for dynamically modifying a machine learning model to protect it from adversarial images in accordance with an embodiment of the present invention.

In the illustrated embodiment, input images 1402, which may be contaminated with adversarial noise 1412 are processed using a dynamic machine learning model 1428. In this manner, the ability to train the adversarial network 1408 to deceive the model 1428 is reduced relative to a static machine learning model 1414.

The dynamic machine learning model 1428 may be implemented using various approaches such as:

- The parameters of a machine learning model 1414 as described above are dynamically modified by different random noise each time the model 1414 outputs a prediction 1416, with the noise parameters of the random noise (maximum magnitude, probability distribution, etc.) being selected such that accuracy of the model 1414 is maintained within acceptable levels. The random variations of the parameters impairs the ability of the adversarial network 1408 to generate adversarial noise 1412 that is both undetectable and effective in deceiving the model 1414.
- A plurality of machine learning models 1414 are independently trained to generate predictions 1416. Due to the stochastic nature of the training of machine learning models, the parameters of each machine learning model 1414 will be different, even if trained on the same sets of training data. Alternatively, different training data sets may be used for each machine learning model 1414 such that each is slightly different from one another. In yet another alternative, hyperparameters or other parameters that govern training of each model may be deliberately set to be different from one another. In yet another alternative, different types of machine learning models 1414 (DNNs and CNNs) or differently structured machine learning models (different numbers of stages, differently configured stages, different attention gate configurations, etc.) may be used in order to ensure variation among the machine learning models 1414. The dynamic model 1428 may then (a) randomly select among a plurality of models 1414 to make each prediction 1416, (b) combine predictions 1416 from all or a subset of the models 1414 and combine the predictions 1416, (c) apply random weights to the predictions 1416 from all or a subset of the models 1414 and combine the weighted predictions to obtain a final prediction that is output from the dynamic model 1428.

Referring to FIGS. 15 through 19, cross-institutional generalizability of AI models is hampered in dentistry because of privacy concerns. In addition, patient datasets from a clinic in Georgia might differ substantially from clinics in New York or San Francisco. A model trained on a dataset in one region might not perform well on patient populations originating from a different region of the world because clinical standards, patient demographics, imaging hardware, image acquisition protocols, software capabilities, and financial resources can vary domestically and internationally. Dentistry is particularly prone to cross-institutional variability because of the lack of clinical standardization and high degree of differentiation in oral hygiene practices among different patient populations.

Training dental AI models to reach cross-institutional generalizability is challenging from a data management and artificial intelligence (AI) model management perspective because in order to establish the correct treatment protocol or diagnosis many different data sources are often combined. To obtain the correct codes on dental procedures, dental image analytics may be combined with patient metadata, such as clinical findings, Decayed-Missing-Filled-Treated (DMFT) information, age, and historical records. However, in many cases the past medical history is not known or is not stored in a single place. Protected, disparate, restricted, fragmented, or sensitive patient information hinders aggregation of patient medical history.

To overcome this challenge, the approach described below with respect to FIGS. 15 through 19 may be used to allows models to learn from disparate data sources and achieve high cross-institutional generalizability while preserving the privacy of sensitive patient information.

Figure 15:
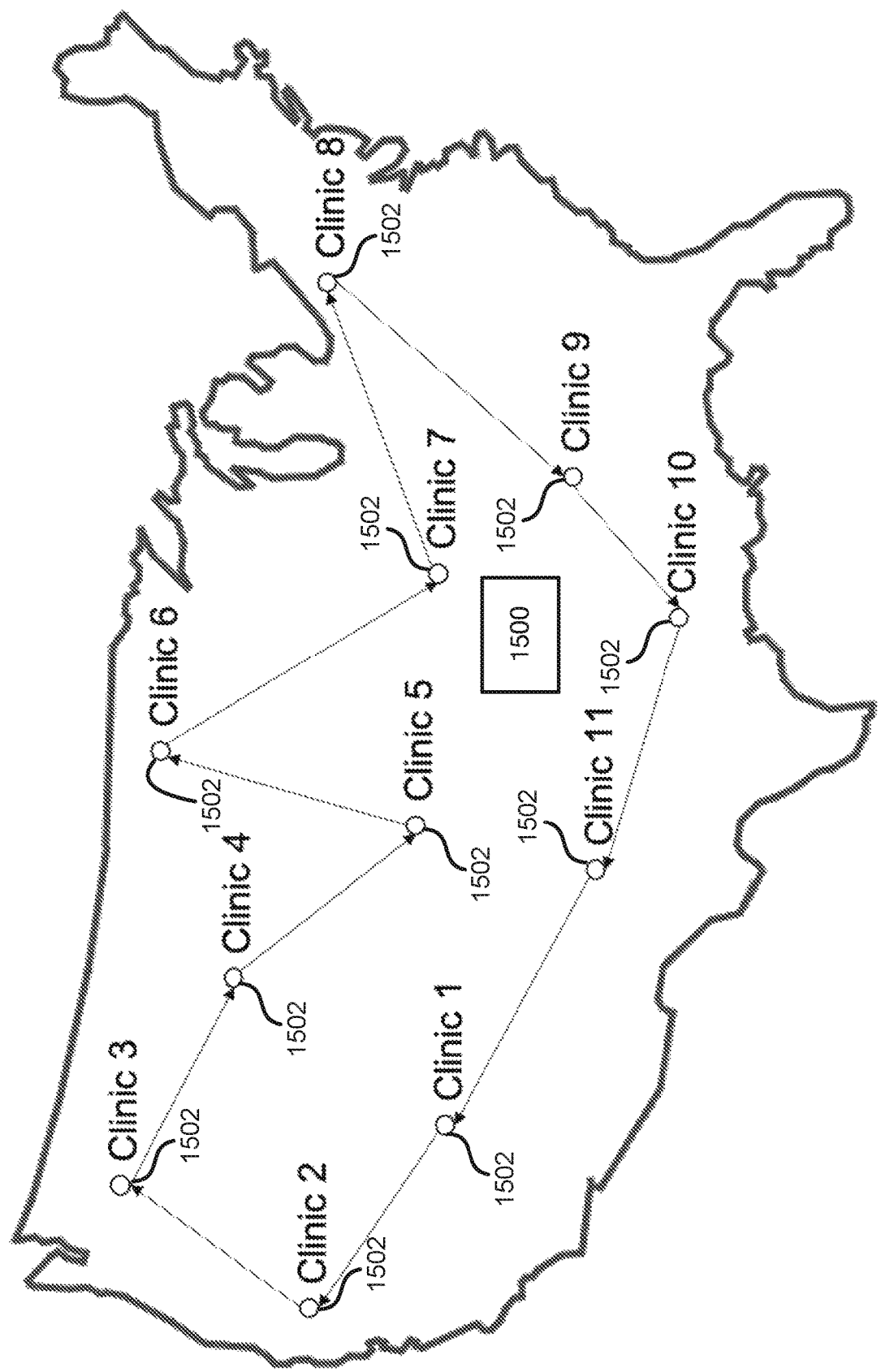
FIG. 15 is a schematic block diagram illustrating the training of a machine learning model at a plurality of disparate institutions in accordance with an embodiment of the present invention.

Referring specifically to FIG. 15, in a typical implementation, there may be a central server 1500 that trains a machine learning model with respect to data from various institutions 1502. The institutions 1502 may be an individual dental clinic, a dental school, a dental-insurance organization, an organization providing storage and management of dental data, or any other organization that may generate or store dental data. The dental data may include dental images, such as dental images according to any of the two-dimensional or three-dimensional imaging modalities described hereinabove. The dental data may include demographic data (age, gender) of a patient, comorbidities, clinical findings, past treatments, Decayed-Missing-Filled-Treated (DMFT) information, and historical records.

As discussed below, a machine learning model may be trained on site at each institution with coordination by the central server 1500 such that patient data is not transmitted to the central server 1500 and the central server 1500 is never given access to the patient data of each central server 1500.

Figure 16:
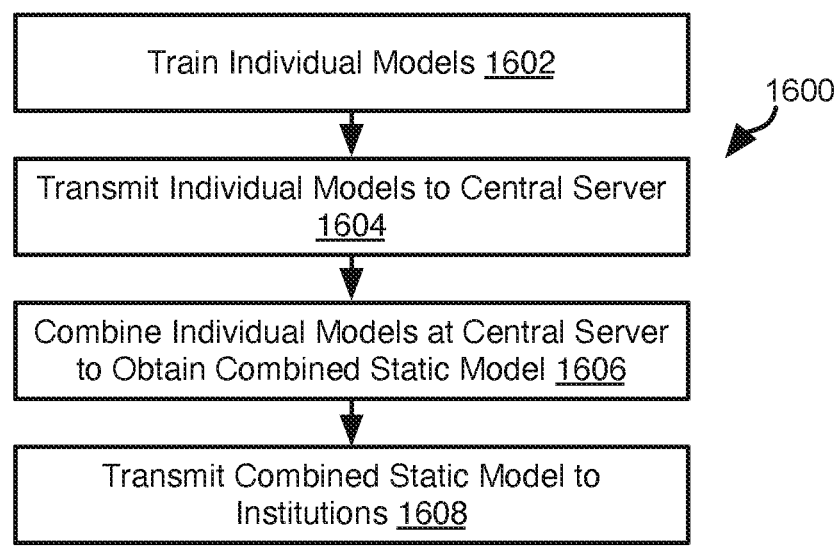
FIG. 16 is a process flow diagram of a method for generating a combined static model from a plurality of disparate institutions in accordance with an embodiment of the present invention.
Figure 17:
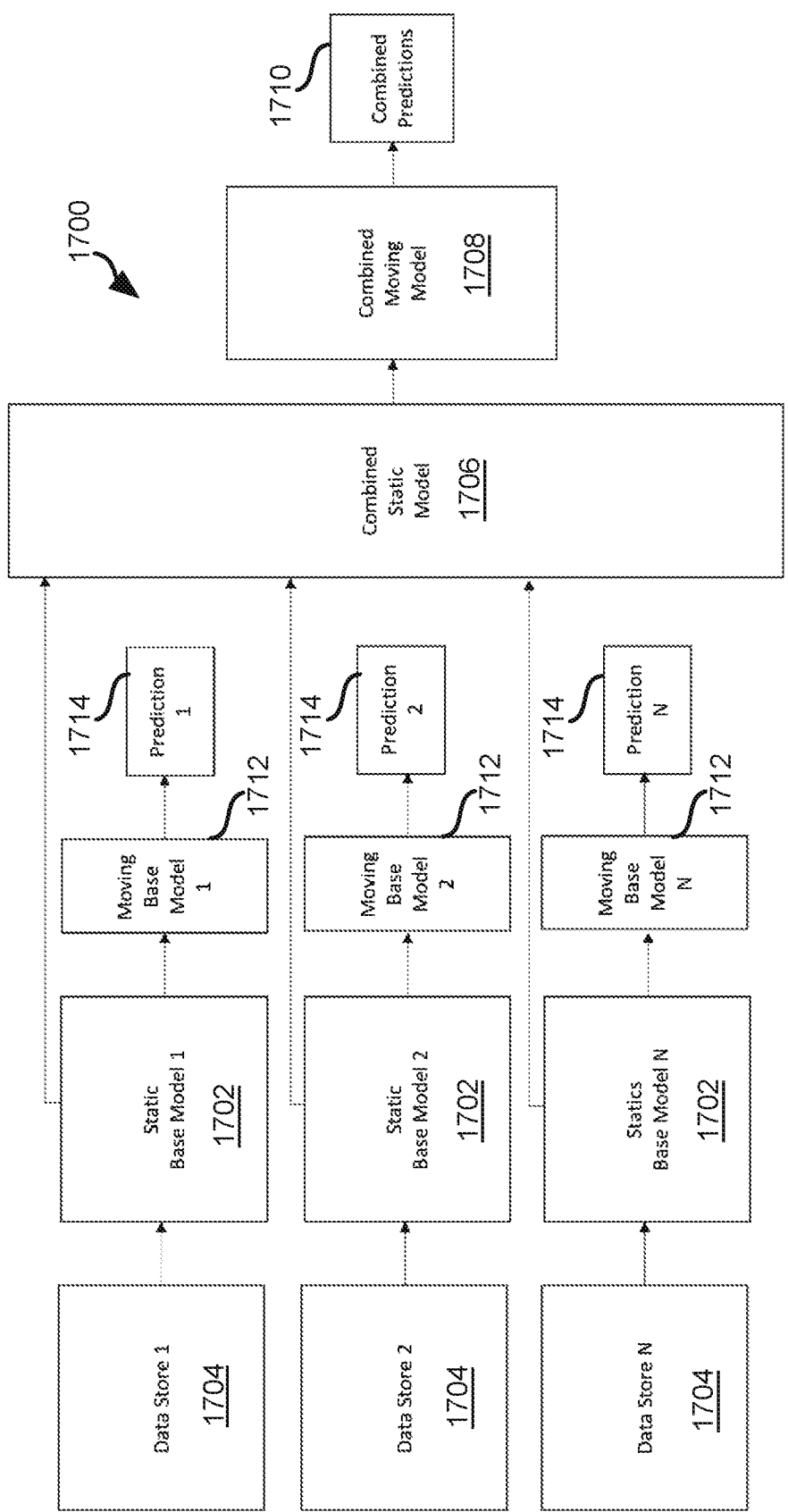
FIG. 17 is a schematic block diagram illustrating the training of a combined static model by a plurality of disparate institutions in accordance with an embodiment of the present invention.

Referring to FIGS. 16 and 17, a method 1600 may include training 1602 individual machine learning models 1702 at each institution 1502 using a data store 1704 of that institution, the data store storing any of the dental data described above with respect to FIG. 15. Note that processing "at each institution 1502" may refer to computation using a cloud-based computing platform using an account of the institution such that the data store 1704 is accessible only by the institution and those allowed access by the institution. This may be any machine learning model trained using any algorithm known in the art, such as a neural network, deep neural network, convolution neural network, or the like. The machine learning model may be a machine learning model according to any of the approaches described above for evaluating a dental feature (tooth, JE, GM, CEJ, bony points), dental condition (PD, CAL), or diagnose a dental disease (e.g., any of the periodontal diseases described above). The machine learning model may also be trained to identify bone level, enamel, dentin, pulp, furcation, periapical lines, orthodontic spacing, temporal mandibular joint (TMJ) alignment, plaque, previous restorations, crowns, root canal therapy, bridges, extractions, endodontic lesions, root length, crown length, or other dental features or pathologies.

The machine learning models 1702 trained by each institution 1502 may be transmitted 1604 to the central server 1500, which combines 1606 the machine learning models 1702 to obtain a combined static model 1706. Combination at step 1606 may include bagging (bootstrap aggregating) the machine learning models 1702. For example, the combined static model 1706 may be utilized by processing an input using each machine learning model 1702 to obtain a prediction from each machine learning model 1702. These predictions may then be combined (e.g., averaged, the most frequent prediction selected, etc.) to obtain a combined prediction. Alternatively, the machine learning models 1702 themselves may be concatenated to obtain a single combined static machine learning model 1706 that receives an input and outputs a single prediction for that input.

The combined static model 1706 may then be transmitted 1608 by the server system 1500 to each of the institutions 1502.

Figure 18:
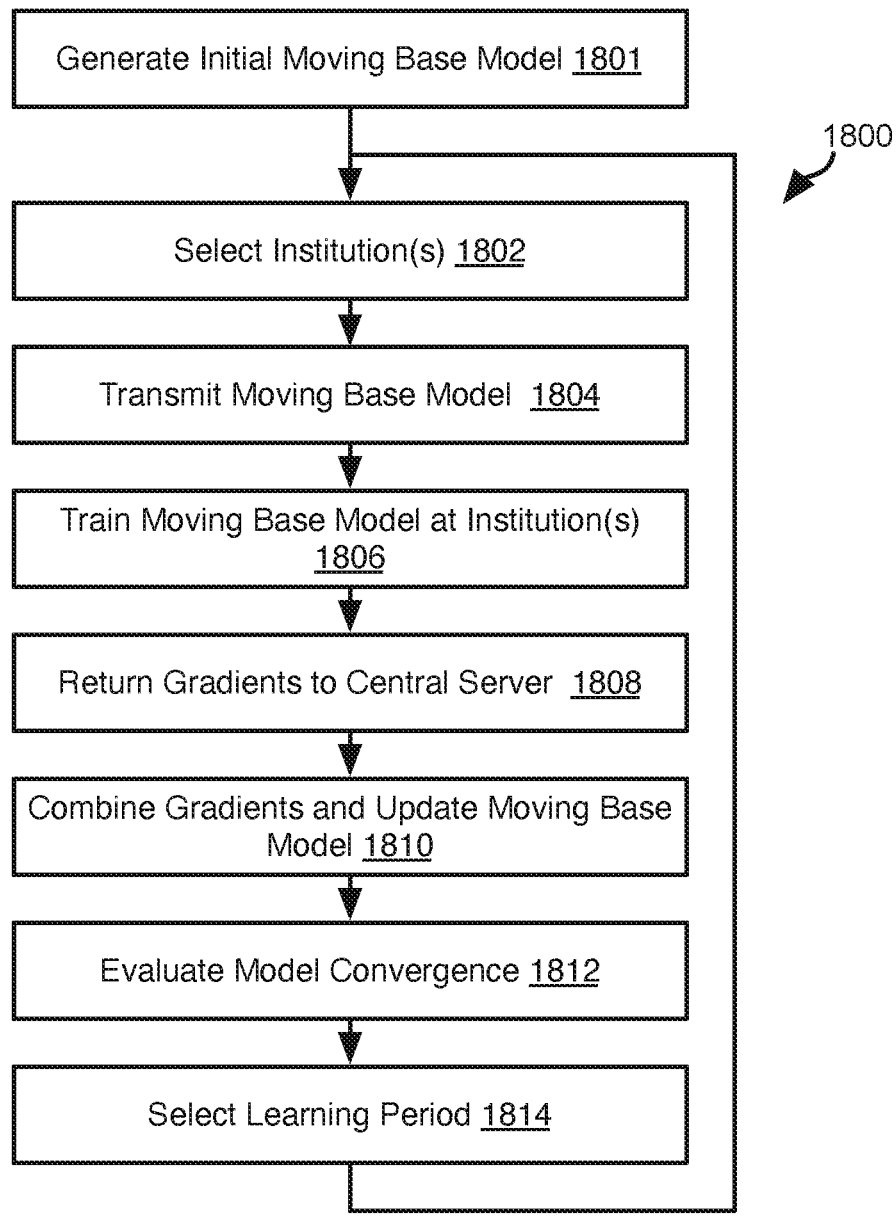
FIG. 18 is a process flow diagram of a method for training a moving base model for a plurality of disparate institutions in accordance with an embodiment of the present invention.

Referring to FIG. 18, while still referring to FIG. 17, a method 1800 may be used to train a combined moving model 1708. The combined moving model 1708 is combined by the server system 1500 with the combined static model 1706 to obtain a combined prediction 1710 for a given input during utilization. The combined moving model 1708 may be trained by circulating the combined moving model 1708 among the plurality of institutions 1502 and training the combined moving model 1708 in combination with the combined static model 1706 at each of the institutions 1502. This may be performed in the manner described below with respect to step 1806.

For example, the method 1800 may include the central server 1500 generating 1801 an initial moving base model that is used as the combined moving model 1708 in the first iteration of the method 1800. The initial moving base model may be populated with random parameters to provide a starting point for subsequent training. Alternatively, the initial moving base model may be trained using a sample set of training data. This initial training may include training the initial moving base model in combination with the combined static model 1706

One or more institutions 1502 are then selected 1802 by the central server 1500, for example, from 1 to 10 institutions. Where a single institution 1500 is processed at each iteration of the method 1800, the method 1800 may proceed differently as pointed at various points in the description below. The groups of institutions 1500 selected may be static, i.e. the same institutions will be selected as a group whenever that group is selected, or dynamic, i.e. each selection at step 1802 until a predefined number of institutions have been selected.

The selection at step 1802 may be performed based on various criteria. As will be discussed below, the moving base model as trained at each institution may be transmitted among multiple institutions. Accordingly, the latency required to transmit data among the institutions 1502 may be considered in making the selection at step 1802, e.g., a solution to the traveling salesman problem may be obtained to reduce the overall latency of transmitting the moving base model among the institutions 1502. In some embodiments, step 1802 may include selecting one or more institutions based on random selection with the probability of selection of each institution 1502 being a function of quality of data (increasing probability of selection with increasing quality) and time since the each institution 1502 was last selected according to the method 1800 (increasing probability of selection with increasing time since last selection). Quality of data may be a metric of the institution 1502 indicating such factors as authoritativeness in field (e.g., esteemed institution in field of dentistry), known accuracy, known compliance with record-keeping standards, known clean data (free of defects), quantity of data available, or other metric of quality.

The method 1800 may then include the central server 1500 transmitting 1804 the moving base model to the selected institutions 1502. For the first iteration of the method 1800, this may include transmitting the initial moving base model to the selected institutions 1502. Otherwise, it is the combined moving model 1708 resulting from a previous iteration of the method 1800.

Each institution 1402 then trains a moving base model 1712 that is initially a copy of the base model received at step 1804, which is then combined with the combined static model 1706 transmitted to the institutions 1502 at step 1608. For example, each of the moving base model 1712 and the combined static model 1706 may include multiple layers, including multiple hidden layers positioned between a first layer and a last layer, such as a deep neural network, convolution neural network, or other type of neural network. One or more layers including the last layer and possibly one or more layers immediately preceding the last layer are removed from the combined static model 1706. For example, where the combined static model 1706 is a CNN, the fully connected layer and possibly one or more of the multi-scale stages immediately preceding it may be removed.

The outputs of the last layer remaining of the combined static model 1706 is then concatenated with outputs of a layer of the moving base model 1712 positioned in front of a final layer (e.g., a fully connected layer), e.g. at least two layers in front of the final layer (hereinafter "the merged layer"). For example, the combined static model 1706 (prior to layer removal) and the moving base model 1712 may be identically configured, e.g. same number of stages of the same size. For example, each may be a CNN having the same number of stages with the starting stages being of the same size, the same downsampling between stages, and each ending with a fully connected layer. However, in other embodiments, the models 1706, 1712 may have different configurations.

Concatenating outputs of the final layer of the truncated combined static model 1706 with the outputs of the merged layer may include a combined output that has double the depth of the outputs of the final layer and merged layer individually. For example, where the final layer has a 10×10 output with a depth of 100 (10×10×100) would become a 10×10×200 stage following concatenation. In other embodiments, the outputs of the final layer and merged layer may be concatenated and input to a consolidation layer such that the depth output from the consolidation layer is the same as the output of the merged layer (e.g. 10×10×100 instead of 10×10×200). The consolidation layer may be a machine learning stage, e.g. a multi-scale network stage followed by downsampling by a factor of 2, such that training of the combined static model 1706 and moving base model 1712 includes training the consolidation layer to select values from the final layers of the truncated models to output from the consolidation layer.

The moving base model 1712 as combined with the combined static model 1706 may then be trained 1806 at the selected institution 1502. This may include, for each training data entry of a plurality of training data entries, an input to the first stage of the combined static model 1706 and the moving base model 1712 to obtain a prediction 1714. The training data may be the same as or different from the training data used to train the static models at step 1602. The parameters of the moving base model 1712 may then be modified according to the accuracy of the predictions 1714 for the training data entries, e.g. as compared to the desired outputs indicated in the training data entries. The parameters of the combined static model 1706 may be maintained constant. The manner in which the moving base model 1712 and combined static model 1706 are combined may be as described in the following paper, which is hereby incorporated herein by reference in its entirety:

Kearney, V., Chan, J. W., Wang, T., Perry, A., Yom, S. S., & Solberg, T. D. (2019). Attention-enabled 3D boosted convolutional neural networks for semantic CT segmentation using deep supervision. *Physics in Medicine & Biology*, 64 (13), 135001.

The method 1700 may include returning 1808 gradients obtained during the training at step 1806 to the server system 1500. As known in the art, the weights and other parameters of a machine learning model may be selected according to gradients. These gradients change over time in response to evaluation of a loss function with respect to a prediction from the machine learning model in response to an input of a training data entry and a desired prediction indicating in the training data entry. Accordingly, the gradients of the moving base model 1712 as constituted after the training step 1806 may be returned 1808 to the central server. Note that since gradients are of interest and are what is provided to the central server 1500 in some embodiments, the training step 1806 may be performed up to the point that gradients are obtained but the moving base model 1712 is not actually updated according to the gradients.

The gradients from the multiple institutions selected at step 1802 may then be combined by the server system 1500 to obtain combined gradients, e.g. by averaging the gradients to obtain averaged gradients. The combined gradients may then be used to select new parameters for the combined moving model 1708 and the combined moving model 1708 is then updated according to the new parameters.

Figure 19:
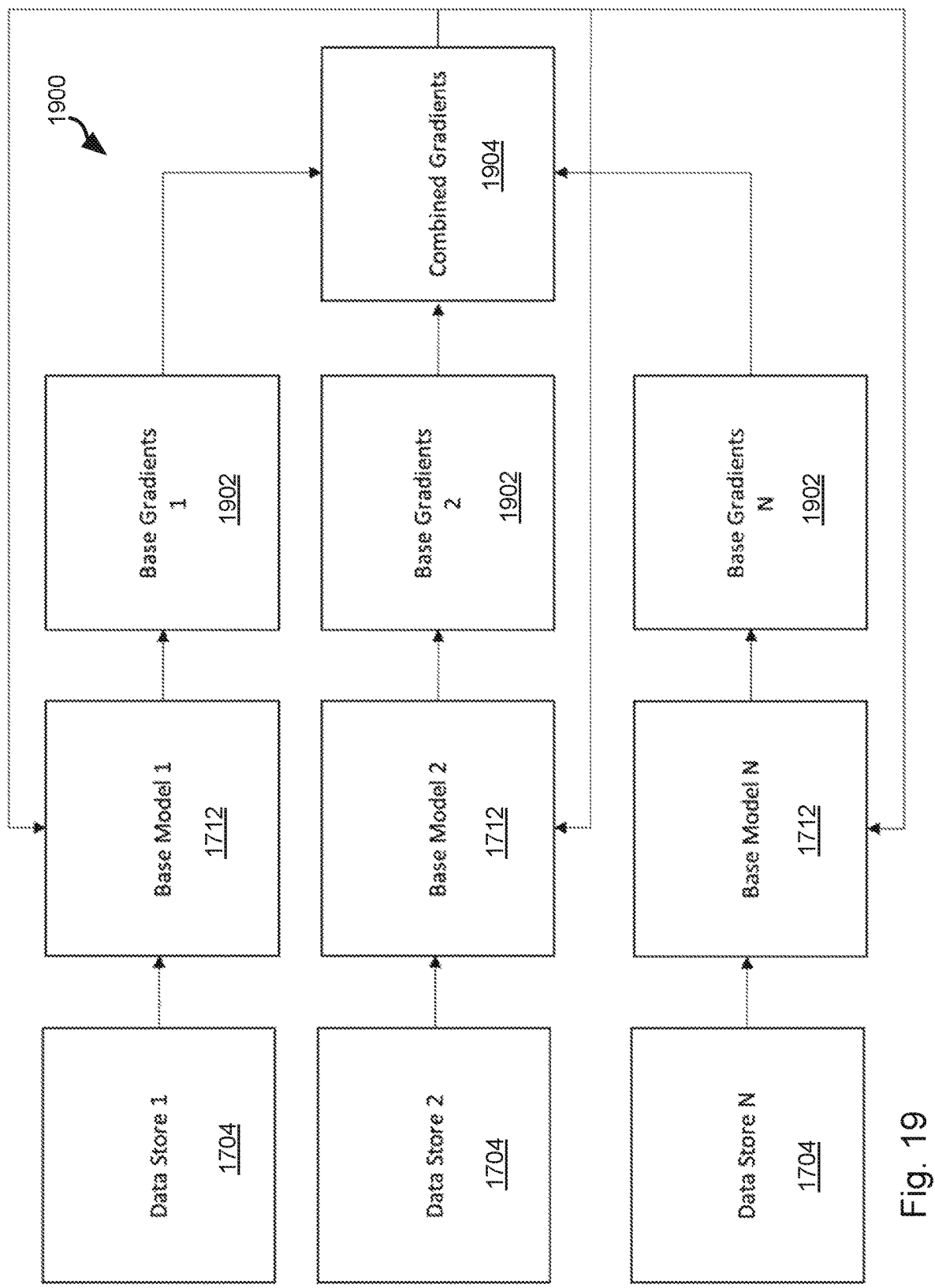
FIG. 19 is a schematic block diagram of a system for combing gradients from a plurality of disparate institutions.

FIG. 19 illustrates an approach 1900 for combining gradients from each moving base model 1712 at each institution 1502. Each institution 1502 trains the moving base model 1712 using its data store 1704 to obtain base gradients 1902 that define how to modify the parameters of the moving base model 1712 in subsequent iterations. The base gradients 1902 are returned to the central server 1500 that combines the base gradients 1902 to obtain combined gradients 1904. These combined gradients 1904 are then used to update the combined moving model 1708 on the server. The combined moving model 1708 as updated is then transmitted to the institutions 1502 and used and the moving base model 1712 in the next iteration of the method 1800. Note that the institutions 1502 that receive the updated combined moving model 1708 may be different from those that provided the base gradients 1902 since different institutions 1502 may be selected at each iteration of the method 1800.

Returning again to FIG. 18, the method 1800 may include the central server 1500 evaluating 1812 model convergence. For example, each institution selected at step 1802 may return values of the loss function of the training algorithm for inputs processed using the moving base model 1712 during the training step 1806. The central server 1500 may compare the values of the loss function (e.g., an average or minimum of the multiple values reported) to the values returned in a previous iteration to determine an amount of change in the loss function (e.g. compare the minimum loss function values of the current and previous iteration).

The method 1800 may include selecting a learning period 1814 according to the rate of convergence determined at step 1812. The learning period may be a parameter defining how long a particular institution 1502 is allowed to train 1806 its moving base model 1712 before its turn ends and the selection process 1802 is repeated. As the rate of convergence becomes smaller, the learning period becomes longer. Initially, the rate of convergence may be high such that new institutions 1502 are selected 1802 at first intervals. As the rate of convergence falls, institutions 1502 are selected 1802 at second intervals, longer than the first intervals. This allows for a highly diverse training sets at initial stages of training, resulting in more rapid training of the combined moving model 1708. Enforcement of the learning period may be implemented by the central server 1500 by either (a) instructing each institution 1502 to perform the training step 1806 for the learning period or (b) instructing the institution 1502 to end the training step 1806 upon expiry of the learning period following selection 1802 or some time point after selection of the institution 1502.

The method 1800 may then repeat from step 1802 with selection 1802 of another set of institutions 1502. Since the selection 1802 is random, it is possible that one or more of the same institutions 1502 may be included in those select in the next iteration of the method 1800.

In embodiments where a single institution 1502 is selected at step 1802, step 1810 may be modified. For example, the institution may send the gradients of the moving base model 1712 to the central server, which then updates the parameters of the combined moving model 1708 according to the gradients without the need to combine the gradients with those of another institution. Alternatively, parameters of the moving base model 1712 may be updated by the institution according to the training step 1806 and the moving base model 1712 may be transmitted to the central server 1500, which then uses the moving base model 1712 as the combined moving model 1708 for a subsequent iteration of the method 1800. Since the institution 1502 may update the combined moving model 1708, the institution 1502 may transmit the combined moving model 1708 to another institution 1502 selected by the server system 1500 rather than sending the updated combined moving model 1708 to the server system 1500.

When the combination of the combined static model 1706 and the combined moving model 1708 have reached a desired level of accuracy and/or have converged (i.e., change between iterations of the method 1800 is below a predefined convergence threshold or threshold condition), the combination may then be used to generate combined predictions 1710 either on the server system 1500 or by transmitting the latest version of the combined moving model 1708 to the institutions such that they may generate predictions along with their copy of the combined static model. The combined moving model 1708 may be combined with the combined static model 1706 in the same manner as described above with respect to step 1806 for combining the moving base model 1712 with the combined static model 1706, i.e. truncating the combined static model 1706 to obtain a truncated model and concatenating the outputs of the truncated model with outputs of an intermediate layer of the combined moving model 1708.

The approach of FIG. 18 may have the advantage that, when the combined static model 1706 is maintained constant, catastrophic forgetting that might result from only sequential training is reduced. Likewise, where only the parameters of the combined moving model 1708 are updated, the processing of batches of training data at each iteration at an institution 1500 is speeded up and batch size may be increased. The only processing using the combined static model 1706 is a forward pass of input data and computation of gradients or new parameters can be omitted for the combined static model 1706.

Figure 20:
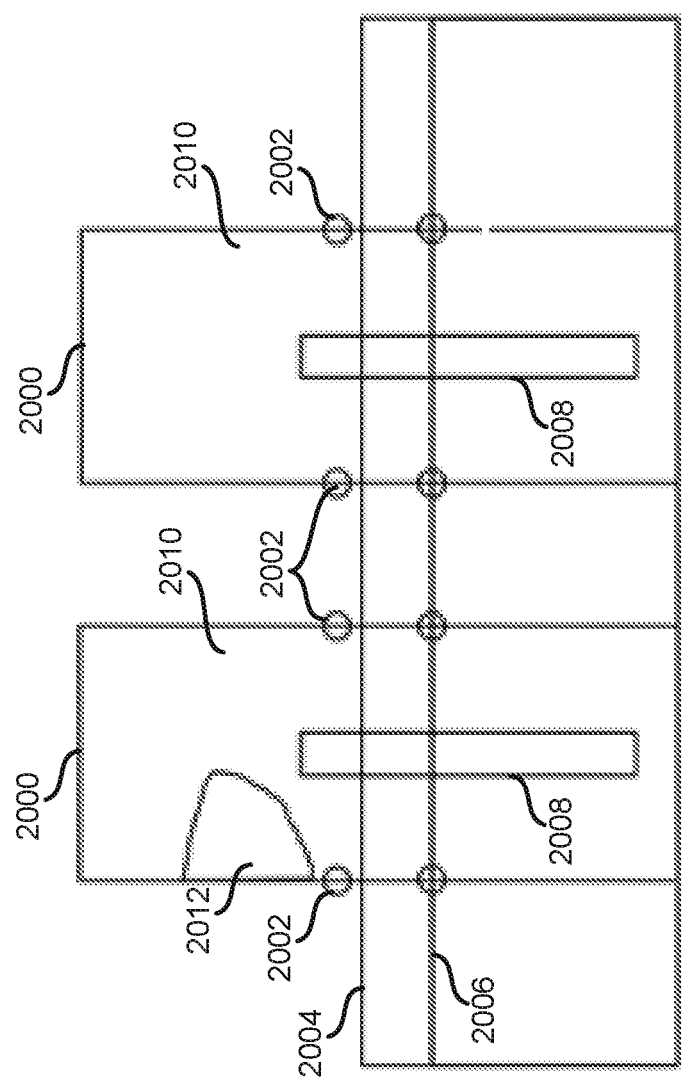
FIG. 20 is a schematic block diagram illustrating dental anatomy.

FIG. 20 includes a schematic representation of dental anatomy that may be represented in a dental image according to any of the imaging modalities described herein. For example, one or more teeth 2000 may be represented. Each tooth 2000 may have a CEJ 2002 that can be measured at various points around the tooth 2000. A GM, e.g., gum line, 2004 may also be represented along with the bone level 2006. Parts of a the teeth 2000 such as pulp 2008 and dentin 2010 may also be identified. Carious lesions (e.g., caries or cavities) 2012 may also be represented.

A machine learning model, such as any of the architectures described herein for labeling teeth (see, e.g., the approach of FIG. 8) may be used to label dental anatomy. Likewise, the approaches described above for measuring features of dental anatomy (see, e.g., the approach of FIGS. 9 and 10) may be used to measure dental anatomy. In particular, training data entries including images (inputs) and labels of the dental anatomy (desired output) may be used to train a machine learning model to output dental anatomy labels for a given input image, such as according to the approaches described hereinabove. Likewise, training data entries including images and labels of dental anatomy (input) and labels of measurements of dental anatomy (desired output) may be used to train a machine learning model to output measurements for a given input image with its corresponding labels of dental anatomy, such as according to the approaches described herein above. In particular, the machine learning model may be a CNN. However, other machine learning approaches, such as random forest, gradient boosting, support vector machine, or the like may also be used.

For a given item of dental anatomy, such as any of those referenced herein, particularly those referenced with respect to FIG. 20, one or more machine learning models may be trained to measure that item of dental anatomy. Measurements of an item of dental anatomy may include its center of mass, relative distance to other anatomy, size distortion, and density.

For a carious lesion 2012 in a tooth 2000, machine learning models may be trained to obtain the following measurements of the carious lesion 2012: volume, area, distance to pulp, percent of tooth covered by it, distance into dentin, involved surfaces of the tooth, and identifier of the affected tooth. Machine learning models may also be trained to identify fillings or other restorations on teeth and their measurements such as volume, area, percent of tooth covered by it, involved surfaces of the tooth, material, type, and identifier of the affected tooth.

Machine learning models may be trained to identify and measure periodontal anatomy such as distal gingival margin, mesial gingival margin, distal CAL, mesial CAL, distal PD, mesial PD, distal bone level, mesial bone level, and the identifier of the tooth for which the periodontal anatomy is identified and measured.

Machine learning models may be trained to identify and measure dental anatomy that may be used to determine the appropriateness of root canal therapy at a given tooth position such as crown-to-root-ratio, calculus, root length, relative distance to adjacent teeth, furcation, fracture, and whether the tooth at that tooth position is missing.

The manner in which a machine learning model is trained to perform any of these measurements may be as described above with respect to FIG. 10 except that any of the above-described measurements may be used in the place of pocket depth. Likewise, additional or alternative labels (e.g., pixel masks) of features in an image may be used, such as labels for caries, restorations on caries, or defects in restorations as described below.

Figure 21:
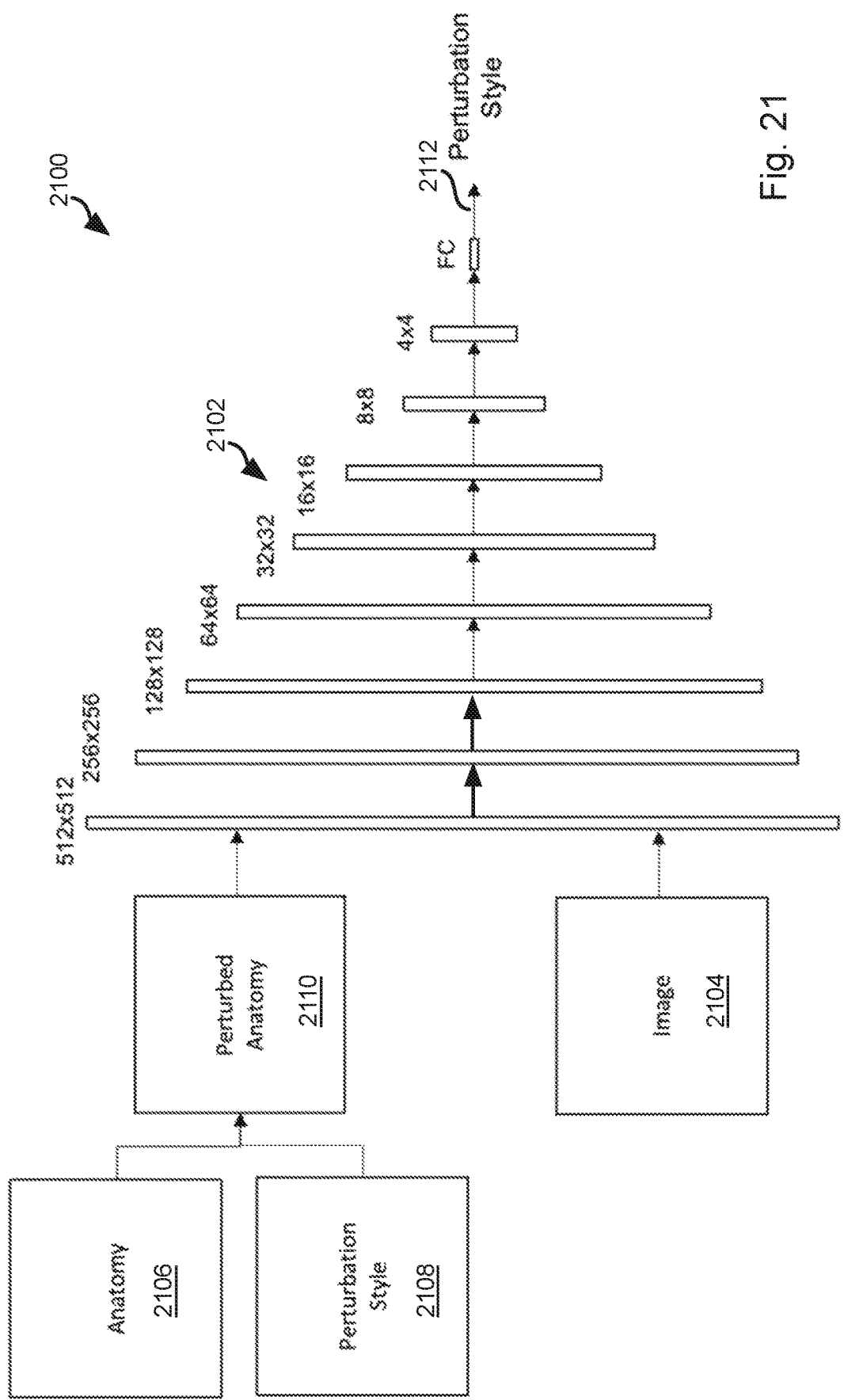
FIG. 21 is a schematic block diagram of a system for identifying perturbations to anatomy labels in accordance with an embodiment of the present invention.

FIG. 21 is a schematic block diagram of a system 2100 for identifying perturbations to anatomy labels in accordance with an embodiment of the present invention. The system 2100 may include an encoder network 2102. The encoder network 2102 may include a number of multi-scale stages with downsampling between them with the last stage coupled to a fully connected layer. The encoder network 2102 may be implemented according to any of the approaches described above for implementing a CNN. Other machine learning approaches may also be used, such as random forest, gradient boosting, or support vector machine.

Training data entries may each include an image 2104, such as an image of dental anatomy according to any of the imaging modalities described herein. Each training data entry may further include an anatomy label 2106, which may be a label of any dental anatomy (including caries or other dental pathologies) as described herein. Each training data entry may further include a perturbation style 2108. The perturbation style 2108 includes an adjustment to boundaries of the anatomy label (e.g., pixel mask) 2106. In particular, the perturbation style 2108 may include erosion, e.g., shrinking of the image area occupied by the label 2106, dilation, e.g. expanding the image area occupied by the label 2106, increasing roughness of the boundary of the label 2106, or increasing smoothness of the boundary of the label 2106, or changing another property of the label 2016. The perturbation style 2108 may be represented in a predefined format, e.g. a numerical value indicating the type of the perturbation (erode, dilate, roughen boundary, smooth boundary) and a degree of the perturbation (amount of erosion, amount of dilation, amount of roughening, amount of smoothing). The values may be interpreted according to a perturbation algorithm that implements the type and the degree of perturbation on a given input label.

The label 2106 may be adjusted according to the perturbation style 2108 (eroded, dilated, roughened, or smoothed), such as using the perturbation algorithm, to obtain a perturbed anatomy label 2110. The perturbed anatomy label 2110 and image 2104 are concatenated and input to the encoder 2102 that outputs an estimated perturbation style. The loss function may therefore increase with an increase in the difference between the estimated perturbation style 2112 and the perturbation style 2108 of the training data entry. Accordingly, the training algorithm may process training data entries and adjust parameters of the encoder 2102 according to the loss function to train the encoder 2102 to determine the perturbation style 2108 for a given input image.

Following training, an image 2014 and anatomy label 2106 may be processed using the encoder 2102 to obtain an estimated perturbation style of the image. Perturbation styles for a set of images, each having an anatomy label, may be obtained using the encoder 2102 and the perturbation styles may be aggregated, e.g. averaged, to characterize the approach to labeling of a source of the set of images. For example, the images may be images labeled by an individual dental professional or dental professionals in a given geographic region (e.g., city, state, or country).

Figure 22:
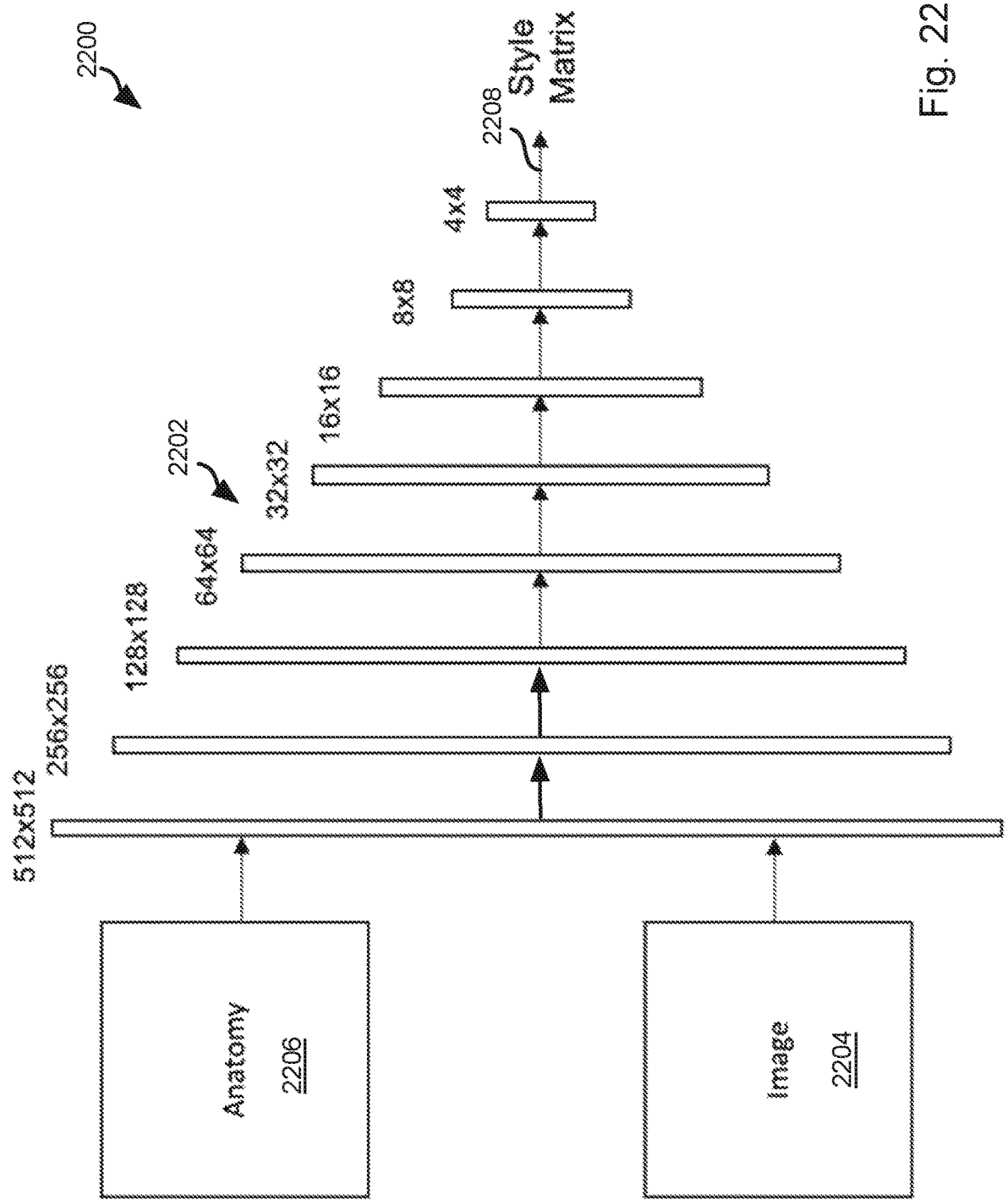
FIG. 22 is a schematic block diagram of another system for identifying perturbations to anatomy labels in accordance with an embodiment of the present invention.

FIG. 22 is a schematic block diagram of another system 2200 for identifying perturbations to anatomy labels in accordance with an embodiment of the present invention. The system 2200 may include an encoder network 2202. The encoder network 2202 may include a number of multi-scale stages with downsampling between them. The encoder network 2202 may be implemented according to any of the approaches described above for implementing a CNN. However, in the illustrated embodiment, the fully connected layer is omitted and the output of the last stage is a matrix of values, such as 4×4 matrix. The encoder 2202 may be an encoder 2102 trained as described above with respect to FIG. 22 except that, following training, the fully connected (FC) layer is removed. Accordingly, an input image 2204 and a label 2206 of anatomy (e.g., pixel mask) are concatenated and processed using the encoder 2202 to obtain a style matrix 2208 that encodes attributes of the label that can be used to characterize a labeling style of the individual that created the label 2206. The encoder 2202 may also be implemented using another machine learning approach, such as random forest, gradient boosting, or support vector machine.

Style matrices may be obtained for a set of images, each having an anatomy label, using the encoder 2202 and the style matrices may be aggregated, e.g. averaged, to characterize the approach to labeling of a source of the set of images. For example, the images may be images labeled by an individual dental professional or dental professionals in a given geographic region (e.g., city, state, or country).

Figure 23:
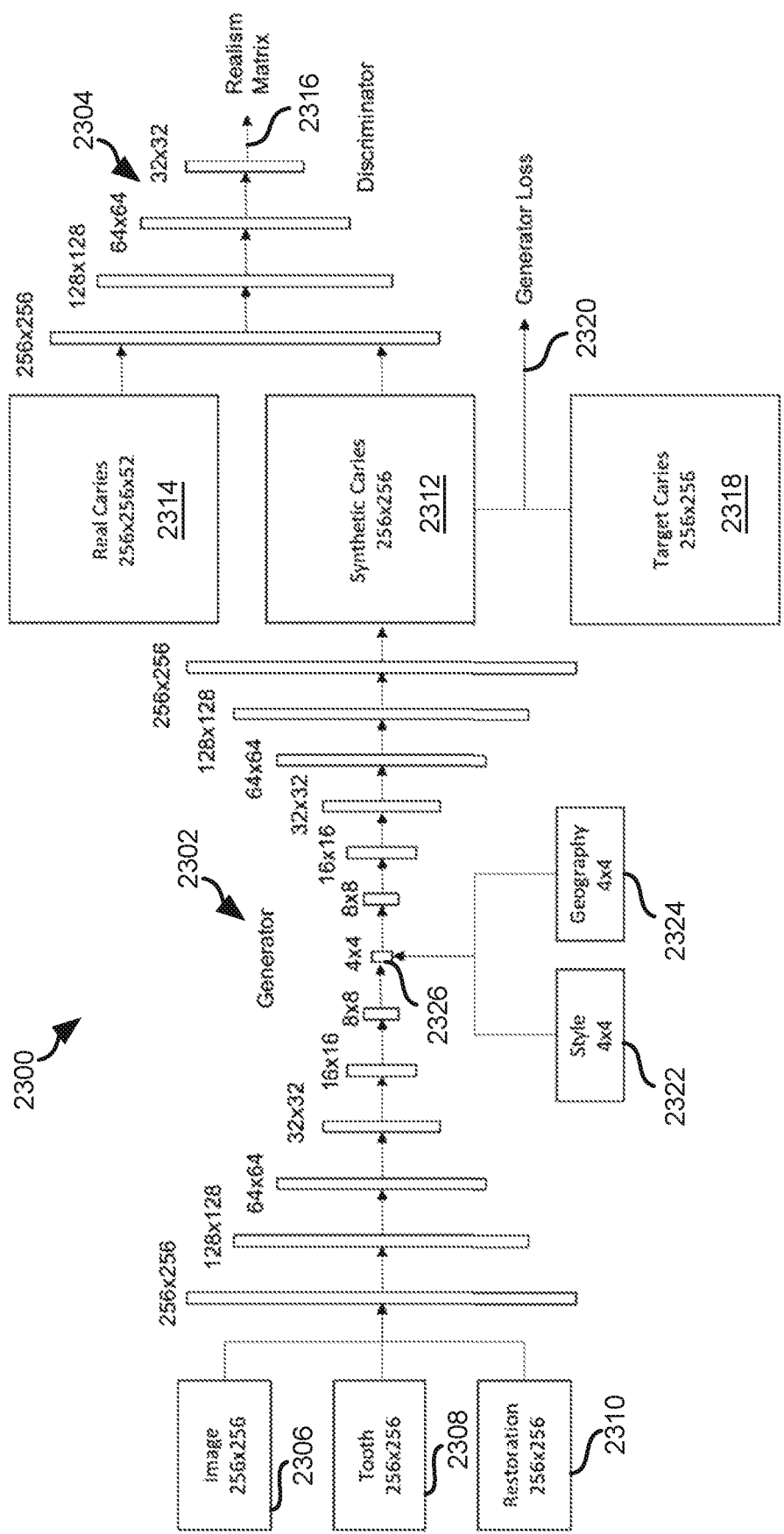
FIG. 23 is a schematic block diagram of a system for identifying caries based on anatomy labeling style in accordance with an embodiment of the present invention.

FIG. 23 is a schematic block diagram of a system 2300 for identifying caries based on anatomy labeling style in accordance with an embodiment of the present invention. The system 2300 includes a generator 2302 coupled to a discriminator 2304. The generator 2302 may be an encoder-decoder and the discriminator 2304 may be an encoder. The generator 2302 and discriminator 2304 may be implemented and trained using any of the approaches described herein for implementing a generator and discriminator of a GAN, such as using CNNs. Other machine learning approaches may also be used, such as random forest, gradient boosting, or support vector machine.

The generator 2302 takes as inputs an image 2306, a tooth label 2308 (e.g., pixel mask showing pixels representing a tooth), and a restoration label 2310 (e.g., pixel mask showing pixels representing a restoration on the tooth). These inputs are concatenated and processed using the generator 2302 to obtain a synthetic caries label 2312, e.g. a pixel mask showing one or more caries corresponding to the dental image, tooth of interest, and corresponding restoration represented by the label 2310, 2308, 2306. The synthetic caries label 2312 may be input with a real caries label 2314 to the discriminator 2404. The real caries label 2314 may be a pixel mask for one or more caries represented in an unpaired dental image (not the image 2306 or an image of the same anatomy represented in the image 2306). The synthetic caries label 2312 and real caries label 2314 are input to the discriminator 2304 that outputs a realism matrix 2316 such that each value of the realism matrix is an estimate as to which of the labels 2312, 2314 is real. As for other embodiments described herein, an aggregation (average, most frequent estimate) may be used by a loss function of the training algorithm.

The synthetic caries label 2312 may also be compared to a target caries label 2318 that is a pixel mask labeling one or more caries representing a ground truth caries label. The result of this comparison is a generator loss 2320 that increases with increase in differences between the labels 2312, 2318. Accordingly, the generator 2302 may be trained by a training algorithm that adjusts the generator 2302 to reduce the generator loss 2320 and to increase the likelihood that the realism matrix 2316 will indicate that the synthetic caries 2312 are real. The training algorithm likewise trains the discriminator 2304 to correctly identify the synthetic caries labels 2312 as fake. Training may continue until the generator loss 2320 converges and the discriminator 2304 cannot distinguish between the synthetic and real caries labels 2312, 2314 or Nash equilibrium is reached.

As shown in FIG. 23, training may additionally be performed with reference to an individual style matrix 2322 (style matrix for an individual labeler) and/or a geography style matrix 2324 (style matrix for labelers within a geographic region) of a training data entry. The matrices 2322, 2324 may be obtained using the system 2200 for the labeler that generated the target caries labels 2318 for the images 2306. The style matrices 2322, 2324 may be concatenated with one another and with an output of one of the stages of the generator 2302 and the result of the concatenation may then be input to the next stage of the generator 2302. For example, the matrices 2322, 2324 may be concatenated with the output of the stage 2326 that is the last stage of the encoder and the first stage of the decoder of the generator 2302.

During training, each training data entry may therefore include as inputs image 2306, a tooth label 2308, restoration label 2310, and one or both of a style matrix 2322 and geography style matrix 2324 for the labeler that generated the labels 2308, 2310, 2318. Each training data entry may also include a target caries label 2318 as a desired output of the training data entry. In this manner, the generator 2302 is trained to identify caries while taking into account variations in labeling behaviors of individuals and populations in a given geographic area.

Figure 24:
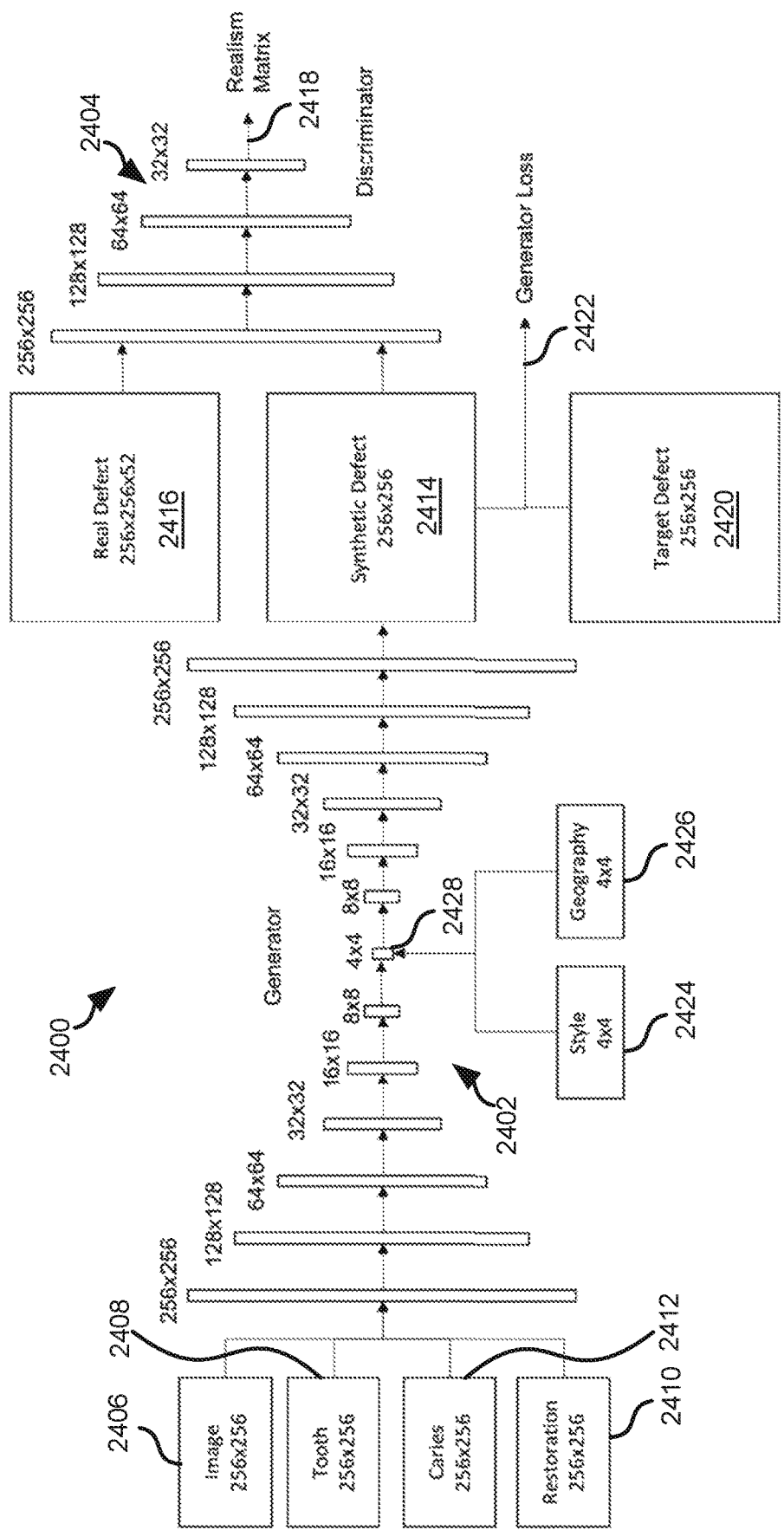
FIG. 24 is a schematic block diagram of a system for detecting defects in a restoration in accordance with an embodiment of the present invention.

FIG. 24 is a schematic block diagram of a system 2400 for detecting defects in a restoration in accordance with an embodiment of the present invention. The system 2400 includes a generator 2402 coupled to a discriminator 2404. The generator 2402 may be an encoder-decoder and the discriminator 2404 may be an encoder. The generator 2402 and discriminator 2404 may be implemented and trained using any of the approaches described herein for implementing a generator and discriminator of a GAN, such as CNNs. Other machine learning approaches may also be used, such as random forest, gradient boosting, or support vector machine.

The generator 2402 takes as inputs an image 2406, a tooth label 2408 (e.g., pixel mask showing pixels representing a tooth), and a restoration label 2410 (e.g., pixel mask showing pixels representing a restoration on the tooth), and a caries label 2412 (e.g., pixel mask showing pixels representing one or more caries repaired by the restoration shown by the label 2410). These inputs are concatenated and processed using the generator 2402 to obtain a synthetic defect label 2414, e.g. a pixel mask showing defects in the restoration shown by label 2410. Defects in a restoration, such as a filling, crown, root canal, veneer, or other restoration may include erosion around the edges of a filling, decay around a crown, a root canal that is not sufficiently deep, endodontic disease around a root canal, void or open contact around the filling or crown, fracture of the filling or crown, incorrect fitting of a crown or filling, compromised restoration material such as the liner or base, or other decay around the restoration.

The synthetic defect label 2414 may be input with a real defect label 2416 to the discriminator 2404. The real defect label 2416 may be a pixel mask for one or more defects represented in an unpaired dental image (not the image 2406 or an image of the same anatomy represented in the image 2406). The synthetic defect label 2414 and real caries label 2416 are input to the discriminator 2404 that outputs a realism matrix 2418 such that each value of the realism matrix is an estimate as to which of the labels 2414, 2416 is real.

The synthetic defect label 2414 may also be compared to a target defect label 2420 that is a pixel mask labeling one or more defects of the restoration represented in the restoration label 2410. The result of this comparison is a generator loss 2422 that increases with increase in differences between the labels 2414, 2420. Accordingly, the generator 2402 may be trained by a training algorithm that adjusts the generator 2402 to reduce the generator loss 2422 and to increase the likelihood that the realism matrix 2316 will indicate that the synthetic defect labels 2414 are real. The training algorithm likewise trains the discriminator 2404 to correctly identify the synthetic defect labels 2414 as fake. Training may continue until the generator loss 2422 converges and the discriminator 2404 cannot distinguish between the synthetic and real defect labels 2414, 2416 or Nash equilibrium is reached.

As shown in FIG. 24, training may additionally be performed with reference to an individual style matrix 2424 (style matrix for an individual labeler) and/or a geography style matrix 2426 (style matrix for labelers within a geographic region) of a training data entry. The matrices 2424, 2426 may be obtained using the system 2200 for the labeler that generated the target defect labels 2420 for the images 2406. The style matrices 2424, 2426 may be concatenated with one another and with an output of one of the stages of the generator 2402 and the result of the concatenation may then be input to the next stage of the generator 2402. For example, the matrices 2424, 2426 may be concatenated with the output of the stage 2428 that is the last stage of the encoder and the first stage of the decoder of the generator 2402.

During training, each training data entry may therefore include as inputs an image 2406, a tooth label 2408, restoration label 2410, caries label 2412, and one or both of a style matrix 2424 and geography style matrix 2426 for the labeler that generated the labels 2408, 2410, 2412, 2420. Each training data entry may also include a target defect label 2420 as the desired output of the training data entry. In this manner, the generator 2402 is trained to identify defects in restorations while taking into account variations in labeling behaviors of individuals and populations in a given geographic area.

Figure 25:
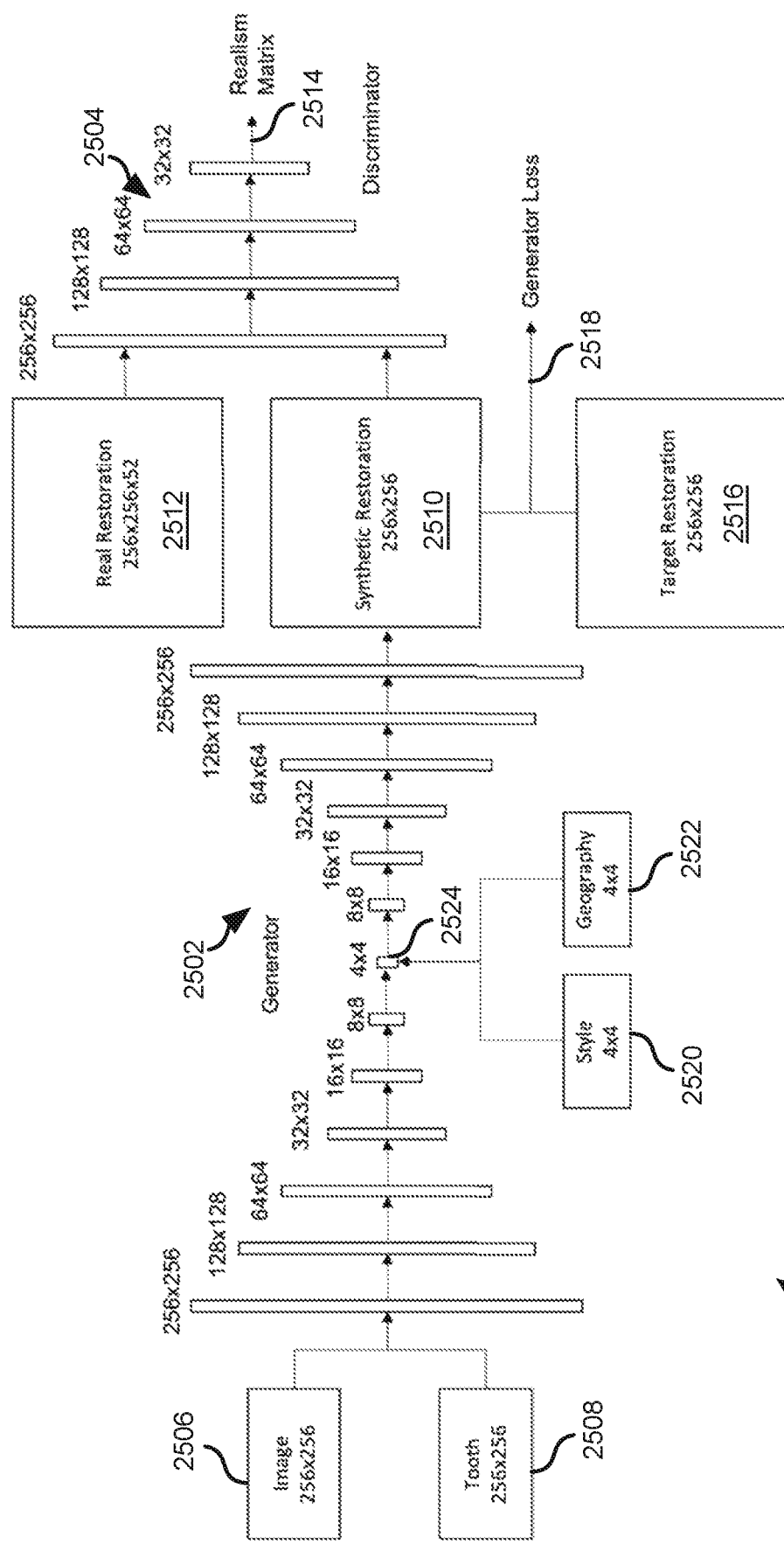
FIG. 25 is a schematic block diagram of a system for selecting a restoration for a tooth in accordance with an embodiment of the present invention.

FIG. 25 is a schematic block diagram of a system 2500 for selecting a restoration for a tooth in accordance with an embodiment of the present invention. The system 2500 includes a generator 2502 coupled to a discriminator 2504. The generator 2502 may be an encoder-decoder and the discriminator 2504 may be an encoder. The generator 2502 and discriminator 2504 may be implemented and trained using any of the approaches described herein for implementing a generator and discriminator of a GAN, such as CNNs. Other machine learning approaches may also be used, such as random forest, gradient boosting, or support vector machine.

The generator 2502 takes as inputs an image 2506 and a tooth label 2508 (e.g., pixel mask showing pixels representing a tooth). These inputs are concatenated and processed using the generator 2502 to obtain a synthetic restoration label 2510, e.g. a pixel mask showing an area for which a restoration is estimated for the tooth represented by the label 2508 and the input image represented by label 2506.

The synthetic restoration label 2510 may be input with a real restoration label 2512 to the discriminator 2504. The real restoration label 2512 may be a pixel mask of the area occupied by one or more restorations represented in an unpaired dental image (not the image 2506 or an image of the same anatomy represented in the image 2506). The synthetic restoration label 2510 and real restoration label 2512 are input to the discriminator 2504 that outputs a realism matrix 2514 such that each value of the realism matrix is an estimate as to which of the labels 2510, 2512 is real.

The synthetic restoration label 2510 may also be compared to a target restoration label 2516 that is a pixel mask labeling the area occupied by one or more restorations actually performed on the tooth labeled by the tooth label 2508.

The result of this comparison is a generator loss 2518 that increases with increase in differences between the labels 2510, 2516. Accordingly, the generator 2502 may be trained by a training algorithm that adjusts the generator 2502 to reduce the generator loss 2518 and to increase the likelihood that the realism matrix 2514 will indicate that the synthetic restoration labels 2510 are real. The training algorithm likewise trains the discriminator 2504 to correctly identify the synthetic restoration labels 2510 as fake. Training may continue until the generator loss 2518 converges and the discriminator 2504 cannot distinguish between the synthetic and real restoration labels 2510, 2512 or Nash equilibrium is reached.

As shown in FIG. 25, training may additionally be performed with reference to an individual style matrix 2520 (style matrix for an individual labeler) and/or a geography style matrix 2522 (style matrix for labelers within a geographic region) of a training data entry. The matrices 2520, 2522 may be obtained using the system 2200 for the labeler that generated the target restoration labels 2516 for the images 2506. The style matrices 2520, 2522 may be concatenated with one another and with an output of one of the stages of the generator 2502 and the result of the concatenation may then be input to the next stage of the generator 2502. For example, the matrices 2520, 2522 may be concatenated with the output of the stage 2524 that is the last stage of the encoder and the first stage of the decoder of the generator 2502.

During training, each training data entry may therefore include as inputs an image 2506, tooth label 2508, and one or both of a style matrix 2520 and geography style matrix 2522 for the labeler that generated the labels 2508, 2516. Each training data entry may also include a target restoration label 2516 as the desired output for the training entry. In this manner, the generator 2502 is trained to select an appropriate restoration for a tooth while taking into account variations in labeling behaviors of individuals and populations in a given geographic area.

Figure 26:
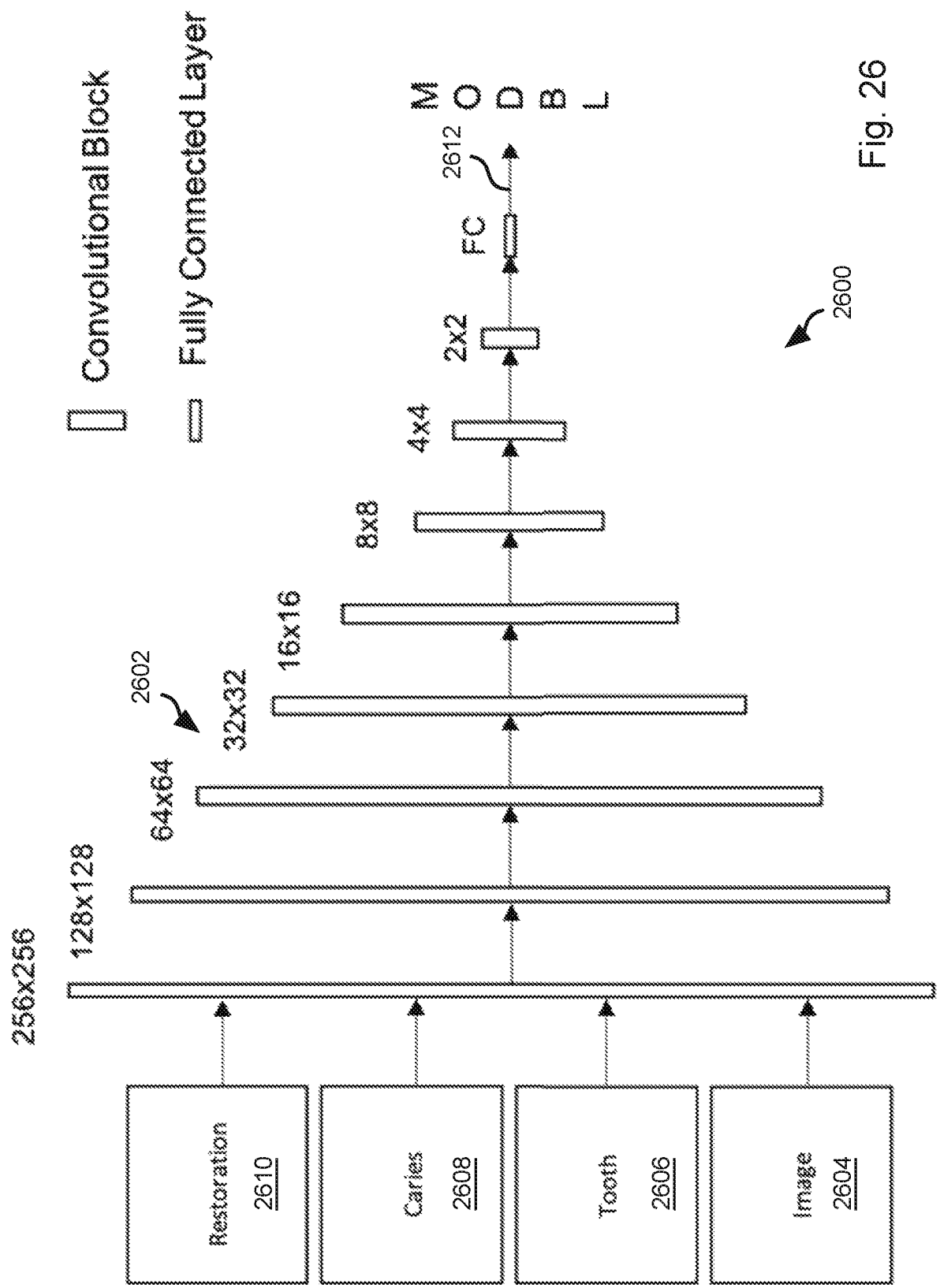
FIG. 26 is a schematic block diagram of a system for identifying surfaces of a tooth having caries in accordance with an embodiment of the present invention.

FIG. 26 is a schematic block diagram of a system 2600 for identifying surfaces of a tooth having caries in accordance with an embodiment of the present invention. Caries are often identified by evaluating two-dimensional images, such as X-rays. It may not always be apparent from an X-ray which surface of a tooth bears a carious lesion. For example, an apparent carious lesion may be on the surface facing the viewer or away from the viewer.

The illustrated system 2600 may be used to estimate the surface of a tooth in which caries are present. As known in the field of dentistry, these surfaces may be the mesial (facing forward), occlusal (chewing surface), distal (facing rearward), buccal (facing toward the cheek), and lingual (facing toward the tongue) (designated herein as M, O, D, B, and L, respectively).

The system 2600 may include an encoder network 2602. The encoder network 2602 may include a number of multi-scale stages with downsampling between them with the last stage coupled to a fully connected layer. The encoder network 2602 may be implemented according to any of the approaches described above for implementing a CNN. Other machine learning approaches may also be used, such as random forest, gradient boosting, or support vector machine.

Training data entries may each include an image 2604, such as an image of dental anatomy according to any of the imaging modalities described herein. Each training data entry may further include a tooth label 2606 (pixel mask indicating portion of image 2604 representing a tooth), caries label 2608 (pixel mask indicating portions of the image 2604 corresponding to one or more caries on the tooth indicated by the label 2606), and a restoration label 2610 (pixel mask indicating portions of the image 2604 representing any previous restoration performed with respect to the caries on the tooth represented by the label 2606).

The image 2604 and labels 2606-2610 may be concatenated and processed using the encoder 2602. The encoder 2602 then generates an output 2612 that is a surface label having one of five values, each corresponding to one of the five surfaces (M, O, D, B, L) of a tooth. Accordingly, each training data entry may include an image 2604 and labels 2606-2610 as inputs. The desired output for each training data entry may be a surface label indicating the surface (M, O, D, B, L) on which the caries indicated in the label 2608 are formed. The training algorithm may therefore train the encoder 2602 to output a surface label for caries for a given input image 2604 and corresponding labels 2606-2610 corresponding to those caries.

Figure 27:
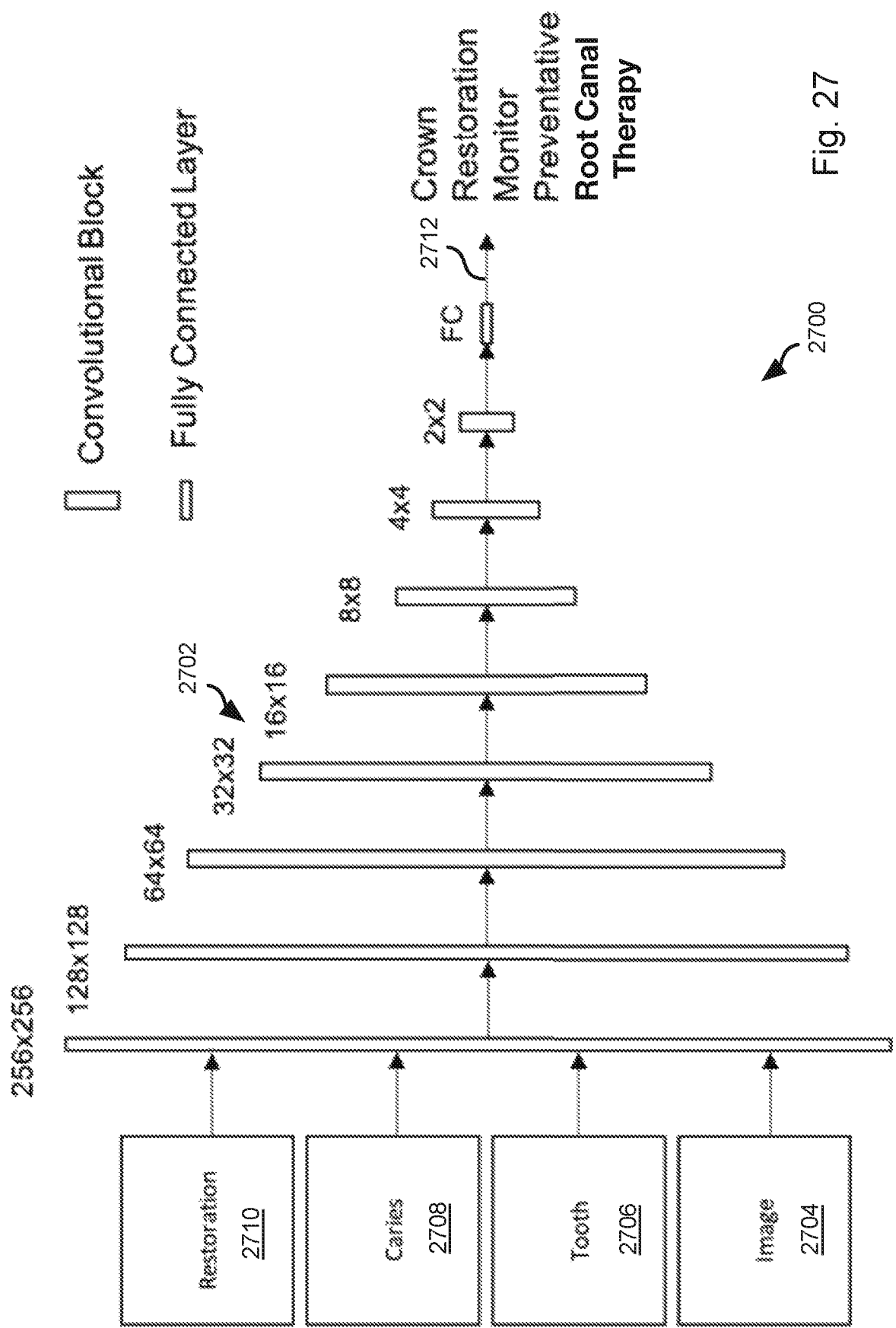
FIG. 27 is a schematic block diagram of a system for selecting dental treatments in accordance with an embodiment of the present invention.

FIG. 27 is a schematic block diagram of a system 2700 for selecting dental treatments in accordance with an embodiment of the present invention. Dental treatments may include such treatments as a crown, restoration (e.g., filling), monitoring, preventative care, root canal therapy, scaling and root planing per tooth or by oral quadrant, extraction, orthodontic treatment addressing malocclusion, oral surgical intervention, and prosthodontic treatment, and root canal therapy. The system 2700 may also be used for selecting orthodontic treatments such as described in U.S. Provisional Application Ser. No. 62/916,966 filed Oct. 18, 2019, and entitled Systems and Methods for Automated Orthodontic Risk Assessment, Medical Necessity Determination, and Treatment Course Prediction.

The system 2700 may include an encoder network 2702. The encoder network 2702 may include a number of multi-scale stages with downsampling between them with the last stage coupled to a fully connected layer. The encoder network 2702 may be implemented according to any of the approaches described above for implementing a CNN. Other machine learning approaches may also be used, such as random forest, gradient boosting, or support vector machine.

Training data entries may each include an image 2704, such as an image of dental anatomy according to any of the imaging modalities described herein. Each training data entry may further include a tooth label 2706 (pixel mask indicating portion of image 2604 representing a tooth), caries label 2708 (pixel mask indicating portions of the image 2704 corresponding to one or more caries on the tooth indicated by the label 2706), and a restoration label 2710 (pixel mask indicating portions of the image 2704 representing any prior restoration performed with respect to the tooth indicated by the tooth label 2706)). In this manner, additional treatments needed to fix a prior restoration may be identified.

The image 2704 and labels 2706-2710 may be concatenated and processed using the encoder 2702. The encoder 2702 then generates an output 2712 that is a treatment estimate, e.g. a numerical value corresponding to a treatment. Accordingly, each training data entry may include an image 2704 and labels 2706-2710 as inputs. The desired output for each training data entry may be a treatment option, e.g. the numerical value corresponding to the appropriate treatment option for the caries indicated by the label 2708. The training algorithm may therefore train the encoder 2702 to output a treatment estimate for a given input image 2704 and corresponding labels 2706-2710.

Figure 28:
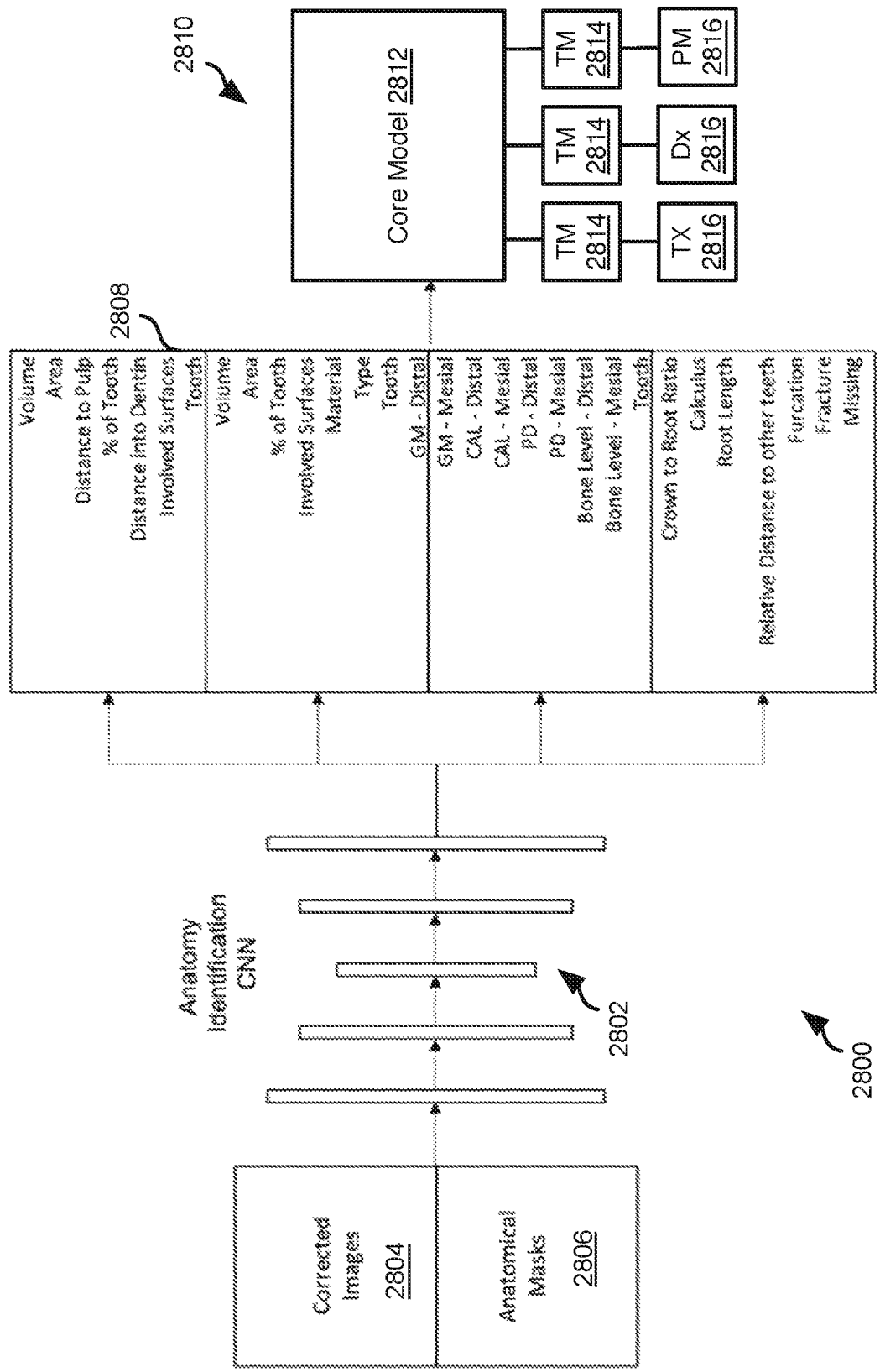
FIG. 28 is a schematic block diagram of a system for selecting a diagnosis, treatment, or patient match in accordance with an embodiment of the present invention.

FIG. 28 is a schematic block diagram of a system 2800 for selecting a diagnosis, treatment, or patient match in accordance with an embodiment of the present invention. In particular, treatments may include a selection of a treatments for caries based on the extent and depth of the caries. Such treatments may include a filling, multiple fillings, a crown, restoration, monitoring, preventative care, root canal therapy, or extraction. As another example, the dental pathology may include endodontic disease, e.g., carious lesions in bone such that a treatment may include tooth extraction. In another example, the presence of decay in bone around a tooth may be used to determine whether to do a crown, root canal, or extraction. In yet another example, decay around a previous restoration (e.g., filling or crown) or treatment (e.g., root canal therapy) may be used to determine an appropriate additional treatment such as root canal therapy, extraction, or additional root canal therapy. The system 2800 may also be used for diagnosing orthodontic conditions and selecting orthodontic treatments such as described in U.S. Provisional Application Ser. No. 62/916, 966 filed Oct. 18, 2019, and entitled Systems and Methods for Automated Orthodontic Risk Assessment, Medical Necessity Determination, and Treatment Course Prediction.

The system 2800 may include an anatomy identification machine learning model 2802, which may be embodied by a CNN, such as an encoder-decoder CNN according to any of the embodiments disclosed herein. The machine learning model 2802 may also be implemented using other machine learning approaches such as such as random forest, gradient boosting, or support vector machine.

The machine learning model 2802 takes as inputs an image 2804, which may be an image corrected according to any of the approaches described herein (reoriented, decontaminated, transformed, inpainted). The machine learning model 2802 may further take as an input one or more anatomical masks 2806 for the image 2804. The anatomical masks 2806 may be pixels masks labeling anatomy represented in the image 2804. The anatomical masks 2806 may identify any of the dental anatomy described herein, such as teeth, CEJ, GM, JE, bony points, caries, periapical line, or other dental anatomy. The anatomical masks 2806 may label dental pathologies such as caries, carious lesions in bone, or other dental pathologies. The anatomical masks 2806 may label previous restorations such as fillings, crowns, root canal therapy, or other restorations. The anatomical masks 2806 may be generated by a trained dental professional or generated using a machine learning model trained and utilized as described herein. Images 2804 and corresponding anatomical masks 2806 may be generated and stored in a database for later processing using the machine learning model 2802 or other machine learning models described herein.

The image 2804 and the one or more anatomical masks 2806 may be concatenated and processed using the machine learning model 2802. The machine learning model 2802 may be trained to output measurements 2808 of the anatomy labeled by the masks. Accordingly, training data entries may each include an image 2804 and one or more anatomical masks 2806 as inputs and one or more measurements as desired outputs. The training algorithm may then train the machine learning model 2802 to output a measurement for a given input image 2804 and corresponding anatomical masks 2806.

The machine learning model 2802 may be multiple models, each being trained to output a particular measurement or group of measurements. The measurements of an item of anatomy may include its center of mass, relative distance to other anatomy, size distortion, and density. Measurements for caries may include volume, area, distance to pulp, percent of tooth covered by it, distance into dentin, involved surfaces of the tooth (M, O, D, B, L), and identifier of the affected tooth. Measurements of fillings or other restorations on teeth may include volume, area, percent of tooth covered by it, involved surfaces of the tooth (M, O, D, B, L), material, type, and identifier of the affected tooth. Measurements of periodontal anatomy may include distal gingival margin, mesial gingival margin, distal CAL, mesial CAL, distal PD, mesial PD, distal bone level, mesial bone level, and the identifier of the tooth for which the periodontal anatomy is identified and measured. Measurements relating to root canal therapy at a given tooth position may include crown-to-root-ratio, calculus, root length, relative distance to adjacent teeth, furcation, fracture, and whether the tooth at that tooth position is missing.

The measurements 2808 may then be processed by a machine learning model 2810 to perform one or more tasks such as obtaining a diagnosis, determining an appropriate treatment, or identifying a patient that matches the measurements 2808. Identifying a matching patient may be helpful in claim adjudication to determine how a claim involving a similar patient was decided.

In some embodiments, the machine learning model 2810 is a dense neural network including two layers. In some embodiments, the first layer has 1000 parameters and the second network has 100 parameters. The head of the network (core model 2812) may be separate from the rest of the network (task models 2814) and trained separately. Data may be processed by the core model 2812 followed by the output of the core model 2812 being processed by the task models 2814, each task model 2814 outputting an estimate 2816 corresponding to the task it is being trained to perform.

For example, the machine learning model 2810 may be trained according to a multitask training algorithm. The training algorithm may proceed as follows:

(Step 1) The core model 2812 and a first task model 2814 are trained to perform the task corresponding to the first task model 2814 (treatment identification in the illustrated embodiment).

(Step 2) The other task models 2814 are trained to perform their corresponding tasks one at a time without changing the core model 2812 (diagnosis determination and patient matching models 2814 in the illustrated embodiment).

(Step 3) Each of the task models 2814 is trained individually again except that the training at this step includes further training of the core model 2812.

(Step 4) The core model 2814 is trained to perform the tasks corresponding to each of the task models 184 in combination with the task models 2814 except that only the core model 2812 is modified and the task models 2814 are maintained fixed. Step 4 may include processing data sets for each task in series. E.g., data set for task 1 is processed using the core model 2812 and the task model 2814 for task 1, the data set for task 2 is processed using the core model 2812 and the task model 2814 for task 2, and so on for each task with only the core model 2812 being modified during the training.

For the treatment identification task, the training data entries may each include an image 2804 and anatomical masks 2806 as inputs and an appropriate treatment as determined by a dental professional as a desired output. Likewise, the training data entries for diagnosis determination may each include an image 2804 and anatomical masks 2806 as inputs and an appropriate diagnosis as determined by a dental professional as a desired output. For patient matching, training data entries may each include an image 2804 and anatomical masks 2806 as inputs and a vector or matrix of characterizing values as a desired output. Accordingly, the core model 2812 and task model 2814 for the patient matching tasks may function as an autoencoder. The vector or matrix of characterizing values being such that they may be compared to a database of patient records to identify another patient that has a similar vector or matrix. Similarity may be measured using cosign difference measurements or other approach.

Once trained, the system 2800 may be used to evaluated the impact of perturbations to anatomical masks on the output of the machine learning model 2812. Specifically, one or more masks 2806 for an image 2804 may be perturbed according to a first perturbation style (e.g., as defined by a perturbation matrix or a perturbation value processed by a perturbation algorithm to modify the mask 2806). The image 2804 and masks 2806 having one or more masks replaced with the perturbed masks may be processed using the machine learing model 2802 to obtain measurements 2808, which are then processed using machine learning model 2810 to obtain first outputs for one or more tasks of the machine learning model 2810.

The process of the preceding paragraph may be repeated for a second perturbation style that is different from the first perturbation style to obtain second outputs from the machine learning model 2810 for one or more tasks of the machine learning model 2810. The user may then compare the outputs for the first and second perturbations styles to determine how the perturbation style impacts diagnosis determination, treatment identification, and/or patient matching.

In some embodiments a system may include an interface that may be displayed to a user and include user interface elements enabling the user to adjust perturbation styles, such as amount of erosion or dilation or amount of boundary roughening or smoothing to apply. The system may then generate a perturbation style corresponding to the amounts specified by the user and apply the perturbation style to an anatomical mask. The user may therefore experiment with perturbation styles and determine how they affect diagnosis determination, treatment identification, and/or patient matching.

The interface may further provide interface elements allowing the user to individually specify the amounts of perturbation for each type of anatomical mask 2806, e.g. each item of anatomy represented by one of the anatomical masks 2806. The user may therefore amplify or diminish the impact of a particular anatomical mask 2806 on the output of the machine learning model 2810. For example, a user might find that if they change the pulp, enamel, bone, gingival margin, CEJ, tooth, or caries masks, the output treatment, diagnosis, or patient match might correspond better with the user's own stylistic preferences.

In some embodiments, a perturbation style selected by a user may be input by concatenating a style matrix corresponding to the perturbation style with an inner stage of the machine learning model 2802, such as using the approach described above with respect to FIG. 24.

Figure 29:
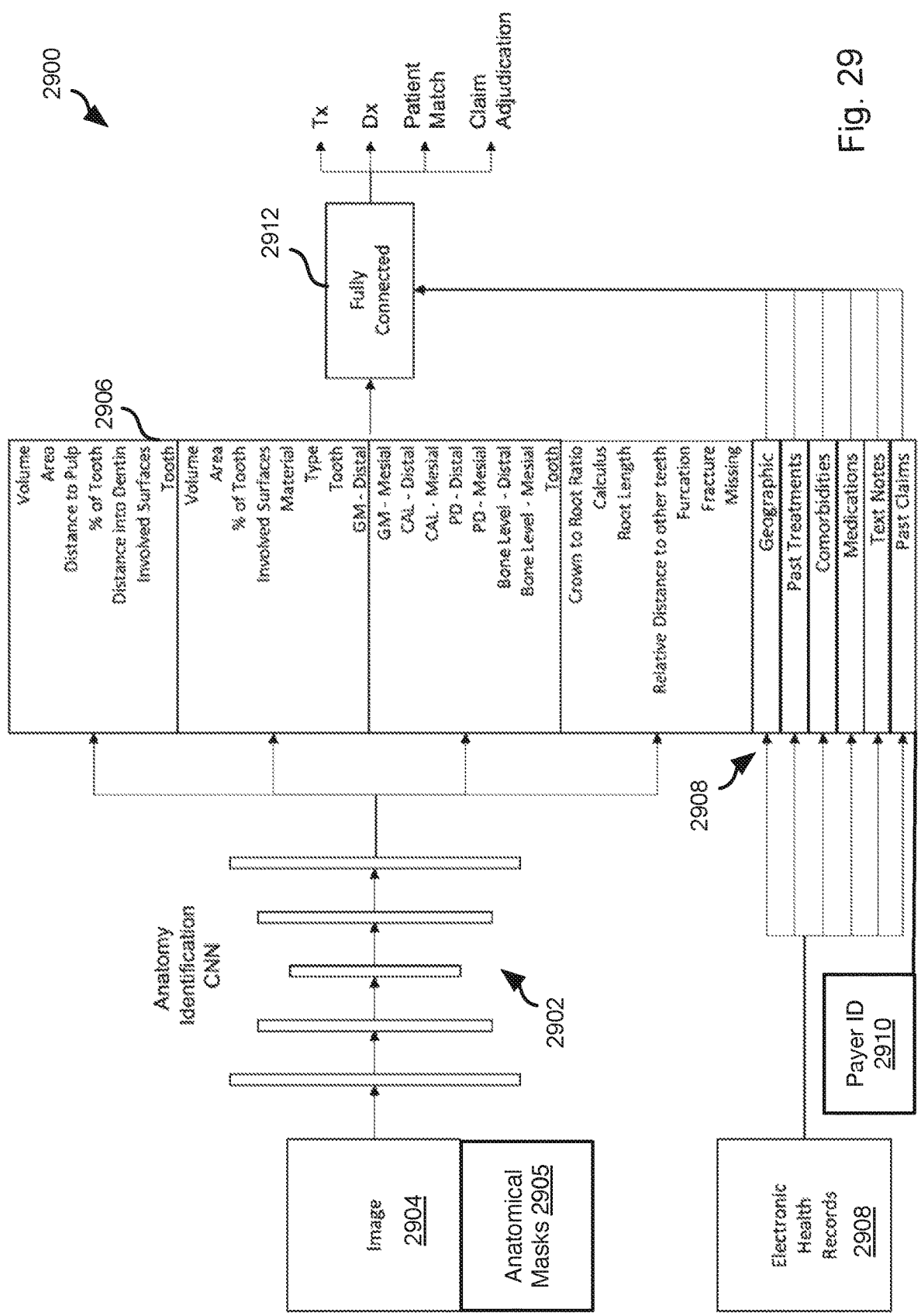
FIG. 29 is a schematic block diagram of a system for predicting claim adjudication in accordance with an embodiment of the present invention.

FIG. 29 is a schematic block diagram of a system 2900 for predicting claim adjudication according to a treatment plan in accordance with an embodiment of the present invention. The treatments for which a claim adjudication may be predicted may include any of the treatments for any of the diagnosis of a dental, periodontal, or orthodontic condition, such as any of the treatments for any of the dental, periodontal, or orthodontic condition described herein.

Determining the most appropriate care for a dental patient is often a balance between competing objectives. A patient might present anatomy necessitating aggressive intervention, but the patient's dental insurance plan might only cover a less invasive procedure. To allocate clinical resources efficiently, it is often useful to know how a procedure will be adjudicated by a payer network. Having clarity on payer decision making would enable a more streamlined clinical workflow. However, payer claim adjudication decisions can change from day-to-day. Also, different payers have different adjudication tendencies and timelines, which makes it very difficult for dentists to determine optimal patient care.

To solve this problem, an automated treatment likelihood system 2900 may be trained and used to predict payer decisions with respect to a particular treatment. The system 2900 may include an anatomy identification machine learning model 2802, which may be embodied by a CNN, such as an encoder-decoder CNN according to any of the embodiments disclosed herein. The machine learning model 2902 may also be implemented using other machine learning approaches such as such as random forest, gradient boosting, or support vector machine.

The machine learning model 2802 takes as inputs an image 2904, which may be an image corrected according to any of the approaches described herein (reoriented, decontaminated, transformed, inpainted). In some embodiments, anatomical masks as described above with respect to the system 2800 are omitted. However, in other embodiments, the input to the machine learning model 2902 may include the image 2904 concatenated with one or more anatomical masks 2905.

The machine learning model 2902 may be trained to output measurements 2906 of anatomy represented in the image 2904 and possibly the anatomical masks 2905 for the image 2904. The measurements may include some or all of the measurements described above as being output by the machine learning model 2802. The machine learning model 2902 may be trained in the manner described above with respect to the machine learning model 2802.

The measurements 2906 may be combined with one or more items of metadata 2908 relating to the patient whose anatomy is represented in the image 2904. The metadata may be in text form and may be extracted from patient records, such as clinical notes in patient records. The metadata may include such information as age, comorbidities, past treatments, past diagnosis, past periodontal chart, past odontogram, geography, medications, other text notes, and past claims. The measurements 2906 may also be combined with an identifier 2910 of a payer for which treatment likelihood is to be estimated.

The measurements 2906, metadata 2908, and payer identifier 2910 may be concatenated and input to a machine learning model 2912. The machine learning model may be trained to perform various tasks with respect to the input data. The tasks may include treatment identification, diagnosis determination, and patient match identification as described above with respect to the system 2800. An additional task may include claim adjudication, e.g., a likelihood that a treatment identified will be approved or disapproved by the entity identified by the payer identifier 2910.

Accordingly, training data entries for the machine learning model 2912 may include measurements 2906, metadata 2908, and a payer identifier 2910 as inputs and as a desired output some or all of a treatment identification, diagnosis determination, patient match identification, and a claim adjudication. The claim adjudication may be binary (approved/disapproved) and/or a time value, e.g. an amount of time required before approval. The training algorithm may then train the machine learning model 2912 to perform the tasks using the training data entries. The training algorithm may include performing the multitask training algorithm described above with respect to the machine learning model 2810. The machine learning model 2912 may include a core model and task model for each tasks using the approach described above with respect to the machine learning model 2810.

The machine learning model 2912 may be implemented as a neural network comprised of two dense layers, such as a fully connected network. The number of parameters in each layer may vary depending on the type of imaging modality and anatomical location. Feature distillation may be conducted prior to final training. The final output size may be variable depending on whether the model 2912 is predicting treatment (Tx), diagnosis (Dx), closest historical patient match, or claims adjudication. The fully connected network may be replaced other with machine learning algorithms such a tree-based techniques, gradient boosting, and support vector machines. The alternative machine learning algorithms may also be used in an ensemble method.

Following training, an image 2904 of a patient, and possibly anatomical masks 2905 for the image 2904 may be processed using the machine learning model 2902 to obtain measurements. Measurements 2906, metadata 2908 for the patient, and a payer identifier 2910 may then be processed using the machine learning model 2912 to obtain some or all of a treatment identification, diagnosis determination, closest patient match, or a predicted claim adjudication. In some embodiments, the predicted claim adjudication may include a predicted time before approval.

As for the system 2800, the system 2900 may include an interface that may be displayed to a user and include user interface elements enabling the user to adjust perturbation styles, such as amount of erosion or dilation or amount of boundary roughening or smoothing to apply. The system may then generate a perturbation style corresponding to the amounts specified by the user and apply the perturbation style to an image. The user may therefore experiment with perturbation styles and determine how they affect diagnosis determination, treatment identification, patient matching, or claim adjudication.

The interface may further provide interface elements allowing the user to individually specify the amounts of perturbation for each anatomical mask 2905. The user may therefore amplify or diminish the impact of a particular anatomical mask 2905 on the output of the machine learning models 2902, 2912. For example, a user might find that if they change the pulp, enamel, bone, gingival margin, CEJ, tooth, or caries detection output then the treatment, diagnostic, patient match, or claim adjudication results might correspond better with their own stylistic preferences.

Likewise, on a larger scale, a large number of patient data entries each including an image 2904, anatomical masks 2905, patient metadata 2908, and payer identifier 2910 may be subject to a common perturbation style of one or more masks 2905 to obtain claim adjudication predictions that may be aggregated (e.g., averaged or summed). This may be performed multiple times with different perturbation styles for different types of masks 2905. A user may therefore estimate how a change in the perturbation style of a mask 2905 of a particular anatomical feature could affect claim adjudications in aggregate. The user is thereby enabled to determine how perturbations to a mask 2905 of a particular anatomical feature affects risk of the payer or other party.

In some embodiments, a perturbation style selected by a user may be input to the system 2900 by concatenating a style matrix corresponding to the perturbation style with an inner stage of the machine learning model 2802, such as using the approach described above with respect to FIG. 24.

Figure 30:
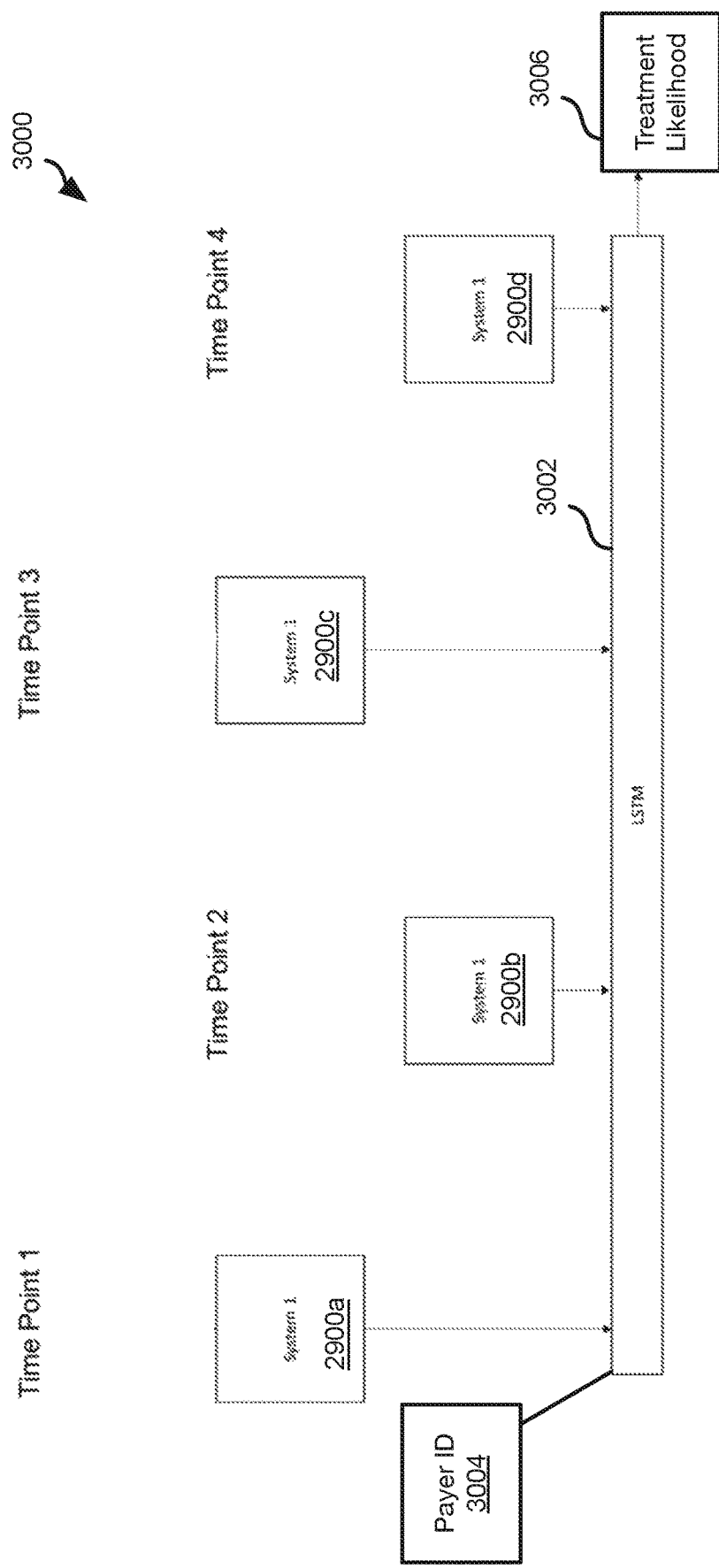
FIG. 30 is a schematic block diagram of a system for predicting a treatment being appropriate based on past treatment in accordance with an embodiment of the present invention.

Referring to FIG. 30, in some embodiments, a system 3000 may be used to determine a likelihood of a treatment being appropriate. The treatments for which likelihood of treatment may be predicted may include any of the treatments for any of the diagnosis of a dental, periodontal, or orthodontic condition, such as any of the treatments for any of the dental, periodontal, or orthodontic condition described herein.

The system 3000 may include a two-layer bi-directional long short-term memory (LSTM) network 3002. The LSTM 3002 takes as inputs the outputs of machine learning models 2900a-2900d. Although four machine learning models 2900a-2900d are shown, the approach described herein may be used with any number of machine learning models 2900a-2900d greater than two. The machine learning models 2900a-2900d may be implemented as a system 2900 as described above except that one or more of the last layers of the machine learning model 2912 are removed and the outputs of the last remaining layer are then input to the LSTM 3002.

The machine learning models 2900a-2900c each take as inputs patient data at for a dental appointment preceding a current claim for which adjudication is being predicted. The patient data for an appointment may include any of the data described above as being input to the machine learning model 2902, such as an image captured during the appointment, anatomic labels for the image, patient metadata as constituted at the time of the appointment. The machine learning model 2900d takes as input the same items of patient data from an appointment for which the likelihood of a treatment is to be determined using the system 3000.

The LTSM 3002 may be trained with historical patient data to output a treatment likelihood 3006. In some embodiments, the treatment likelihood 3006 may be an estimate of approval of payment for a treatment by a payer. Accordingly, an input to the LTSM 3002 may be a payer identifier 3004. Accordingly, a training data entry for training the system 3000 may include the patient data for a plurality of appointments (e.g. a number of appointments equal to the number of machine learning models 2900a-2900d) as an inputs and a treatment approved or denied for the last appointment in the set of appointments as a desired output. Each training data entry may further include a payer identifier 3004 for the payer that approved or denied the treatment. The LTSM 3002 may then be trained by inputting the patient data for each appointment into one of the machine learning models

2900a-2900d. In some embodiments, temporal ordering is preserved, e.g. machine learning model 2900a receives patient data for the earliest appointment, machine learning model 2900b for the next appointment, and so on to the last machine learning model 2900d which receives the patient data for the most recent appointment. The outputs of the machine learning models 2900a-2900d are processed using the LSTM 3002 to obtain a treatment likelihood 3006. The training algorithm then compares a treatment likelihood 3006 output by the LSTM 3002 to the treatment approved or denied as recorded the training data entry and updates the LSTM 3002 according to whether the treatment likelihood matches the treatment approved or denied as recorded in the training data entry.

In use, patient data for a set of appointments may then be input to the machine learning models 2900a-2900d as described above and the outputs of the machine learning models 2900a-2900d input to the LSTM 3002 (possibly with a payment identifier 3004) to obtain a treatment likelihood 3006.

Various alternative embodiments are also possible. For example, in some cases there may be records of some or all of an actual diagnosis, treatment, and claim adjudication for prior appointments. This data along with other patient data (e.g., image, anatomical labels, or anatomy measurements) may be referred to as an appointment data set. The LTSM 3002 may define inputs for a plurality of appointment data sets, with the input for the most recent appointment taking only patient data without data defining a claim adjudication. The LTSM 3002 may then be trained to determine a treatment likelihood, which may be a claim adjudication likelihood, or the last appointment.

As for other embodiments disclosed herein, an interface may be provided to evaluate the impact of perturbations to anatomical labeling on the treatment likelihood 3006. Perturbations for an anatomical label type as input by a user may be implemented with respect to the machine learning models 2900a-2900d as described above with respect to the system 2900. This may include evaluating a financial implication of perturbations on an aggregation of treatment likelihoods for patient data from a large (e.g., 100s or 1000s) set of patients.

Figure 31:
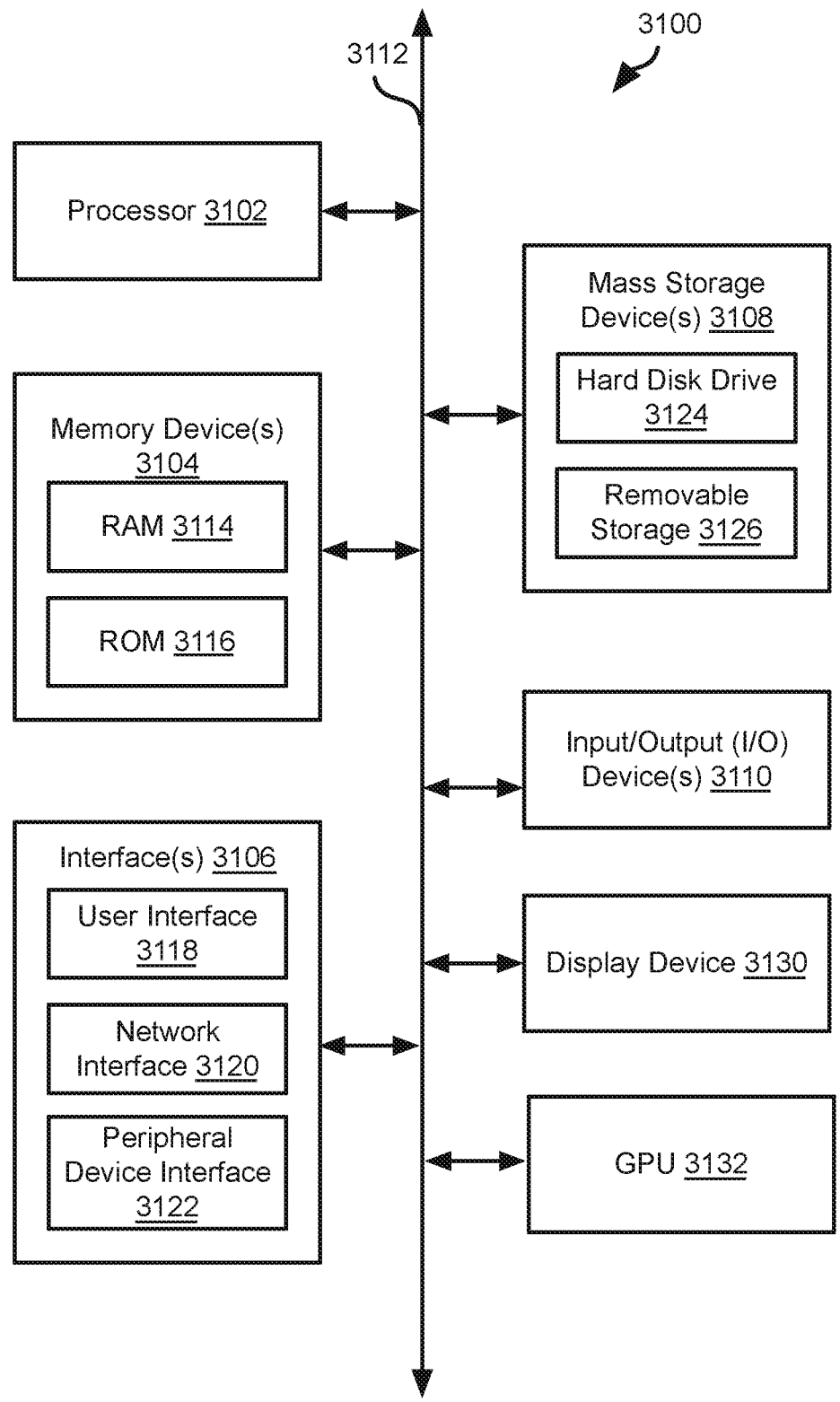
FIG. 31 is a schematic block diagram of a computer system suitable for implementing methods in accordance with embodiments of the present invention.

FIG. 31 is a block diagram illustrating an example computing device 3100 which can be used to implement the system and methods disclosed herein. In some embodiments, a cluster of computing devices interconnected by a network may be used to implement any one or more components of the invention.

Computing device 3100 may be used to perform various procedures, such as those discussed herein. Computing device 3100 can function as a server, a client, or any other computing entity. Computing device can execute one or more application programs, such as the training algorithms and utilization of machine learning models described herein. Computing device 3100 can be any of a wide variety of computing devices, such as a desktop computer, a notebook computer, a server computer, a handheld computer, tablet computer and the like.

Computing device 3100 includes one or more processor(s) 3102, one or more memory device(s) 3104, one or more interface(s) 3106, one or more mass storage device(s) 3108, one or more Input/Output (I/O) device(s) 3110, and a display device 3130 all of which are coupled to a bus 3112. Processor(s) 3102 include one or more processors or controllers that execute instructions stored in memory device(s) 3104 and/or mass storage device(s) 3108.

Processor(s) 3102 may also include various types of computer-readable media, such as cache memory.

Memory device(s) 3104 include various computer-readable media, such as volatile memory (e.g., random access memory (RAM) 3114) and/or nonvolatile memory (e.g., read-only memory (ROM) 3116). Memory device(s) 3104 may also include rewritable ROM, such as Flash memory.

Mass storage device(s) 3108 include various computer readable media, such as magnetic tapes, magnetic disks, optical disks, solid-state memory (e.g., Flash memory), and so forth. As shown in FIG. 31, a particular mass storage device is a hard disk drive 3124. Various drives may also be included in mass storage device(s) 3108 to enable reading from and/or writing to the various computer readable media. Mass storage device(s) 3108 include removable media 3126 and/or non-removable media.

I/O device(s) 3110 include various devices that allow data and/or other information to be input to or retrieved from computing device 3100. Example I/O device(s) 3110 include cursor control devices, keyboards, keypads, microphones, monitors or other display devices, speakers, printers, network interface cards, modems, lenses, CCDs or other image capture devices, and the like.

Display device 3130 includes any type of device capable of displaying information to one or more users of computing device 3100. Examples of display device 3130 include a monitor, display terminal, video projection device, and the like.

A graphics-processing unit (GPU) 3132 may be coupled to the processor(s) 3102 and/or to the display device 3130, such as by the bus 3112. The GPU 3132 may be operable to perform convolutions to implement a CNN according to any of the embodiments disclosed herein. The GPU 3132 may include some or all of the functionality of a general-purpose processor, such as the processor(s) 3102.

Interface(s) 3106 include various interfaces that allow computing device 3100 to interact with other systems, devices, or computing environments. Example interface(s) 3106 include any number of different network interfaces 3120, such as interfaces to local area networks (LANs), wide area networks (WANs), wireless networks, and the Internet. Other interface(s) include user interface 3118 and peripheral device interface 3122. The interface(s) 3106 may also include one or more user interface elements 3118. The interface(s) 3106 may also include one or more peripheral interfaces such as interfaces for printers, pointing devices (mice, track pad, etc.), keyboards, and the like.

Bus 3112 allows processor(s) 3102, memory device(s) 3104, interface(s) 3106, mass storage device(s) 3108, and I/O device(s) 3110 to communicate with one another, as well as other devices or components coupled to bus 3112. Bus 3112 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 3100, and are executed by processor(s) 3102. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

The invention claimed is:

1. A method for training a machine learning model comprising:
   providing, on the computer system, a plurality of first dental images;
   providing, on a computer system, a random mask for each image of the plurality of first dental images;
   processing, by the computer system, each image of the plurality of first dental images and the random mask for the each image with a generator machine learning model to obtain an inpainted image for the each image, the inpainted image including image data generated by the generator machine learning model for image locations corresponding to the random mask for the each image; and
   for each image of the plurality of first dental images, updating, by the computer system, the generator machine learning model according to a training algorithm according to similarity of the each image to the inpainted image obtained for the each image;
   wherein each image of the plurality of first dental images is an image of dental anatomy according to an imaging modality selected from the group consisting of full mouth series X-rays, dental cone beam computed tomography (CBCT), cephalometric X-ray, intra-oral optical image, panoramic dental X-ray, dental magnetic resonance imaging (MRI) image, dental light detection and ranging (LIDAR) image.

2. The method of claim 1, further comprising:
   processing, by the computer system, the inpainted image for each first dental image of the plurality of first dental images and an unpaired dental image from a repository using a discriminator machine learning model to obtain a realism estimate; and
   updating, by the training algorithm, the generator machine learning model and the discriminator machine learning model according to the realism estimates for the plurality of first dental images.

3. The method of claim 2, wherein the generator machine learning model is an encoder-decoder machine learning model.

4. The method of claim 3, wherein the generator machine learning model and the discriminator machine learning model are each convolution neural networks.

5. The method of claim 2, wherein the realism estimate is a matrix of realism estimates.

6. The method of claim 1, further comprising:
   processing, by the computer system, a second dental image using the generator machine learning model to obtain a utilization inpainted image; and
   processing, by the computer system, the utilization inpainted image according to a labeling machine learning model to obtain labels of dental anatomy in the utilization inpainted image.

7. The method of claim 6, wherein processing the second dental image using the generator machine learning model comprises processing the second dental image in combination with a mask indicating missing portions of the second dental image.

8. The method of claim 6, further comprising:
   processing, by the computer system, the utilization inpainted image and labels of dental anatomy according to a measuring machine learning model to obtain a measurement of a dental condition.

9. The method of claim 8, further comprising:
   processing, by the computer system, the utilization inpainted image, labels of dental anatomy, and measurement of the dental condition according to a diagnosing machine learning model to obtain a diagnosis of a dental pathology.

10. The method of claim 9, wherein the dental pathology is a diagnosis of a periodontal disease.

11. A non-transitory computer-readable medium storing executable instructions that, when executed by a processing device, cause the processing device to:
    receive a plurality of first dental images;
    receive or generate a random mask for each image of the plurality of first dental images;
    process each image of the plurality of first dental images and the random mask for the each image with a generator machine learning model to obtain an inpainted image for the each image, the inpainted image including image data generated by the generator machine learning model for image locations corresponding to the random mask for the each image; and
    for each image of the plurality of first dental images, update the generator machine learning model according to a training algorithm according to similarity of the each image to the inpainted image obtained for the each image;
    wherein each image of the plurality of first dental images is an image of dental anatomy according to an imaging modality selected from the group consisting of full mouth series X-rays, dental cone beam computed tomography (CBCT), cephalometric X-ray, intra-oral optical image, panoramic dental X-ray, dental magnetic resonance imaging (MRI) image, dental light detection and ranging (LIDAR) image.

12. The non-transitory computer-readable medium of claim 11, wherein the executable instructions, when executed by the processing device, further cause the processing device to:
    process the inpainted image for each first dental image of the plurality of first dental images and an unpaired dental image from a repository using a discriminator machine learning model to obtain a realism estimate; and
    update, by the training algorithm, the generator machine learning model and the discriminator machine learning model according to the realism estimates for the plurality of first dental images.

13. The non-transitory computer-readable medium of claim 12, wherein the generator machine learning model is an encoder-decoder machine learning model.

14. The non-transitory computer-readable medium of claim 13, wherein the generator machine learning model and the discriminator machine learning model are each convolution neural networks.

15. The non-transitory computer-readable medium of claim 12, wherein the realism estimate is a matrix of realism estimates.

16. The non-transitory computer-readable medium of claim 11, wherein the executable instructions, when executed by the processing device, further cause the processing device to:
    process a second dental image using the generator machine learning model to obtain a utilization inpainted image; and
    process the utilization inpainted image according to a labeling machine learning model to obtain labels of dental anatomy in the utilization inpainted image.

17. The non-transitory computer-readable medium of claim 16, wherein the executable instructions, when executed by the processing device, further cause the processing device to process the second dental image using the generator machine learning model by processing the second dental image in combination with a mask indicating missing portions of the second dental image.

18. The non-transitory computer-readable medium of claim 16, wherein the executable instructions, when executed by the processing device, further cause the processing device to:
   process the utilization inpainted image and labels of dental anatomy according to a measuring machine learning model to obtain a measurement of a dental condition.

19. The non-transitory computer-readable medium of claim 18, wherein the executable instructions, when executed by the processing device, further cause the processing device to:
   process the utilization inpainted image, labels of dental anatomy, and measurement of the dental condition according to a diagnosing machine learning model to obtain a diagnosis of a dental pathology.

20. The non-transitory computer-readable medium of claim 19, wherein the dental pathology is a diagnosis of a periodontal disease.

\* \* \* \* \*